US008242171B2

(12) United States Patent
Sinclair et al.

(10) Patent No.: US 8,242,171 B2
(45) Date of Patent: Aug. 14, 2012

(54) METHOD FOR REDUCING THE WEIGHT OF A SUBJECT OR INHIBITING WEIGHT GAIN IN A SUBJECT

(75) Inventors: David A. Sinclair, Chestnut Hill, MA (US); Maria Alexander-Bridges, West Newton, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 12/683,998

(22) Filed: Jan. 7, 2010

(65) Prior Publication Data

US 2010/0316679 A1    Dec. 16, 2010

Related U.S. Application Data

(63) Continuation of application No. 11/027,779, filed on Dec. 29, 2004, now abandoned.

(60) Provisional application No. 60/588,643, filed on Jul. 16, 2004, provisional application No. 60/533,712, filed on Dec. 29, 2003.

(51) Int. Cl.
*A61K 31/22* (2006.01)
*A61K 36/00* (2006.01)

(52) U.S. Cl. ......... 514/546; 514/909; 424/725; 424/776

(58) Field of Classification Search .................. 514/546, 514/909; 424/725, 776
See application file for complete search history.

(56) References Cited

U.S. PATENT DOCUMENTS

| | | | |
|---|---|---|---|
| 3,174,901 A | 3/1965 | Sterne et al. |
| 4,591,600 A | 5/1986 | Creuzet et al. |
| 4,598,089 A | 7/1986 | Hadvary et al. |
| 5,500,367 A | 3/1996 | Hain et al. |
| 5,689,046 A | 11/1997 | Schroder et al. |
| 5,689,047 A | 11/1997 | Hain et al. |
| 5,747,536 A | 5/1998 | Cavazza |
| 5,827,898 A | 10/1998 | Khandwala et al. |
| 5,874,399 A | 2/1999 | Samal |
| 5,874,444 A | 2/1999 | West |
| 5,945,106 A | 8/1999 | Sinnott |
| 5,985,647 A | 11/1999 | Schroder et al. |
| 6,008,260 A | 12/1999 | Pezzuto et al. |
| 6,020,129 A | 2/2000 | Schroder et al. |
| 6,022,901 A | 2/2000 | Goodman |
| 6,048,903 A | 4/2000 | Toppo |
| 6,063,820 A | 5/2000 | Cavazza |
| 6,063,988 A | 5/2000 | Hain et al. |
| 6,080,701 A | 6/2000 | Jeandet et al. |
| 6,124,125 A | 9/2000 | Kemp et al. |
| 6,132,740 A | 10/2000 | Hu |
| 6,147,121 A | 11/2000 | Breton et al. |
| 6,184,248 B1 | 2/2001 | Lee et al. |
| 6,190,716 B1 | 2/2001 | Galbreath, Jr. |
| 6,197,834 B1 | 3/2001 | Docherty |
| 6,211,247 B1 | 4/2001 | Goodman |
| 6,245,814 B1 | 6/2001 | Nag et al. |
| 6,264,995 B1 | 7/2001 | Newmark et al. |
| 6,270,780 B1 | 8/2001 | Carson et al. |
| 6,300,377 B1 | 10/2001 | Chopra |
| 6,319,523 B1 | 11/2001 | Zhou |
| 6,331,633 B1 | 12/2001 | Neogi et al. |
| 6,333,441 B1 | 12/2001 | Sato et al. |
| 6,355,692 B2 | 3/2002 | Docherty |
| 6,358,517 B1 | 3/2002 | Pillai et al. |
| 6,359,017 B1 | 3/2002 | Bruckner et al. |
| 6,361,815 B1 | 3/2002 | Zheng et al. |
| 6,368,617 B1 | 4/2002 | Hastings et al. |
| 6,387,416 B1 | 5/2002 | Newmark et al. |
| 6,410,596 B1 | 6/2002 | Hopp et al. |
| 6,414,037 B1 | 7/2002 | Pezzuto et al. |
| 6,416,806 B1 | 7/2002 | Zhou |
| 6,423,747 B1 | 7/2002 | Lanzendorfer et al. |
| 6,426,061 B1 | 7/2002 | Li et al. |
| 6,440,433 B1 | 8/2002 | Breton et al. |
| 6,448,450 B1 | 9/2002 | Nag et al. |
| 6,469,055 B2 | 10/2002 | Lee et al. |
| 6,475,530 B1 | 11/2002 | Kuhrts |
| 6,479,466 B1 | 11/2002 | Redfield et al. |
| 6,486,203 B1 | 11/2002 | Dannenberg |
| 6,500,451 B2 | 12/2002 | Adams |
| 6,515,020 B1 | 2/2003 | Cavazza |
| 6,537,969 B1 | 3/2003 | Blass |
| 6,541,522 B2 | 4/2003 | Inman et al. |
| 6,544,564 B1 | 4/2003 | Farley |

(Continued)

FOREIGN PATENT DOCUMENTS

DE      102 30 961 A1    2/2004

(Continued)

OTHER PUBLICATIONS

[No Author Listed], Aging Research's Family Feud, Science, Feb. 27, 2004;303:1276-1279.
[No Author Listed], American Federation for Aging Research, The Latest Research on Caloric Restriction and Animal and Human Longevity, Jul. 8, 2003.
[No Author Listed], Contents and Abstracts of Latest Issue of BBB. Biosciences, Biotechnology and Biochemistry. 2000;64(11):34 pages.
[No Author Listed], Grape Expections, The Boston Globe Editorial, Aug. 29, 2003.
[No Author Listed], Guarente Describes Investigation into Longevity Gene at Dean's Distinguished Lecture Series, Harvard Public Health Nov. Feb. 20, 2004:1-3.

(Continued)

*Primary Examiner* — Kevin E Weddington

(74) *Attorney, Agent, or Firm* — Wolf, Greenfield & Sacks, P.C.

(57) ABSTRACT

Provided herein are methods and compositions for modulating the activity or level of a sirtuin, thereby treating or preventing obesity or an insulin resistance disorder, such as diabetes in a subject. Exemplary methods comprise contacting a cell with a sirtuin activating compound or an inhibitory compound to thereby increase or decrease fat accumulation, respectively.

4 Claims, 20 Drawing Sheets

U.S. PATENT DOCUMENTS

| | | |
|---|---|---|
| 6,552,085 B2 | 4/2003 | Inman et al. |
| 6,552,213 B1 | 4/2003 | Deshpande et al. |
| 6,572,882 B1 | 6/2003 | Vercauteren et al. |
| 6,573,299 B1 | 6/2003 | Petrus |
| 6,576,660 B1 | 6/2003 | Liao et al. |
| 6,605,296 B1 | 8/2003 | Stuckler |
| 6,615,843 B2 | 9/2003 | Pera |
| 6,624,197 B1 | 9/2003 | Nag et al. |
| 6,638,543 B2 | 10/2003 | Kang et al. |
| 6,638,545 B1 | 10/2003 | Rombi |
| 6,656,925 B2 | 12/2003 | Petrus |
| 6,844,163 B1 | 1/2005 | Matsuzawa et al. |
| 7,119,110 B2 | 10/2006 | Bagchi et al. |
| 2001/0039296 A1 | 11/2001 | Bagchi et al. |
| 2001/0056071 A1 | 12/2001 | Pelliccia et al. |
| 2002/0002200 A1 | 1/2002 | Nag et al. |
| 2002/0009482 A1 | 1/2002 | Adams |
| 2002/0028852 A1 | 3/2002 | Ghai et al. |
| 2002/0051799 A1 | 5/2002 | Pruche et al. |
| 2002/0052407 A1 | 5/2002 | Lee et al. |
| 2002/0058701 A1 | 5/2002 | Inman et al. |
| 2002/0058707 A1 | 5/2002 | Hopp et al. |
| 2002/0091087 A1 | 7/2002 | Zhang et al. |
| 2002/0110604 A1 | 8/2002 | Babish et al. |
| 2002/0111383 A1 | 8/2002 | Hassen |
| 2002/0119952 A1 | 8/2002 | Petrus |
| 2002/0120008 A1 | 8/2002 | Benzer et al. |
| 2002/0142017 A1 | 10/2002 | Simonnet |
| 2002/0146424 A1 | 10/2002 | Benza et al. |
| 2002/0146472 A1 | 10/2002 | Chen et al. |
| 2002/0148478 A1 | 10/2002 | Pera |
| 2002/0155075 A1 | 10/2002 | Collington |
| 2002/0164385 A1 | 11/2002 | Dannenberg et al. |
| 2002/0173549 A1 | 11/2002 | Wurtman et al. |
| 2002/0182196 A1 | 12/2002 | McCleary |
| 2002/0192310 A1 | 12/2002 | Bland et al. |
| 2003/0004142 A1 | 1/2003 | Prior et al. |
| 2003/0004143 A1 | 1/2003 | Prior et al. |
| 2003/0031693 A1 | 2/2003 | Breton et al. |
| 2003/0044474 A1 | 3/2003 | Tao et al. |
| 2003/0044946 A1 | 3/2003 | Longo |
| 2003/0054053 A1 | 3/2003 | Young et al. |
| 2003/0054357 A1 | 3/2003 | Young et al. |
| 2003/0055114 A1 | 3/2003 | Young |
| 2003/0064913 A1 | 4/2003 | Sonis |
| 2003/0078212 A1 | 4/2003 | Li et al. |
| 2003/0082116 A1 | 5/2003 | Badejo et al. |
| 2003/0082203 A1 | 5/2003 | Farley |
| 2003/0082597 A1 | 5/2003 | Cannon et al. |
| 2003/0082647 A1 | 5/2003 | Reenan et al. |
| 2003/0084912 A1 | 5/2003 | Pera |
| 2003/0086986 A1 | 5/2003 | Bruijn et al. |
| 2003/0118536 A1 | 6/2003 | Rosenbloom |
| 2003/0118617 A1 | 6/2003 | Soby et al. |
| 2003/0124101 A1 | 7/2003 | Gu et al. |
| 2003/0124161 A1 | 7/2003 | Biatry et al. |
| 2003/0129247 A1 | 7/2003 | Ju et al. |
| 2003/0133992 A1 | 7/2003 | Bagchi et al. |
| 2003/0145354 A1 | 7/2003 | Milkowski et al. |
| 2003/0149261 A1 | 8/2003 | Schramm et al. |
| 2003/0152617 A1 | 8/2003 | Yatvin |
| 2003/0161830 A1 | 8/2003 | Jackson et al. |
| 2003/0161902 A1 | 8/2003 | Duncan |
| 2003/0165854 A1 | 9/2003 | Cunningham et al. |
| 2003/0180719 A1 | 9/2003 | Herget et al. |
| 2003/0182302 A1 | 9/2003 | Li |
| 2003/0185912 A1 | 10/2003 | Rosenbloom |
| 2003/0186898 A1 | 10/2003 | Maurya et al. |
| 2003/0190337 A1 | 10/2003 | Bissett |
| 2003/0190381 A1 | 10/2003 | Bland et al. |
| 2003/0191064 A1 | 10/2003 | Kopke |
| 2003/0199581 A1 | 10/2003 | Seligson et al. |
| 2003/0203973 A1 | 10/2003 | Cooper et al. |
| 2003/0207325 A1 | 11/2003 | Guarente et al. |
| 2003/0224077 A1 | 12/2003 | Mahe et al. |
| 2003/0228269 A1 | 12/2003 | DeRosa et al. |
| 2003/0232782 A1 | 12/2003 | Escalante-Semerena et al. |
| 2004/0002499 A1 | 1/2004 | Aggrawal |
| 2004/0005574 A1 | 1/2004 | Guarente et al. |
| 2004/0009197 A1 | 1/2004 | DeRosa et al. |
| 2004/0014682 A1 | 1/2004 | Ravagnan et al. |
| 2004/0014721 A1 | 1/2004 | Hensley et al. |
| 2004/0015020 A1 | 1/2004 | Deshpande et al. |
| 2004/0018987 A1 | 1/2004 | Hoffman et al. |
| 2004/0028607 A1 | 2/2004 | Verdin et al. |
| 2004/0067894 A1 | 4/2004 | Carola et al. |
| 2004/0209952 A1 | 10/2004 | Kim et al. |
| 2004/0249938 A1 | 12/2004 | Bunch |
| 2004/0259938 A1 | 12/2004 | Nag et al. |
| 2004/0265861 A1 | 12/2004 | Goldfarb |
| 2005/0020511 A1 | 1/2005 | Li et al. |
| 2005/0038125 A1 | 2/2005 | Smit et al. |
| 2005/0049208 A1 | 3/2005 | Kaufmann et al. |
| 2005/0070470 A1 | 3/2005 | Coy et al. |
| 2005/0096256 A1 | 5/2005 | Sinclair |
| 2005/0136429 A1 | 6/2005 | Guarente et al. |
| 2005/0136537 A1 | 6/2005 | Sinclair |
| 2005/0171027 A1 | 8/2005 | Sinclair et al. |
| 2005/0267023 A1 | 12/2005 | Sinclair et al. |
| 2006/0002914 A1 | 1/2006 | Milbrandt et al. |
| 2006/0014705 A1 | 1/2006 | Howitz et al. |
| 2006/0025337 A1 | 2/2006 | Sinclair et al. |
| 2006/0084085 A1 | 4/2006 | Sinclair et al. |
| 2006/0084135 A1 | 4/2006 | Howitz et al. |
| 2006/0111435 A1 | 5/2006 | Sinclair et al. |
| 2006/0229265 A1 | 10/2006 | Milburn et al. |
| 2006/0257502 A1 | 11/2006 | Liu |
| 2006/0276393 A1 | 12/2006 | Milburn et al. |
| 2006/0276416 A1 | 12/2006 | Sinclair et al. |
| 2007/0160586 A1 | 7/2007 | Alt et al. |

FOREIGN PATENT DOCUMENTS

| | | |
|---|---|---|
| EP | 1 064 931 A1 | 1/2001 |
| EP | 1 440 688 A1 | 7/2004 |
| JP | 09-143070 | 6/1997 |
| JP | 2002-080362 | 3/2002 |
| JP | 2003-524577 | 8/2003 |
| JP | 2003-252784 A | 9/2003 |
| JP | 2004-18376 A | 1/2004 |
| WO | WO 97/07790 A1 | 3/1997 |
| WO | WO 98/41113 A2 | 9/1998 |
| WO | WO 98/57928 A1 | 12/1998 |
| WO | WO 99/22728 A1 | 5/1999 |
| WO | WO 99/59561 A2 | 11/1999 |
| WO | WO 00/21526 A1 | 4/2000 |
| WO | WO 00/53176 A1 | 9/2000 |
| WO | WO 00/59522 A1 | 10/2000 |
| WO | WO 00/69430 A1 | 11/2000 |
| WO | WO 01/98291 A2 | 12/2001 |
| WO | WO 02/13811 A2 | 2/2002 |
| WO | WO 02/14252 A2 | 2/2002 |
| WO | WO 02/17959 A2 | 3/2002 |
| WO | WO 02/49575 A2 | 6/2002 |
| WO | WO 02/49994 A2 | 6/2002 |
| WO | WO 02/102981 A2 | 12/2002 |
| WO | WO 03/009838 A1 | 2/2003 |
| WO | WO 03/031404 A2 | 4/2003 |
| WO | WO 03/037316 A1 | 5/2003 |
| WO | WO 03/039535 A1 | 5/2003 |
| WO | WO 03/103583 A2 | 12/2003 |
| WO | WO 2004/016726 A2 | 2/2004 |
| WO | WO 2004/041758 A1 | 5/2004 |
| WO | WO 2004/096198 | 11/2004 |
| WO | WO 2004/105517 A1 | 12/2004 |
| WO | WO 2005/002527 A2 | 1/2005 |
| WO | WO 2005/002555 A1 | 1/2005 |
| WO | WO 2005/002672 A2 | 1/2005 |
| WO | WO 2005/004814 A2 | 1/2005 |
| WO | WO 2005/026112 A2 | 3/2005 |
| WO | WO 2005/053609 A2 | 6/2005 |
| WO | WO 2005/065667 A2 | 7/2005 |
| WO | WO 2006/078941 A2 | 7/2006 |
| WO | WO 2006/094236 A1 | 9/2006 |

OTHER PUBLICATIONS

[No Author Listed], Harvard Medical School, Molecules Discovered That Extend Life in Yeast, Human Cells, Science Blog, Aug. 2003.
[No Author Listed], Nicholas Wade, Study Spurs Hope of Finding Way to Increase Human Life, The New York Times, Aug. 25, 2003.
[No Author Listed] Resveratrol: Definition from Answers.com. 34 pages. Last accessed from http://www.answers.com/resveratrol on Nov. 19, 2010.
[No Author Listed], Study Sheds Light on Wine's Benefits, Reuters, Aug. 25, 2003.
[No Author Listed], Syndrome X, An Insulin Resistance Disorder. Healthyroads. Last Accessed on Mar. 9, 2007 from http://healthyroads.com/mylibrary/data/ash_ref/htm/art_syndromexaninsulinresistancedisorder.com. 4 pages.
[No Author Listed], The Health Benefits of Red Wine & Resveratrol. Advanced Health & Life Extension. Accessed Last on Dec. 29, 2009 from http://www.advanced-health.com/redwine.html. 5 pages.
[No Author Listed], To Red Wine, Long Life, Newsday.com , Aug. 26, 2003.
Aguilaniu et al., Asymmetric inheritance of oxidatively damaged proteins during cytokinesis. Science 2003 299:1751-1753.
Aiston et al., Glucose 6-phosphate causes translocation of phosphorylase in hepatocytes and inactivates the enzyme synergistically with glucose. Biochem J., 2004;377:195-204.
Anderson et al., Manipulation of a nuclear NAD+ salvage pathway delays aging without altering steady-state NAD+ levels, J Biol Chem. May 24, 2002;277(21):18881-90. Epub Mar. 7, 2002.
Anderson et al., Nicotinamide and PNCI govern lifespan extension by caloric restriction in *Saccharomyces cerevisiae*, Nature. May 8, 2003;423(6936):181-5.
Anderson et al., Yeast life-span extension by calorie restriction is independent of NAD fluctuation,. Science. Dec. 19, 2003;302(5653):2124-6. Epub Nov. 6, 2003.
Araki et al., Increased nuclear NAD biosynthesis and SIRT1 activation prevent axonal degeneration. Science. Aug. 13, 2004;305:1010-1013.
Arichi et al., Effects of stilbene components of the roots of Polygonum cuspidatum Sieb. et Zucc. on lipid metabolism. Chem Pharm Bull (Tokyo). May 1982;30(5):1766-70.
Bagchi et al., Phytoestrogen, resveratrol and women's health, research communications in pharmacology and toxicology, vol. 5., Nos. 1&2, 2000 XP-001018765.
Bastianetto et al., Reversatrol and red wine constituents: evaluation of their neuroprotective properties. Pharmaceutical News, 2001:8(5):33-38.
Bauer et al., Resveratrol improves health and survival of mice on a high-calorie diet. Nature Articles. Nature Publishing Group, 2006. pp. 1-6.
Bauer et al., Therapeutic potential of resveratrol: the in vivo evidence. Nature Reviews. Jun. 2006;5:493-506.
Bedalov et al., Identification of a small molecule inhibitor of Sir2p. PNAS, Dec. 18, 2001;98:15113-15118.
Bedalov et al., NAD to the rescue. Science Aug. 13, 2004;305:954-955.
Benguria et al., Sir2p suppresses recombination of replication forks stalled at the replication fork barrier of ribosomal DNA in *Saccharomyces cerrevisiae*. Nucleic Acids Research. 2003;31(3):893-898.
Bergeron et al., Effect of 5-aminoimidazole-4-carboxamide-1-13-D-ribofuranoside infusion on in vivo glucose and lipid metabolism in lean and obese zucker rats. Diabetes, May 2001;50:1076-1082.
Berkow et al., Merck Manual of Diagnosis and Therapy, 1987, Merck Manual of Diagnosis and Therapy, Rahway, Merck & Co., US, XP002141064:pp. 2392.
Bieganowski et al., Discoveries of nicotinamide riboside as a nutrient and conserved NRK genes establish a preiss-handler independent route to NAD+ in fungi and humans. Cell, May 4, 2004;117:495-502.
Bitterman et al., Longevity regulation in *Saccharomyces cerevisia*: linking metabolism, genome stability, and heterochromatin. Microbiol Mol Biol Rev. Sep. 2003;6793):376-99.
Bitterman et al., Inhibition of silencing and accelerated aging by nicotinamide, a putative negative regulator of yeast sir2 and human SIRT I. J Biol Chem. Nov. 22, 2002;277(47):45099-107. Epub Sep. 23, 2002.
Borra et al., Mechanism of human SIRT1 activation by resveratrol. J Biol Chem. Apr. 29, 2005; 280(17): 17 187-95. Epub Mar. 4, 2005.
Brachmann et al., The SIR2 gene family, conserved from bacteria to humans, functions in silencing, cell cycle progression, and chromosome stability. Genes & Development 1995 9:2888-2902.
Brandolini et al., Capillary electrophoresis determination, synthesis, and stability of resveratrol and related 3-O-B-D-glucopyranosides. Journal of Agricultural and Food Chemistry, 2002;50:7407-7411.
Brehm, The skinny of fat: MIT researchers establish first link between eating and aging, Massachusetts Institute of Technology, Jun. 2, 2004.
Brunet et al., Stress-dependent regulation of FOXO transcription factors by the SIRT1 deacetylase. Science. Mar. 26, 2004;303(5666):2011-5. Epub Feb. 19, 2004.
Bryk et al., Transcriptional silencing of Ty1 elements in the RDNI locus of yeast. Genes & Development 1997 11:255-269.
Campisi, Aging, chromatin, and food restriction-connecting the dots. Science, Sep. 22, 2000;289:2062-2063.
Chua et al., Mammalian SIRT1 limits replicative life span in response to chronic genotoxic street. Cell Metabolism, Jul. 2005;2:67-76.
Cohen et al., Acetylation of the C terminus of Ku70 by CBP and PCAF controls bax-mediated apoptosis. Mol Cell. Mar. 12, 2004;13:627-638.
Cohen et al., Calorie restriction promotes mammalian cell survival by inducing the SIRT1 deacetylase. Science, Jul. 16, 2004;305:390-392.
Coronado et al., Alfalfa root flavonoid production is nitrogen regulated. Plant Physiol. 1995;108:533-542.
Dai et al., SIRT1 activation by small molecules: kinetic and biophysical evidence for direct interaction of enzyme and activator. J Biol Chem. Oct. 22, 2010;285(43):32695-703. Epub Aug. 11, 2010.
Dajas et al., Cell culture protection and in vivo neuroprotective capacity of flavonoids. Neurotox Res. 2003;5(6):425-32. Abstract.
De Cabo et al., An in vitro model of caloric restriction. Experimental Gerontology, 2003;38:631-639.
Defossez et al., Elimination of replication block protein fobl extends the life span of yeast mother cells. Molecular Cell;1999 3:447-455.
Denu, Linking chromatin function with metabolic networks:SIR2 family of NAD+-dependent deacetylases. Trends in Biochemical Sciences. 2003;28(1):41-48.
*Dong, Molecular mechanism of the chemopreventive effect of resveratrol. Mutation Research 2003;523-524:145-150.
Ferguson, Role of plant polyphenols in genomic stability. Mutation Research. 2002;475:89-111.
Flam, PA Scientists may be on to antiaging compound. Philadelphia Inquirer; Sep. 10, 2003.
Frye et al., Phylogenetic classification of prokaryotic and eukaryotic Sir2-like proteins. Biochemical and Biophysical Research Communications. 2000;273:793-798.
Fukuhara et al., Visfatin: A Protein Secreted by Visceral Fat that Mimics the Effects of Insulin. Sciencexpress/www.sciencexpress.org/Dec. 16, 2004:1/10.1126.
GenBank Accession No. BC020691. Jun. 29, 2004. *Homo sapiens* pre-B-cell colony enhancing factor I.
GenBank Accession No. NP_005737. Oct. 28, 2004. pre-B-cell colony enhancing factor 1 isoform a.
GenBank Accession No. NP_877591. Oct. 27, 2004. pre-B-Cell colony enhancing factor 1 isoforrn b.
Glossmann et al., Quercetin inhibits tyrosine phosphorylation by the cyclic nucleotide-independent, transforming protein kinase, pp60. Naunyn-Schmiedeberg's Arch Pharmacol. 1981; 317:100-102.
Godfroid, Eulogy of wine. Presse Med. Dec. 20, 1997;26(40):1971-4.
Gottlieb et al., A new role for a yeast transcriptional silencer gene, SIR2, in regulation of recombination in ribosomal DNA. Cell;1989 56:771-776.
Graefe et al., Pharmacokinetics and bioavailability of the flavonol quercetin in humans. Intl. J. of Clin Pharmacology and Therapeutics, 1999;37(5):219-233.

Grozinger et al., Identification of a class of small molecule inhibitors of the sirtuin family of NAD-dependent deacetylases by phenotypic screening. J Biol. Chem. Oct. 19, 2001;276(42):38837-38843.

Guarente et al., Genetic pathways that regulate ageing in model organisms. Nature.2000;408:255-262.

Hekimi et al., Genetics and the specificity of the aging process. Science. 2003;299:1351-1354.

Hendrickson, A dietary magic bullet? Harvard team says pill will fight effects of high-fat eating. The Journal of New England Technology, Mass. High Tech, Dec. 8-14, 2003.

Herzenberg et al., The history and future of the fluorescence activated cell sorter and flow cytometry:a view from Stanford. Clinical Chemistry. 2002;48:10 1819-1827.

Hildebrandt, Pschyrembel Klinisches Woerterbuch, 1998, XP002141063:47-49.

Hirao et al., Identification of selective inhibitors of NAD+-dependent deacetylases using phenotypic screens in yeast. J Biol. Chem. Dec. 26, 2003;278(52):52773-58782.

Holla et al., New bis-aminomercaptotriazoles and bis-triazolothiadiazoles as possible anticancer agents. Eur. J. Med. Chem. 2002;37:511-517.

Holzenberger et al., IGF-1 receptor regulates lifespan and resistance to oxidative stress in mice. Nature. 2003;421:182-187.

Howitz et al., Small molecule activators of sirtuins extend *Sacdharomyces cerevisiae* lifespan. Nature, Sep. 11, 2003;425:191-196.

Hu et al., Antioxidants may contribute in the fight against ageing: an in vitro model. Mechanisms of Aging and Development, 2000;121:217-230.

Ignatowicz et al., Resveratrol, a natural chemopreventive agent against degenerative diseases. Pol J Pharmacol, 2001;53:557-569.

Imai et al., Transcriptional silencing and longevity protein Sir2 is an NAD-dependent histone deacetylase. Nature. 2000;403:795-800.

Jai et al., Pre-B cell colony-enhancing factor inhibits neutrophil apoptosis in experimental inflammation and clinical sepsis. J. Clin. Invest., 2004;113:1318-1327.

Jang et al., Cancer chemopreventive activity of resveratrol, a natural product derived from grapes. Science. 1997;275:218-220.

Jazwinski, Metabolic control and gene dysregulation in yeast aging. Annals New York Academy of Sciences. 2000;908:21-30.

Johnstone et al., Histone deacetylase inhibitors in cancer therapy: is transcription the primary target? Cancer Cell, Jul. 2003;4:13-18.

Kaeberlein et al., Grapes versus gluttony. Nature News 8 Views. Nature Publishing Group, 2006. pp. 1-2.

Kaeberlein et al., High osmolarity extends life span in *Saccharomyces cerevisiae* by a mechanism related to calorie restriction. Molecular and Cellular Biology, Nov. 2002;22(22):8056-8066.

Kaeberlein et al., Substrate-specific activation of sirtuins by resveratrol. J. Biol. Chem. 2005;280(17):17038-17045.

Kaeberlein et al., The SW/3/4 complex and SIR2 alone promote longevity in *Saccharomyces cerevisiae* by two different mechanisms. Genes & Development, 1999;13:2570-2580.

Kenyon, A conserved regulatory system for aging. Cell. 2001;105:165-168.

Khanna et al., Dermal would healing properties of redox-active grape seed proanthocyanidins. Free Radical Biology & Medicine, 2002;33(8):1089-1096.

Kimura et al., Pharmacological studies on resveratrol. Methods Find Exp Clin Pharmacol, 2003;25(4):297-310.

Koppes et al., Moderate alcohol consumption lowers the risk of type 2 diabetes. Diabetes Care. Mar. 2005; 28(3):719-725.

Koubova et al., How does calorie restriction work? Genes & Development, 2003;17:313-321.

Kris-Etherton et al., Bioactive compounds in foods: their role in the prevention of cardiovascular disease and cancer. Am. J. Med. 2002;113(9B):71S-88S.

Lacey et al., Glenn launches labs for aging research. Harvard Medical School Communications, Harvard University Gazette. Mar. 17, 2005.

Lamming et al., Small molecules that regulate lifespan: evidence for xenohormesis. Mol Microbiol. 2004;53(4):1003-9.

Landry et al., The silencing protein SIR2 and its homologs are NAD-dependent protein deacetylases. Proc. Natl.Acad. Sci. USA. 2000;97(11):5807-5811.

Langley et al., Human SIR2 deacetylates p53 and antagonizes PML/p53-induced cellular senescence. The EMBO Jurnal. 2002;21(10):2383-2396.

Lasalandra, Wine, less dine: age study eyes low-calorie diet . . . and a glass of red. Boston Herald, Aug. 25, 2003.

Laurenson et al., Silencers, silencing, and heritable transcriptional states. Microbiological Reviews.1992;56(4):543-560.

Ledford, Much ado about ageing. Nature. Mar. 2010;464:480-481.

Lin et al., Requirement of NAD and SIR2 for life-span extension by calorie restriction in *Saccharomyces cerevisiae*. Science, Sep. 22, 2000;289:2126-2128.

Longo et al., Evolutionary medicine: from dwarf model systems to healthy centenarians. Science. 2003;299:1342-1346.

Lui et al., Antimalarial alkoxylated and hydroxylated chalones: structure—activity relationship analysis. J. Med. Chem. 2004;(4):4443-4452.

Luo et al., Negative control of p53 by Sir2alpha promotes cell survival under stress. Cell. Oct. 19, 2001;107(2):137-48.

Mai et al., Histone deacetylation in eipgenetics:an attractive target for anticancer therapy. Medicinal Research Reviews, 2005;25:261-309.

Marcotte et al., Fluorescence assay of SIRT protein deacetylases using an acetylated peptide substrate and a secondary trypsin reaction. Analytical Biochemistry 332(2004):90-99.

Michael, Compound in Blueberries May Prevent Heart Disease and Type 2 Diabetes. Healthy Living NYC; 2005.

Middleton et al., The effects of plant flavonoids on mammalian cells: implications for inflammation, heart disease,and cancer. Pharmacol Rev. 2000;52:673-751.

Mills et al., *Mec*/-dependent redistribution of the Sir3 silencing protein from telomeres to DNA double-strand breaks. Cell. May 28, 1999;(97):609-620.

Milne, J.C. et al , Small molecule activators of SIRT1 as therapeutics for the treatment of type 2 diabetes. Nature 2007; 450: 712-716; and Supplementary Information pp. 1-17.

Monod et al., On the nature of allosteric transitions:a plausible model. J. Mol. Biol. 1965;12:88-118.

Morino et al., Specific regulation of HSPs in human tumor cell lines by flavonoids. In Vivo, 1997;11:265-270.

Motta et al., Mammalian SIRT-1 represses forkhead transcription factors. Cell, Feb. 20, 2004;116(4):551-63. Epub Feb. 5, 2004.

Nemoto et al., Nutrient availability regulates SIRT1 through a forkhead-dependent pathway. Science, Dec. 17, 2004;306:2105-2108.

Nicolini et al., Anti-apoptotic effect of trans-resveratrol on paclitaxel-induced apoptosis in the human neuroblastoma SH-SY5Y cell line. Neuroscience Letters. 2001;302:41-44.

Nothwehr et al., A Retention factor keeps death at bay. Nature Cell Biology, Apr. 11, 2003;5:281-283.

Oganesyan et al., Study of structure-activity (SA) interrelations in the flavonoid series: synthesis of chalcone derivatives and quantitative SA analysis. Khimiko-Farmatsevticheskii Zhurnal. 1986;20(6):696-702.

Ognjanovic et al., Genomic organization-of the gene coding for human pre-B-cell colony enhancing factor and expression in human fetal membranes. Journal of Molecular Endocrinology, 2001;16:107-117.

Oliver et al , Inhibition of mast cell Fc R1-mediated signaling and effector function by the syk-selective inhibitor, piceatannol. J. Biol. Chem. 1994;269(47):29697-29703.

Pacholec et al., SRT1720, SRT2183, SRT1460, and resveratrol are not direct activators of SIRT1. J Biol Chem. Mar. 12, 2010;285(11):8340-51. Epub Jan. 8, 2010 Supplemental Materials Included.

Pacholec et al., SRT1720, SRT2183 and SRT1460 do not activate Sirt1 with native substrates. Poster 30. FASEB Summer Research Conferences. Arizona. Jun. 21-26, 2009.

Pandey et al., Analysis of histone acetyltransferase and histone deacetylase families of *Arabidopsis thaliana* suggests functional diversification of chromatin modification among multicellular eukaryotes. Nucleic Acids Research.2002;30(23):5036-5055.

Parfiit et al., Antineopiastics and Immunosuppressants. Pharmaceutical Press, London, 1995, XP002329271, Martindale 32" ed.

Park et al., Effects of mutations in DNA repair genes on formation of ribosomal DNA circles and life span in *Saccharomyces cerevisiae*. Molecular and Cellular Biology. 1999;19(5):3848-3856.

Perez et al., Synthesis and characterization of complexes of p-isopropyl benzaldehyde and methyl 2-pyridyl ketone thiosemicarbazones with Zn(II) and Cd(II) metallic centers. Cytotoxic activity and induction of apoptosis in pam-ras cells. J. of Inorganic Biochemistry, 1999;75:255-261.

Picard et al., Sirt1 promotes fat mobilization in white adipocytes by repressing PPAR. Nature, Jun. 17, 2004;429(6993):771-6. Epub Jun. 2, 2004.

Polgreen, Selling Red Wine as Good (and Good for You), The New York Times, Aug. 26, 2003.

Pont et al., Relation between the chemical structure and the biological activity of hydroxystilbenes against botrytis cinerea. J. Phytopathology;1990 130:1-8.

Procu et al., The emerging therapeutic potential of sirtuin-interacting drugs: from cell death to lifespan extension. Trends in Pharmacological Sciences, Feb. 2005;26(2): 94-103.

Pugh et al., Controlling caloric consumption: protocols for rodents and rhesus monkeys. Neurobiology of Aging, Apr. 20, 1999:157-165.

Raffaelli et al., Identification of a novel human nicotinamide mononucleotide adenylyltransferease. Biochem Biophys Res Commun Oct. 4, 2002;297 (Abstract only).

Regev-Shoshani et al., Glycosylation of resveratrol protects it from enzymatic oxidation. Biochemical Journal Aug. 15, 2003;324:157. e-pub Apr. 16, 2003.

Revollo et al., The NAD biosynthesis pathway mediated by nicotinamide phosphoribosyltransferase regulates Sir2 activity in mammalian cells. The Journal of Biological Chemistry, Dec. 3, 2004;279(49):50754-50763.

Rogina et al., Longevity regulation by drosophila Rpd3 deacetylase and caloric restriction. Science, Nov. 29, 2002;298:1745.

Rowland, Do life spans of biblical proportions await us?, The Atlanta Journal Constitution, Sep. 2, 2003.

Samal et al., Cloning and Characterization of the cDNA Encoding a novel Human Pre-B-Cell Colony-Enhancing Factor, Molecular and Cellular Biology, Feb. 1994;14(2):1431-1437.

Sampson, Compound Identified in Grapes May Fight Cancer and Diabetes, htt://prohealth.com. May 27, 2002.

Sandmeier et al., Telomeric and rNDA silencing in *Saccharomyces cerevisiae* are dependent on a nuclear NAD+ .salvage pathway,. Genetics, Mar. 2002;160:877-889.

Sawada et al., Cytoprotective membrane-permeable peptides designed from the Bax-binding domain of Ku70. Nat Cell Biol. Apr. 2003;5(4):352-7.

Sawada et al., Ku70 suppresses the apoptotic translocation of Bax to mitochondria. Nat Cell Biol. Apr. 2003;5(4):320-9. Abstract.

Shimokawa et al., Life span extension by reduction of the growth hormone-insulin-like growth factor-1 axis:relation to caloric restriction. FASEB J. 2003;17:1108-1109.

Sinclair, Sirtuins for healthy neurons. Nat Genet. Apr. 2005; 37(4):339-40.

Sinclair, Extrachrornosomal rDNA circles-a cause of aging in yeast. Cell. 1997;91:1033-1042.

Sinclair, Paradigms and pitfalls of yeast longevity research. Mechanisms of Ageing and Development. 2002;123:857-867.

Smith et al., A phylogenetically conserved NAD+-dependent protein deacetylase activity in the Sir2 protein family. Proc. Natl. Acad. Sci. USA, Jun. 6, 2000;97(12):6658-6663.

Smith et al., An unusual form of transcriptional silencing in yeast ribosomal DNA. Genes & Development. 1997;11:241-254.

Smith, In Lab, seeking secret of youth, Chemical abundant in red wine appears to slow aging in study, The Boston Globe, Aug. 25, 2003.

Soleas et al., Resveratrol: a molecule whose time has come? And gone?. Clinical Biochemistry. 1997;30(2):91-113.

Solomon et al , Inhibition of SIRT1 catalytic activity increases p53 acetylation but does not alter cell survival following DNA damage. Mol. Cell. Biol. 2006;26(1):28-38.

South, Resveratrol & Quercetin—pro Heart & anti-Cancer, Offshore Pharmacy, Jun. 26, 2003 or earlier.

Stojanovi et al., Efficiency and mechanism of the antioxidant action of trans-resveratrol and its analogues in the radical liposome oxidation. Archives of Biochemistry and BiophySics. 2001;391(1):79-89.

Subramanian et al., Ku70 acetylation mediates neuroblastorna cell death induced by histone deacetylase inhbitors. PNAS, Mar. 29, 2005;102(13):4842-4847.

Sun et al., The "French Paradox" and beyond: neuroprotective effects of polyphenols. Free Radic Biol Med.2002; 15;32(4):314-8.

Tanasescu et al., Alcohol consumption and risk of coronary heart disease among individuals with type 2 diabetes. Curr. Diab. Rep. Oct. 1, 2001; (2):187-91.

Tanner et al., Silent information regulator 2 family of NAD-dependent histone/protein deacetylases generates a unique product, 1-0-acetyl-ADP-ribose. Proc. Natl. Acad. Sci. USA. 2000;97(26):14178-14182.

Tanny et al., An enzymatic activity in the yeast Sir2 protein that is essential for gene silencing. Cell. 1999;99:735-745.

Tanny et al., Coupling of histone deacetylation to NAD breakdown by the yeast silencing protein Sir2: evidence for acetyl transfer from substrate to an NAD breakdown product. Proc. Natl. Acad. Sci. USA. 2001;98(2):415-420.

Tartar et al., The endocrine regulation of aging by insulin-like signals. Science. 2003; 299:1346-1351.

Tissenbaum et al., Increased dosage of a sir-2 gene extends lifespan in *Caenorhabditis elegans*. Nature. 2001;410:227-230.

Vaziri et al., hSIR2SIRT1 functions as an NAD-Dependent p53 deacetylase. Cell, Oct. 2001;107:149-159.

Vergnes et al., Cytoplasmic SIR2 homologue overexpression promotes survival of Leishmania parasites by preventing programmed cell death. Gene. 2002;296:139-150.

Vessal et al., Antidiabetic effects of quercetin in streptozocin-induced diabetic rats. Comp Biochem Physiol C Toxicol Pharmacol. Jul. 2003;135C(3):357-64.

Wasowicz, Red wine ingredient may extend life. United Press International, Aug. 28, 2003.

Weiss, Enzymes Found to Delay Aging Process, The Washington Post, Aug. 25, 2003.

Windholz et al., Glutaric acid. The Merck Index, An Encyclopedia of Chemicals, Drugs and Biologicals. 10th Edition. 1983:642 Abstract 4334.

Wood et al., Sirtuin activators mimic caloric restriction and delay ageing in metazoans. Nature. Aug. 5, 2004;430(7000):686-9. Epub Jul. 14, 2004.

Wu et al., Ginkgo biloba extract EGb 761 increases stress resistance and extends life span of *Caenorhabditis elegans*. Cell Mol Biol,(Noisy-le-grand). 2002; 48(6):725-31.

Yoshida et al., Histone deacetylase as a new target for cancer chemotherapy. Cancer Chemother Pharmacol, 2001;48(1):520-526.

Zern et al., Grape polyphenols decrease plasma triglycerides and cholesteral accumulation in the aorta of ovariectomized guinea pigs. J. Nutr., 2003;133:2268-2272.

Zhang et al., Crystal structures of *E. coli* nicotinate mononucleotide adenylyltransferase and its complex with deamido-NAD. Structure, 2002 Ianuary;10:69-79.

Zhao et al., Structural basis for nicotinamide cleavage and ADP-ribose transfer by NAD +—dependant Sir2 histone/protein deacetylases. PNAS, Jun. 8, 2004;101(23):8563-8. Epub May 18, 2004.

Zhou et al., Role of AMP-activated protein kinase in mechanism of metformin action. The Journal of Clinical Investigation, Oct. 2001;108(8):1167-1174.

Couzin-Frankel, Genetics. Aging genes: the sirtuin story unravels. Science. Dec. 2, 2011;334(6060):1194-8.

Iwashita et al., Effect of flavonoids on the differentiation of 3T3-L1 adipoctes. Food Science and Technology Rsearch. 2001;7(2):154-160.

Kuppusamy et al., Effects of flavonoids on cyclic AMP phosphodiesterase and lipid mobilization in rat adipocytes. Biochem Pharmacol. Oct. 6, 1992;44(7):1307-15.

Kuppusamy et al., Potentiation of beta-adrenoceptor agonist-mediated lipolysis by quercetin and fisetin in isolated rat adipocytes. Biochem Pharmacol. Feb. 9, 1994;47(3):521-9.

Park et al., Resveratrol ameliorates aging-related metabolic phenotypes by inhibiting cAMP phosphodiesterases. Cell. Feb. 3, 2012;148(3):421-33.

Tennen et al., Finding a target for resveratrol. Cell. Feb. 3, 2012;148(3):387-9.

METHOD FOR REDUCING THE WEIGHT OF A SUBJECT OR INHIBITING WEIGHT GAIN IN A SUBJECT

RELATED APPLICATIONS

This application is a continuation of U.S. application Ser. No. 11/027,779, filed on Dec. 29, 2004, which claims the benefit of the priority filing date of U.S. provisional patent application No. 60/533,712 filed on Dec. 29, 2003 and of U.S. provisional patent application No. 60/588,643 filed on Jul. 16, 2004; all of the foregoing applications are incorporated herein in their entirety.

GOVERNMENT SUPPORT

This invention was made with government support under Grant numbers GM068072 and 5RO1-AG19892 awarded by the National Institutes of Health, and Grant number GM068076 awarded by the Public Health Service/National Institutes of Health. The Government has certain rights in this invention.

BACKGROUND

Obesity is a chronic condition that is characterized by a body mass index (BMI) over 25. Both congenital and environmental factors, such as exercise and eating habits, contribute to the disease. For instance, the hormone leptin has been shown to be involved in fat accumulation and regulating eating behavior. Several animal models of obesity result from mutations in the leptin and/or leptin receptor gene. In addition to affecting the lifestyle of an individual, obesity can lead to a number of complications and diseases, including insulin resistance, Type II diabetes, gallbladder disease, hypertension, cardiovascular disease, hyperlipidemia, sleep apnea, coronary artery disease, knee osteoarthritis, gout, infertility, breast cancer, endometrial cancer, colon cancer and lower back pain.

Diabetes is a disease that shows an acute symptom due to a remarkably high blood sugar or ketoacidosis, or as well as chronic, general metabolic abnormalities arising from a prolonged high blood sugar status or a decrease in glucose tolerance. Both congenital and environmental factors, such as exercise and eating habits, contribute to the disease. The pathogenic causes of diabetes are insulin productive disorders, secretion disorders or reductions in activities and sensitivities of the secreted insulin. Diabetes is largely grouped into the following two types: insulin-dependent diabetes mellitus (also known as Type I diabetes) and non-insulin-dependent diabetes mellitus (also known as Type II diabetes). The incidence of Type II diabetes is remarkably increased in obese patients.

Treatments for obesity are generally directed to suppressing the appetite of the subject. Whereas a number of appetite suppressants are available (diethylpropion tenuate, mazindol, orlistat, phendimetrazine, phentermine, sibutramine), these compounds may not be effective in all subjects or may be of limited efficacy. Accordingly, new treatments for obesity are needed.

A number of treatments for diabetes are well known and include oral hypoglycemic agents such as sulfonylureas that increase insulin secretion (for example, tolbutamide, chlorpropamide and glibenclamide), biguanides (for example, metformin and buformin) that increase glucose uptake and utilization and α-glucosidase inhibitors (for example, acarbose and voglibose). In addition, thiazolidinediones, such as troglitazone, rosiglitazone and pioglitazone, are used to ameliorate insulin-resistance. However, thiazolidinedione intake is usually associated with a weight gain. Thus, there is a still a need for more effective therapies for diabetes.

Currently 8% and 15% of adults in the United States are diabetic or obese, respectively. With the number of individuals affected with diabetes, particularly with type II diabetes, and obesity on the increase, there is a dire need for medications that prevent and treat these conditions.

SUMMARY

Provided herein are methods for treating or preventing obesity and/or insulin resistance disorders, such as diabetes in a subject. In one embodiment, the method comprises administering to a subject in need thereof a therapeutically effective amount of an agent that increases the activity and/or protein level of a sirtuin, such as SIRT1 or Sir2. The agent may be a sirtuin-activating compound, or a salt or prodrug thereof. The sirtuin-activating compound preferably stimulates human Sir2, i.e., SIRT1, protein activity. The sirtuin-activating compound preferably is a compound, which has a formula selected from the group consisting of formulas 1-18 or a salt or prodrug thereof. Sirtuin-activating compounds may be flavones, stilbenes, flavanones, isoflavones, catechins, chalcones, tannins and anthocyanidins or analogs or derivatives thereof. Sirtuin-activating compounds may be selected from the group consisting of resveratrol, butein, piceatannol, isoliquiritgenin, fisetin, luteolin, 3,6,3',4'-tetrahydroxyfalvone, quercetin, and analogs and derivatives thereof. Preferred sirtuin activating compounds also increase the activity and/or protein level of 5'-AMP-activated protein kinase (AMPK).

In certain embodiments, the method further comprises administering to the subject a therapeutically effective amount of a second agent that: (i) increases the activity and/or protein level of 5'-AMP-activated protein kinase (AMPK); (ii) increases the activity and/or protein level of a sirtuin; (iii) is an anti-diabetic agent; or (iv) is an anti-obesity agent.

Also provided herein are methods for promoting weight gain in a subject, e.g., for treating cachexia comprising administering to a subject in need thereof a therapeutically effective amount of an agent that decreases the activity and/or protein level of a sirtuin, such as SIRT1 or Sir2. Preferably, the sirtuin-inhibitory compound is a compound selected from the group of compounds represented by formulas 19-21, or a salt or prodrug thereof. Preferred sirtuin inhibitory compounds also decrease or inhibit the activity and/or protein level of 5'-AMP-activating protein kinase (AMPK). In certain embodiments, the method further comprises administering to the subject a therapeutically effective amount of a second agent that: (i) decreases the activity and/or protein level of a sirtuin; (ii) decreases the activity and/or protein level of 5'-AMP-activated protein kinase (AMPK); or (iii) is an agent for promoting weight gain.

Also provided is the use of a sirtuin-activating compound, alone or in conjunction with a second agent, for the manufacture of a medicament for treating or preventing an insulin resistance disorder and the use of a sirtuin inhibitory compound, alone or in conjunction with a second agent, for the manufacture of a medicament for promoting weight gain in a subject.

DETAILED DESCRIPTION

Definitions

Figure 1:
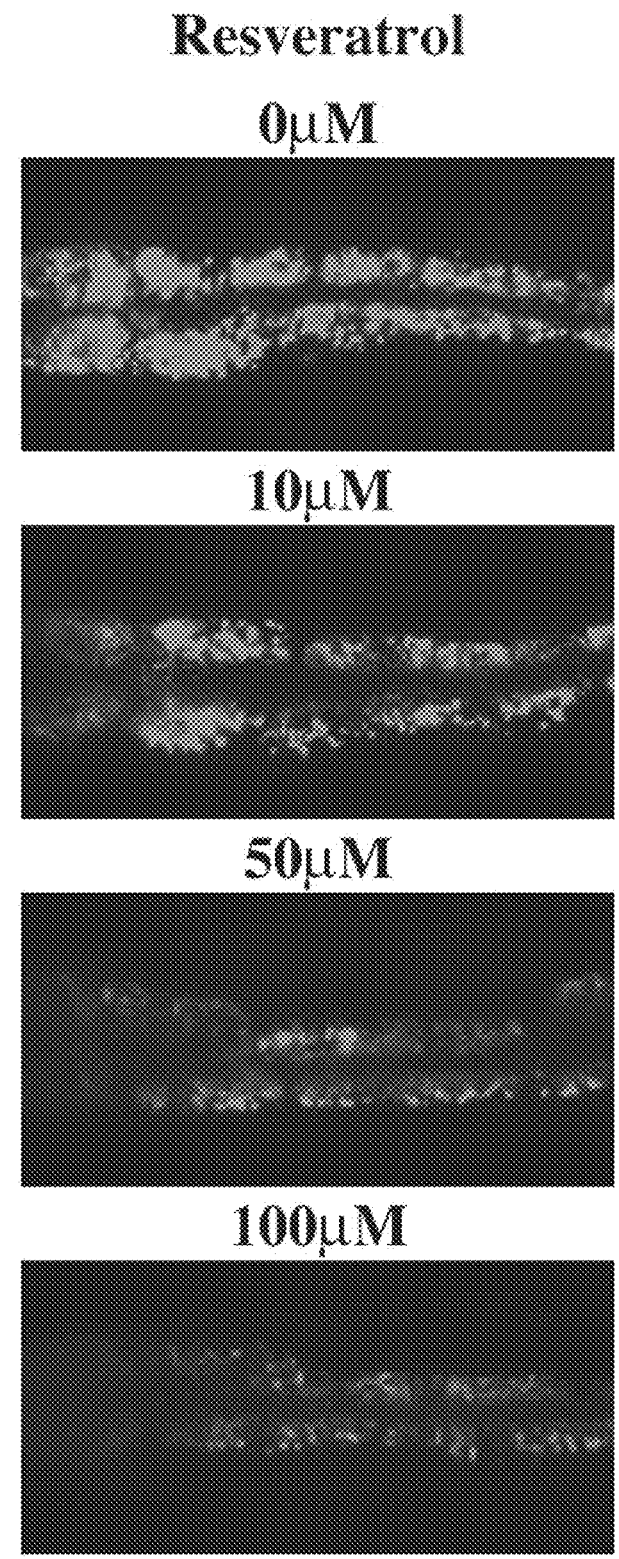
FIG. 1 is a series of photomicrographs that depict the effect of the sirtuin-activating compound resveratrol at different concentrations to induce fat mobilization as indicated by a decrease in Nile Red staining.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

"Sirtuin activation" refers to increasing at least one activity of a sirtuin protein, preferably by at least about 10%, 50%, 100% or more. "Activating a sirtuin protein" refers to the action of producing an activated sirtuin protein, i.e., a sirtuin protein that is capable of performing at least one of its biological activities with an increase of activity of at least about 10%, 50%, 2 fold or more. Biological activities of sirtuin proteins include deacetylation, e.g., of histones and p53; extending lifespan; increasing genomic stability; silencing transcription; and controlling the segregation of oxidized proteins between mother and daughter cells.

An "activating compound," "sirtuin-activating compound," or a "sirtuin activator" refers to a compound that activates a sirtuin protein or stimulates or increases at least one activity of a sirtuin protein. In certain embodiments, a sirtuin-activating compound may have a formula selected from the group of formulas 1-18.

"Sirtuin inhibition" refers to decreasing at least one activity of a sirtuin protein, preferably at least about 10%, 50%, 100% or more.

An "inhibitory compound" or "inhibiting compound" or "sirtuin inhibitory compound" refers to a compound that inhibits at least one activity of a sirtuin protein. In certain embodiments, a sirtuin inhibitory compound may have a formula selected from the group consisting of formulas 19-21.

A "form that is naturally occurring" when referring to a compound means a compound that is in a form, e.g., a composition, in which it can be found naturally. For example, since resveratrol can be found in red wine, it is present in red wine in a form that is naturally occurring. A compound is not in a form that is naturally occurring if, e.g., the compound has been purified and separated from at least some of the other molecules that are found with the compound in nature. A "naturally occurring compound" refers to a compound that can be found in nature, i.e., a compound that has not been designed by man. A naturally occurring compound may have been made by man or by nature.

"Sirtuin protein" refers to a member of the sirtuin deacetylase protein family or preferably to the Sir2 family, which include yeast Sir2 (GenBank Accession No. P53685), C. elegans Sir-2.1 (GenBank Accession No. NP_501912), and human SIRT1 (GenBank Accession No. NM_012238 and NP_036370 (or AF083106), set forth as SEQ ID NOs: 1 and 2, respectively) and SIRT2 (GenBank Accession No. NM_030593 and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

A "direct activator" of a sirtuin is a molecule that activates a sirtuin by binding to it. A "direct inhibitor" of a sirtuin is a molecule that inhibits a sirtuin by binding to it.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy; nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

"Obese" individuals or individuals suffering from obesity are generally individuals having a body mass index (BMI) of at least 25 or greater. Obesity may or may not be associated with insulin resistance.

The terms "comprise" and "comprising" are used in the inclusive, open sense, meaning that additional elements may be included.

The term "including" is used to mean "including but not limited to". "Including" and "including but not limited to" are used interchangeably.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a nonnatural arrangement.

A "patient," "individual," "subject" or "host" refers to either a human or a non-human animal.

The term "substantially homologous" when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

The term "modulation" is art-recognized and refers to up regulation (i.e., activation or stimulation), down regulation (i.e., inhibition or suppression) of a response, or the two in combination or apart.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "mammal" is known in the art, and exemplary mammals include humans, primates, bovines, porcines, canines, felines, and rodents (e.g., mice and rats).

The term "bioavailable" when referring to a compound is art-recognized and refers to a form of a compound that allows for it, or a portion of the amount of compound administered, to be absorbed by, incorporated to, or otherwise physiologically available to a subject or patient to whom it is administered.

The term "pharmaceutically-acceptable salt" is art-recognized and refers to the relatively non-toxic, inorganic and organic acid addition salts of compounds, including, for example, those contained in compositions described herein.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

"Transcriptional regulatory sequence" is a generic term used throughout the specification to refer to DNA sequences, such as initiation signals, enhancers, and promoters, which induce or control transcription of protein coding sequences with which they are operable linked. In preferred embodiments, transcription of one of the recombinant genes is under the control of a promoter sequence (or other transcriptional regulatory sequence) which controls the expression of the recombinant gene in a cell-type which expression is intended. It will also be understood that the recombinant gene can be under the control of transcriptional regulatory sequences which are the same or which are different from those sequences which control transcription of the naturally-occurring forms of genes as described herein.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions. As used herein, "expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

"Treating" a condition or disease refers to curing as well as ameliorating at least one symptom of the condition or disease.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease or condition being treated, the weight and age of the subject, the severity of the disease or condition, the manner of administration and the like, which can readily be determined by one of ordinary skill in the art. For example, certain compositions described herein may be administered in a sufficient amount to produce a desired effect at a reasonable benefit/risk ratio applicable to such treatment.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "structure-activity relationship" or "(SAR)" is art-recognized and refers to the way in which altering the molecular structure of a drug or other compound alters its biological activity, e.g., its interaction with a receptor, enzyme, nucleic acid or other target and the like.

The term "aliphatic" is art-recognized and refers to a linear, branched, cyclic alkane, alkene, or alkyne. In certain embodiments, aliphatic groups in the present compounds are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphtalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is a rt-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

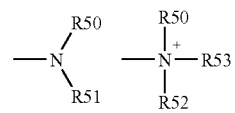

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

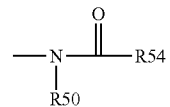

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

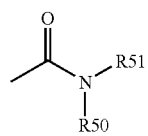

wherein R50 and R51 are as defined above. Certain embodiments of amides may not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carbonyl" is art recognized and includes such moieties as may be represented by the general formulas:

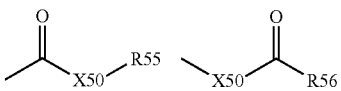

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and refers to a moiety that may be represented by the general formula:

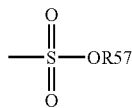

in which R57 is an electron pair, hydrogen, alkyl, cycloalkyl, or aryl.

The term "sulfate" is art recognized and includes a moiety that may be represented by the general formula:

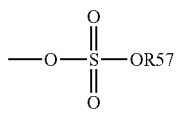

in which R57 is as defined above.

The term "sulfonamido" is art recognized and includes a moiety that may be represented by the general formula:

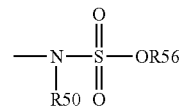

in which R50 and R56 are as defined above.

The term "sulfamoyl" is art-recognized and refers to a moiety that may be represented by the general formula:

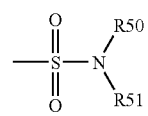

in which R50 and R51 are as defined above.

The term "sulfonyl" is art-recognized and refers to a moiety that may be represented by the general formula:

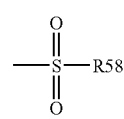

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

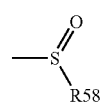

in which R58 is defined above.

The term "phosphoryl" is art-recognized and may in general be represented by the formula:

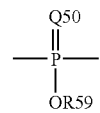

wherein Q50 represents S or O, and R59 represents hydrogen, a lower alkyl or an aryl. When used to substitute, e.g., an alkyl, the phosphoryl group of the phosphorylalkyl may be represented by the general formulas:

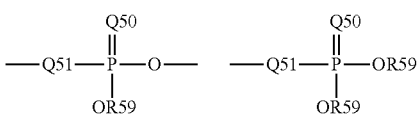

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

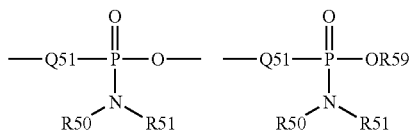

wherein Q51, R50, R51 and R59 are as defined above.

The term "phosphonamidite" is art-recognized and may be represented in the general formulas:

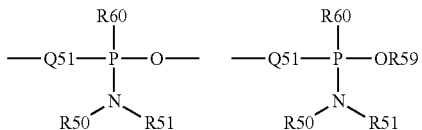

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls. The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions described herein may exist in particular geometric or stereoisomeric forms. In addition, compounds may also be optically active. Contemplated herein are all such compounds, including cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. All such isomers, as well as mixtures thereof, are encompassed herein.

If, for instance, a particular enantiomer of a compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. Heteroatoms such as nitrogen may have hydrogen substituents and/or any permissible substituents of organic compounds described herein which satisfy the valences of the heteroatoms. Compounds are not intended to be limited in any manner by the permissible substituents of organic compounds.

The chemical elements are identified in accordance with the Periodic Table of the Elements, CAS version, *Handbook of Chemistry and Physics,* 67th Ed., 1986-87, inside cover.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* ($2^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl(—$CH_2C_6H_5$), acyl[C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59 (McGraw Hill Book Company: New York, 1977). The Hammett constant values are generally negative for electron donating groups ($\sigma(P)$=-0.66 for $NH_2$) and positive for electron withdrawing groups ($\sigma(P)$=0.78 for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

Exemplary Sirtuin-Activating Compounds and Methods of Use

The following examples show that activators of sirtuins, such as resveratrol, butein, fisetin, piceatannol, quercetin and 3,5-dihydroxy-4-'-thiomethyl-trans-stilbene stimulates fat metabolism by reducing fat accumulation (See examples 1, 8 and 9) as well as inhibit adipogenesis (example 6); that Sir2 and AMPK are necessary for resveratrol mediated fat mobilization (See examples 3 and 4); that resveratrol stimulates AMPK and ACC phosphorylation (See example 5); that resveratrol boosts insulin sensitivity of adipocytes (See example 10) and that resveratrol, like other AMPK activators, can stimulate fatty acid oxidation in lipogenic cells (See example 11).

Exemplary sirtuin-activating compounds that activate sirtuins are described in Howitz et al. (2003) Nature 425: 191 and include: for example, resveratrol (3,5,4'-Trihydroxy-trans-stilbene), butein (3,4,2',4'-Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahyddroxyflavone), quercetin (3,5,7,3',4'-Pentahydroxyflavone), Deoxyrhapontin (3,5-Dihydroxy-4'-methoxystilbene 3-O-β-D-glucoside); trans-Stilbene; Rhapontin (3,3',5-Trihydroxy-4'-methoxystilbene 3-O-β-D-glucoside); cis-Stilbene; Butein (3,4,2',4'-Tetrahydroxychalcone); 3,4,2'4'6'-Pentahydroxychalcone; Chalcone; 7,8,3',4'-Tetrahydroxyflavone; 3,6,2',3'-Tetrahydroxyflavone; 4'-Hydroxyflavone; 5,4'-Dihydroxyflavone; 5,7-Dihydroxyflavone; Morin (3,5,7,2',4'-Pentahydroxyflavone); Flavone; 5-Hydroxyflavone; (−)-Epicatechin (Hydroxy Sites: 3,5,7,3',4'); (−)-Catechin (Hydroxy Sites: 3,5,7,3',4'); (−)-Gallocatechin (Hydroxy Sites: 3,5,7,3',4',5') (+)-Catechin (Hydroxy Sites: 3,5,7,3',4'); 5,7,3',4',5'-pentahydroxyflavone; Luteolin (5,7,3',4'-Tetrahydroxyflavone); 3,6,3',4'-Tetrahydroxyflavone; 7,3',4',5'-Tetrahydroxyflavone; Kaempferol (3,5,7,4'-Tetrahydroxyflavone); 6-Hydroxyapigenin (5,6,7,4'-Tetrahydroxyflavone); Scutellarein); Apigenin (5,7,4'-Trihydroxyflavone); 3,6,2',4'-Tetrahydroxyflavone; 7,4'-Dihydroxyflavone; Daidzein (7,4'-Dihydroxyisoflavone); Genistein (5,7,4'-Trihydroxyflavanone); Naringenin (5,7,4'-Trihydroxyflavanone); 3,5,7,3',4'-Pentahydroxyflavanone; Flavanone; Pelargonidin chloride (3,5,7,4'-Tetrahydroxyflavylium chloride); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole-4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.$H_2O$); Ambroxol (trans-4-(2-Amino-3,5-dibromobenzylamino)cyclohexane.HCl; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol.2HCl). Analogs and derivatives thereof can also be used.

Other sirtuin-activating compounds may have any of formulas 1-18 below. In one embodiment, a sirtuin-activating compound is a stilbene or chalcone compound of formula 1:

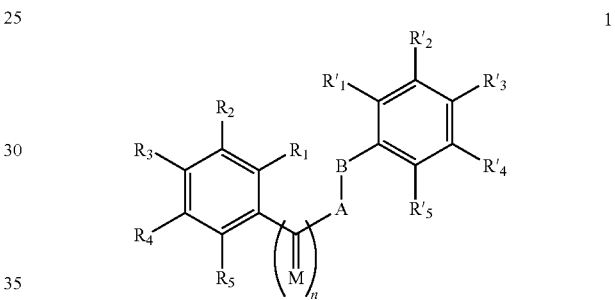

wherein, independently for each occurrence, $R_1$, $R_2$, $R_3$, $R_4$, $R_5$, $R'_1$, $R'_2$, $R'_3$, $R'_4$, and $R'_5$ represent H, alkyl, aryl, heteroaryl, alkaryl, heteroaralkyl, halide, $NO_2$, SR, OR, $N(R)_2$, or carboxyl;

R represents H, alkyl, or aryl;

M represents O, NR, or S;

A-B represents a bivalent alkyl, alkenyl, alkynyl, amido, sulfonamido, diazo, ether, alkylamino, alkylsulfide, or hydrazine group; and n is 0 or 1;

provided that when n is 0:

when $R_2$ and $R_4$ are OR, and $R_1$, $R_3$, $R_5$, $R'_1$, $R'_2$, $R'_4$, and $R'_5$ are H, and A-B is alkenyl, $R'_3$ is not Cl, F, —$CH_3$, —$CH_2CH_3$, —SMe, $NO_2$, i-propyl, —OMe, or carboxyl;

when A-B is alkyl or amido, $R_2$ and $R_4$ are not both OH;

when $R_3$ is OR at least one of $R'_1$, $R'_2$, $R'_3$, $R'_4$, or $R'_5$ is not H; and $R_4$ is not carboxyl.

In a further embodiment, the compound is a compound as shown as of formula 1 with attendant definitions, wherein the n is 0. In a further embodiment, the compound is a compound as shown as formula 1 and the attendant definitions, wherein the n is 1. In a further embodiment, the compound is a compound as shown as formula 1 and the attendant definitions, wherein the A-B is ethenyl. In a further embodiment, the compound is a compound as shown as formula 1 and the attendant definitions, wherein the A-B is —$CH_2CH(Me)CH(Me)CH_2$—. In a further embodiment, the compound is a compound as shown as formula 1 and the attendant definitions, wherein the M is O. In a further embodiment, the compound is a compound as shown as formula 1 and the attendant definitions, wherein $R_1$, $R_2$, $R_3$, $R_4$, $R_5$, $R'_1$, $R'_2$, $R'_3$, $R'_4$, and $R'_5$ are H. In a further embodiment, the compound is a compound as shown as formula 1 and the attendant definitions, wherein $R_2$, $R_4$, and $R'_3$ are OH. In a further embodiment, the compound is a compound as shown as formula 1 and the attendant definitions, wherein $R_2$, $R_4$, $R'_2$ and $R'_3$ are OH. In a further embodiment, the compound is a compound as shown as formula 1 and the attendant definitions, wherein the $R_3$, $R_5$, $R'_2$ and $R'_3$ are OH. In a further embodiment, the compound is a compound as shown as formula 1 and the attendant definitions, wherein $R_1$, $R_3$, $R_5$, $R'_2$ and $R'_3$ are OH. In a further embodiment, the compound is a compound as shown as formula 1 and the attendant definitions, wherein $R_2$ and $R'_2$ are OH; $R_4$ is O-β-D-glucoside; and $R'_3$ is $OCH_3$. In a further embodiment, the compound is a compound as shown as formula 1 and the attendant definitions, wherein $R_2$ is OH; $R_4$ is O-β-D-glucoside; and $R'_3$ is $OCH_3$.

In a further embodiment, the compound is a compound as shown as formula 1 and the attendant definitions, wherein n is 0; A-B is ethenyl; and $R_1$, $R_2$, $R_3$, $R_4$, $R_5$, $R'_1$, $R'_2$, $R'_3$, $R'_4$, and $R'_5$ are H (trans stilbene). In a further embodiment, the compound is a compound as shown as formula 1 and the attendant definitions, wherein n is 1; A-B is ethenyl; M is O; and $R_1$, $R_2$, $R_3$, $R_4$, $R_5$, $R'_1$, $R'_2$, $R'_3$, $R'_4$, and $R'_5$ are H (chalcone). In a further embodiment, the compound is a compound as shown as formula 1 and the attendant definitions, wherein n is 0; A-B is ethenyl; $R_2$, $R_4$, and $R'_3$ are OH; and $R_1$, $R_3$, $R_5$, $R'_1$, $R'_2$, $R'_4$, and $R'_5$ are H (resveratrol). In a further embodiment, the compound is a compound as shown as formula 1 and the attendant definitions, wherein n is 0; A-B is ethenyl; $R_2$, $R_4$, $R'_2$ and $R'_3$ are OH; and $R_1$, $R_3$, $R_5$, $R'_1$, $R'_4$ and $R'_5$ are H (piceatannol). In a further embodiment, the compound is a compound as shown as formula 1 and the attendant definitions, wherein n is 1; A-B is ethenyl; M is O; $R_3$, $R_5$, $R'_2$ and $R'_3$ are OH; and $R_1$, $R_2$, $R_4$, $R'_1$, $R'_4$, and $R'_5$ are H (butein). In a further embodiment, the compound is a compound as shown as formula 1 and the attendant definitions, wherein n is 1; A-B is ethenyl; M is O; $R_1$, $R_3$, $R_5$, $R'_2$ and $R'_3$ are OH; and $R_2$, $R_4$, $R'_1$, $R'_4$, and $R'_5$ are H (3,4,2',4',6'-pentahydroxychalcone). In a further embodiment, the compound is a compound as shown as formula 1 and the attendant definitions, wherein n is 0; A-B is ethenyl; $R_2$ and $R'_2$ are OH, $R_4$ is O-β-D-glucoside, $R'_3$ is $OCH_3$; and $R_1$, $R_3$, $R_5$, $R'_1$, $R'_4$, and $R'_5$ are H (rhapontin). In a further embodiment, the compound is a compound as shown as formula 1 and the attendant definitions, wherein n is 0; A-B is ethenyl; $R_2$ is OH, $R_4$ is O-β-D-glucoside, $R'_3$ is $OCH_3$; and $R_1$, $R_3$, $R_5$, $R'_1$, $R'_2$, $R'_4$, and $R'_5$ are H (deoxyrhapontin). In a further embodiment, a compound is a compound as shown as formula 1 and the attendant definitions, wherein n is 0; A-B is —$CH_2CH(Me)CH(Me)CH_2$—; $R_2$, $R_3$, $R'_2$, and $R'_3$ are OH; and $R_1$, $R_4$, $R_5$, $R'_1$, $R'_4$, and $R'_5$ are H (NDGA).

In another embodiment, a sirtuin-activating compound is a flavanone compound of formula 2:

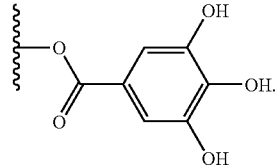

wherein, independently for each occurrence, $R_1$, $R_2$, $R_3$, $R_4$, $R_5$, $R'_1$, $R'_2$, $R'_3$, $R'_4$, $R'_5$, and R" represent H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

X represents CR or N; and

Y represents CR or N.

In a further embodiment, the compound is a compound as shown as formula 2 and the attendant definitions, wherein X and Y are both CH. In a further embodiment, the compound is a compound as shown as formula 2 and the attendant definitions, wherein M is O. In a further embodiment, the compound is a compound as shown as formula 2 and the attendant definitions, wherein M is $H_2$. In a further embodiment, the compound is a compound as shown as formula 2 and the attendant definitions, wherein Z is O. In a further embodiment, the compound is a compound as shown as formula 2 and the attendant definitions, wherein R" is H. In a further embodiment, the compound is a compound as shown as formula 2 and the attendant definitions, wherein R" is OH. In a further embodiment, the compound is a compound as shown as formula 2 and the attendant definitions, wherein R" is an ester. In a further embodiment, the compound is a compound as shown as formula 2 and the attendant definitions, wherein $R_1$ is

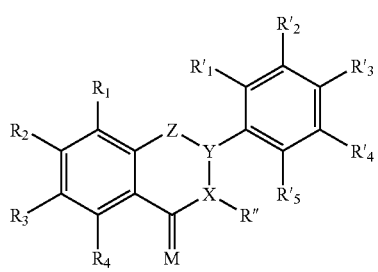

In a further embodiment, the compound is a compound as shown as formula 2 and the attendant definitions, wherein $R_1$, $R_2$, $R_3$, $R_4$, $R'_1$, $R'_2$, $R'_3$, $R'_4$, $R'_5$ and R" are H. In a further embodiment, the compound is a compound as shown as formula 2 and the attendant definitions, wherein $R_2$, $R_4$, and $R'_3$ are OH. In a further embodiment, the compound is a compound as shown as formula 2 and the attendant definitions, wherein $R_4$, $R'_2$, $R'_3$, and R" are OH. In a further embodiment, the compound is a compound as shown as formula 2 and the attendant definitions, wherein $R_2$, $R_4$, $R'_2$, $R'_3$, and R" are OH. In a further embodiment, the compound is a compound as shown as formula 2 and the attendant definitions, wherein $R_2$, $R_4$, $R'_2$, $R'_3$, $R'_4$, and R" are OH.

In a further embodiment, the compound is a compound as shown as formula 2 and the attendant definitions, wherein X and Y are CH; M is O; Z and O; R" is H; and $R_1$, $R_2$, $R_3$, $R_4$, $R'_1$, $R'_2$, $R'_3$, $R'_4$, $R'_5$ and R" are H (flavanone). In a further embodiment, the compound is a compound as shown as formula 2 and the attendant definitions, wherein X and Y are CH; M is O; Z and O; R" is H; $R_2$, $R_4$, and $R'_3$ are OH; and $R_1$, $R_3$, $R'_1$, $R'_2$, $R'_4$, and $R'_5$ are H (naringenin). In a further embodiment, the compound is a compound as shown as formula 2 and the attendant definitions, wherein X and Y are CH; M is O; Z and O; R" is OH; $R_2$, $R_4$, $R'_2$, and $R'_3$ are OH; and $R_1$, $R_3$, $R'_1$, $R'_4$, and $R'_5$ are H (3,5,7,3',4'-pentahydroxyflavanone). In a further embodiment, the compound is a compound as shown as formula 2 and the attendant definitions, wherein X and Y are CH; M is $H_2$; Z and O; R" is OH; $R_2$, $R_4$, $R'_2$, and $R'_3$, are OH; and $R_1$, $R_3$, $R'_1$, $R'_4$ and $R'_5$ are H (epicatechin). In a further embodiment, the compound is a compound as shown as formula 2 and the attendant definitions, wherein X and Y are CH; M is $H_2$; Z and O; R" is OH; $R_2$, $R_4$, $R'_2$, $R'_3$, and $R'_4$ are OH; and $R_1$, $R_3$, $R'_1$, and $R'_5$ are H (gallocatechin). In a further embodiment, the compound is a compound as shown as formula 2 and the attendant definitions, wherein X and Y are CH; M is $H_2$; Z and O; R" is

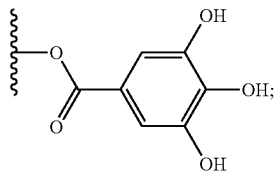

$R_2$, $R_4$, $R'_2$, $R'_3$, $R'_4$, and R" are OH; and $R_1$, $R_3$, $R'_1$, and $R'_5$ are H (epigallocatechin gallate).

In another embodiment, a sirtuin-activating compound is an iso flavanone compound of formula 3:

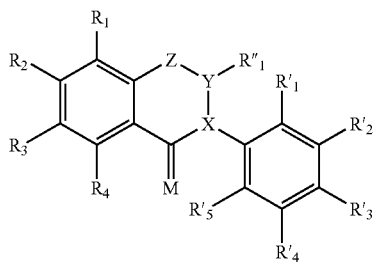

wherein, independently for each occurrence, $R_1$, $R_2$, $R_3$, $R_4$, $R_5$, $R'_1$, $R'_2$, $R'_3$, $R'_4$, $R'_5$, and $R''_1$ represent H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

X represents CR or N; and

Y represents CR or N.

In another embodiment, a sirtuin-activating compound is a flavone compound of formula 4:

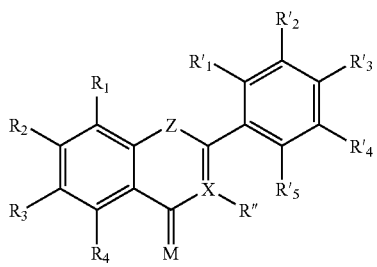

wherein, independently for each occurrence, $R_1$, $R_2$, $R_3$, $R_4$, $R_5$, $R'_1$, $R'_2$, $R'_3$, $R'_4$, and $R'_5$, represent H, alkyl, aryl, heteroaryl, alkaryl, heteroaralkyl, halide, $NO_2$, SR, OR, $N(R)_2$, or carboxyl;

R" is absent or represents H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

X represents CR or N when R" is absent or C when R" is present.

In a further embodiment, the compound is a compound as shown as formula 4 and the attendant definitions, wherein X is C. In a further embodiment, the compound is a compound as shown as formula 4 and the attendant definitions, wherein X is CR. In a further embodiment, the compound is a compound as shown as formula 4 and the attendant definitions, wherein Z is O. In a further embodiment, the compound is a compound as shown as formula 4 and the attendant definitions, wherein M is O. In a further embodiment, the compound is a compound as shown as formula 4 and the attendant definitions, wherein R" is H. In a further embodiment, the compound is a compound as shown as formula 4 and the attendant definitions, wherein R" is OH. In a further embodiment, the compound is a compound as shown as formula 4 and the attendant definitions, wherein $R_1$, $R_2$, $R_3$, $R_4$, $R_5$, $R'_1$, $R'_2$, $R'_3$, $R'_4$, and $R'_5$ are H. In a further embodiment, the compound of formula 4 and the attendant definitions, wherein $R_2$, $R'_2$, and $R'_3$ are OH. In a further embodiment, the compound is a compound as shown as formula 4 and the attendant definitions, wherein $R_2$, $R_4$, $R'_2$, $R'_3$, and $R'_4$ are OH. In a further embodiment, the compound is a compound as shown as formula 4 and the attendant definitions, wherein $R_2$, $R_4$, $R'_2$, and $R'_3$ are OH. In a further embodiment, the compound is a compound as shown as formula 4 and the attendant definitions, wherein $R_3$, $R'_2$, and $R'_3$ are OH. In a further embodiment, the compound is a compound as shown as formula 4 and the attendant definitions, wherein $R_2$, $R_4$, $R'_2$, and $R'_3$ are OH. In a further embodiment, the compound is a compound as shown as formula 4 and the attendant definitions, wherein $R_2$, $R'_2$, $R'_3$, and $R'_4$ are OH. In a further embodiment, the compound is a compound as shown as formula 4 and the attendant definitions, wherein $R_2$, $R_4$, and $R'_3$ are OH. In a further embodiment, the compound is a compound as shown as formula 4 and the attendant definitions, wherein $R_2$, $R_3$, $R_4$, and $R'_3$ are OH. In a further embodiment, the compound is a compound as shown as formula 4 and the attendant definitions, wherein $R_2$, $R_4$, and $R'_3$ are OH. In a further embodiment, the compound is a compound as shown as formula 4 and the attendant definitions, wherein $R_3$, $R'_1$, and $R'_3$ are OH. In a further embodiment, the compound is a compound as shown as formula 4 and the attendant definitions, wherein $R_2$ and $R'_3$ are OH. In a further embodiment, the compound is a compound as shown as formula 4 and the attendant definitions, wherein $R_1$, $R_2$, $R'_2$, and $R'_3$ are OH. In a further embodiment, the compound is a compound as shown as formula 4 and the attendant definitions, wherein $R_3$, $R'_1$, and $R'_2$ are OH. In a further embodiment, the compound is a compound as shown as formula 4 and the attendant definitions, wherein $R'_3$ is OH. In a further embodiment, the compound is a compound as shown as formula 4 and the attendant definitions, wherein $R_4$ and $R'_3$ are OH. In a further embodiment, the compound is a compound as shown as formula 4 and the attendant definitions, wherein $R_2$ and $R_4$ are OH. In a further embodiment, the compound is a compound as shown as formula 4 and the attendant definitions, wherein $R_2$, $R_4$, $R'_1$, and $R'_3$ are OH. In a further embodiment, the compound is a compound as shown as formula 4 and the attendant definitions, wherein $R_4$ is OH. In a further embodiment, the compound is a compound as shown as formula 4 and the attendant definitions, wherein $R_2$, $R_4$, $R'_2$, $R'_3$, and $R'_4$ are OH. In a further embodiment, the compound is a compound as shown as formula 4 and the attendant definitions, wherein $R_2$, $R'_2$, $R'_3$, and $R'_4$ are OH. In a further embodiment, the compound is a compound as shown as formula 4 and the attendant definitions, wherein $R_1$, $R_2$, $R_4$, $R'_2$, and $R'_3$ are OH.

In a further embodiment, the compound is a compound as shown as formula 4 and the attendant definitions, wherein X is CH; R" is absent; Z is O; M is O; and $R_1$, $R_2$, $R_3$, $R_4$, $R_5$, $R'_1$, $R'_2$, $R'_3$, $R'_4$, and $R'_5$ are H (flavone). In a further embodiment, the compound is a compound as shown as formula 4 and the attendant definitions, wherein X is C; R" is OH; Z is O; M is O; $R_2$, $R'_2$, and $R'_3$ are OH; and $R_1$, $R_3$, $R_4$, $R'_1$, $R'_4$, and $R'_5$ are H (fisetin). In a further embodiment, the compound is a compound as shown as formula 4 and the attendant definitions, wherein X is CH; R" is absent; Z is O; M is O; $R_2$, $R_4$, $R'_2$, $R'_3$, and $R'_4$ are OH; and $R_1$, $R_3$, $R'_1$, and $R'_5$ are H (5,7,3',4',5'-pentahydroxyflavone). In a further embodiment, the compound is a compound as shown as formula 4 and the attendant definitions, wherein X is CH; R" is absent; Z is O; M is O; $R_2$, $R_4$, $R'_2$, and $R'_3$ are OH; and $R_1$, $R_3$, $R'_1$, $R'_4$, and $R'_5$ are H (luteolin). In a further embodiment, the compound is a compound as shown as formula 4 and the attendant definitions, wherein X is C, R" is OH; Z is O; M is O; $R_3$, $R'_2$, and $R'_3$ are OH; and $R_1$, $R_2$, $R_4$, $R'_1$ $R'_4$, and $R'_5$ are H (3,6,3',4'-tetrahydroxyflavone). In a further embodiment, the compound is a compound as shown as formula 4 and the attendant definitions, wherein X is C, R" is OH; Z is O; M is O; $R_2$, $R_4$, $R'_2$, and $R'_3$ are OH; and $R_1$, $R_3$, $R'_1$, $R'_4$, and $R'_5$ are H (quercetin). In a further embodiment, the compound is a compound as shown as formula 4 and the attendant definitions, wherein X is CH; R" is absent; Z is O; M is O; $R_2$, $R'_2$, $R'_3$, and $R'_4$ are OH; and $R_1$, $R_3$, $R_4$, $R'_1$, and $R'_5$ are H. In a further embodiment, the compound is a compound as shown as formula 4 and the attendant definitions, wherein X is C; R" is OH; Z is O; M is O; $R_2$, $R_4$, and $R'_3$ are OH; and $R_1$, $R_3$, $R'_1$, $R'_2$, $R'_4$, and $R'_5$ are H. In a further embodiment, the compound is a compound as shown as formula 4 and the attendant definitions, wherein X is CH; R" is absent; Z is O; M is O; $R_2$, $R_3$, $R_4$, and $R'_3$ are OH; and $R_1$, $R'_1$, $R'_2$, $R'_4$, and $R'_5$ are H. In a further embodiment, the compound is a compound as shown as formula 4 and the attendant definitions, wherein X is CH; R" is absent; Z is O; M is O; $R_2$, $R_4$, and $R'_3$ are OH; and $R_1$, $R_3$, $R'_1$, $R'_2$, $R'_4$, and $R'_5$ are H. In a further embodiment, the compound is a compound as shown as formula 4 and the attendant definitions, wherein X is C, R" is OH; Z is O; M is O; $R_3$, $R'_1$, and $R'_3$ are OH; and $R_1$, $R_2$, $R_4$, $R'_2$, $R'_4$, and $R'_5$ are H. In a further embodiment, the compound is a compound as shown as formula 4 and the attendant definitions, wherein X is CH; R" is absent; Z is O; M is O; $R_2$ and $R'_3$ are OH; and $R_1$, $R_3$, $R_4$, $R'_1$, $R'_2$, $R'_4$, and $R'_5$ are H. In a further embodiment, the compound is a compound as shown as formula 4 and the attendant definitions, wherein X is C, R" is OH; Z is O; M is O; $R_1$, $R_2$, $R'_2$, and $R'_3$ are OH; and $R_1$, $R_2$, $R_4$, $R'_3$, $R'_4$, and $R'_5$ are H. In a further embodiment, the compound is a compound as shown as formula 4 and the attendant definitions, wherein X is C; R" is OH; Z is O; M is O; $R_3$, $R'_1$, and $R'_2$ are OH; and $R_1$, $R_2$, $R_4$; $R'_3$, $R'_4$, and $R'_5$ are H. In a further embodiment, the compound is a compound as shown as formula 4 and the attendant definitions, wherein X is CH; R" is absent; Z is O; M is O; $R'_3$ is OH; and $R_1$, $R_2$, $R_3$, $R_4$, $R'_1$, $R'_2$, $R'_4$, and $R'_5$ are H. In a further embodiment, the compound is a compound as shown as formula 4 and the attendant definitions, wherein X is CH; R" is absent; Z is O; M is O; $R_4$ and $R'_3$ are OH; and $R_1$, $R_2$, $R_3$, $R'_1$, $R'_2$, $R'_4$, and $R'_5$ are H. In a further embodiment, the compound is a compound as shown as formula 4 and the attendant definitions, wherein X is CH; R" is absent; Z is O; M is O; $R_2$ and $R_4$ are OH; and $R_1$, $R_3$, $R'_1$, $R'_2$, $R'_3$, $R'_4$, and $R'_5$ are H. In a further embodiment, the compound is a compound as shown as formula 4 and the attendant definitions, wherein X is C; R" is OH; Z is O; M is O; $R_2$, $R_4$, $R'_1$, and $R'_3$ are OH; and $R_1$, $R_3$, $R'_2$, $R'_4$, and $R'_5$ are H. In a further embodiment, the compound is a compound as shown as formula 4 and the attendant definitions, wherein X is CH; R" is absent; Z is O; M is O; $R_4$ is OH; and $R_1$, $R_2$, $R_3$, $R'_1$, $R'_2$, $R'_3$, $R'_4$, and $R'_5$ are H. In a further embodiment, the compound is a compound as shown as formula 4 and the attendant definitions, wherein X is C; R" is OH; Z is O; M is O; $R_2$, $R_4$, $R'_2$, $R'_3$, and $R'_4$ are OH; and $R_1$, $R_3$, $R'_1$, and $R'_5$ are H. In a further embodiment, the compound is a compound as shown as formula 4 and the attendant definitions, wherein X is C; R" is OH; Z is O; M is O; $R_2$, $R'_2$, $R'_3$, and $R'_4$ are OH; and $R_1$, $R_3$, $R_4$, $R'_1$, and $R'_5$ are H. In a further embodiment, the compound is a compound as shown as formula 4 and the attendant definitions, wherein X is C; R" is OH; Z is O; M is O; $R_2$, $R'_2$, $R'_3$, and $R'_4$ are OH; and $R_1$, $R_3$, $R_4$, $R'_1$, and $R'_5$ are H. In a further embodiment, the compound is a compound as shown as formula 4 and the attendant definitions, wherein X is C; R" is OH; Z is O; M is O; $R_1$, $R_2$, $R_4$, $R'_2$, and $R'_3$ are OH; and $R_3$, $R'_1$, $R'_4$, and $R'_5$ are H.

In another embodiment, a sirtuin-activating compound is an iso flavone compound of formula 5:

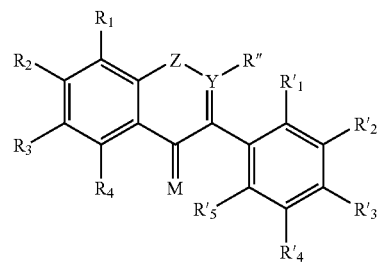

wherein, independently for each occurrence, $R_1$, $R_2$, $R_3$, $R_4$, $R_5$, $R'_1$, $R'_2$, $R'_3$, $R'_4$, and $R'_5$, represent H, alkyl, aryl, heteroaryl, alkaryl, heteroaralkyl, halide, $NO_2$, SR, OR, $N(R)_2$, or carboxyl;

R" is absent or represents H, alkyl, aryl, heteroaryl, alkaryl, heteroaralkyl, halide, $NO_2$, SR, OR, $N(R)_2$, or carboxyl;

R represents H, alkyl, or aryl;

M represents $H_2$, O, NR, or S;

Z represents CR, O, NR, or S; and

Y represents CR or N when R" is absent or C when R" is present.

In a further embodiment, the compound is a compound as shown as formula 5 and the attendant definitions, wherein Y is CR. In a further embodiment, the compound is a compound as shown as formula 5 and the attendant definitions, wherein Y is CH. In a further embodiment, the compound is a compound as shown as formula 5 and the attendant definitions, wherein Z is O. In a further embodiment, the compound is a compound as shown as formula 5 and the attendant definitions, wherein M is O. In a further embodiment, the compound is a compound as shown as formula 5 and the attendant definitions, wherein $R_2$ and $R'_3$ are OH. In a further embodiment, the compound of formula 5 and the attendant definitions, wherein $R_2$, $R_4$, and $R'_3$ are OH.

In a further embodiment, the compound is a compound as shown as formula 5 and the attendant definitions, wherein Y is CH; R" is absent; Z is O; M is O; $R_2$ and $R'_3$ are OH; and $R_1$, $R_3$, $R_4$, $R'_1$, $R'_2$, $R'_4$, and $R'_5$ are H. In a further embodiment, the compound is a compound as shown as formula 5 and the attendant definitions, wherein Y is CH; R" is absent; Z is O; M is O; $R_2$, $R_4$, and $R'_3$ are OH; and $R_1$, $R_3$, $R'_1$, $R'_2$, $R'_4$, and $R'_5$ are H.

In another embodiment, a sirtuin-activating compound is an anthocyanidin compound of formula 6:

$$6$$

wherein, independently for each occurrence, $R_3$, $R_4$, $R_5$, $R_6$, $R_7$, $R_8$, $R'_2$, $R'_3$, $R'_4$, $R'_5$, and $R'_6$ represent H, alkyl, aryl, heteroaryl, alkaryl, heteroaralkyl, halide, $NO_2$, SR, OR, $N(R)_2$, or carboxyl;

R represents H, alkyl, or aryl; and $A^-$ represents an anion selected from the following: $Cl^-$, $Br^-$, or $I^-$.

In a further embodiment, the compound is a compound as shown as formula 6 and the attendant definitions, wherein $A^-$ is $Cl^-$. In a further embodiment, the compound is a compound as shown as formula 6 and the attendant definitions, wherein $R_3$, $R_5$, $R_7$, and $R'_4$ are OH. In a further embodiment, the compound is a compound as shown as formula 6 and the attendant definitions, wherein $R_3$, $R_5$, $R_7$, $R'_3$, and $R'_4$ are OH. In a further embodiment, the compound is a compound as shown as formula 6 and the attendant definitions, wherein $R_3$, $R_5$, $R_7$, $R'_3$, $R'_4$, and $R'_5$ are OH.

In a further embodiment, the compound is a compound as shown as formula 6 and the attendant definitions, wherein $A^-$ is $Cl^-$; $R_3$, $R_5$, $R_7$, and $R'_4$ are OH; and $R_4$, $R_6$, $R_8$, $R'_2$, $R'_3$, $R'_5$, and $R'_6$ are H. In a further embodiment, the compound is a compound as shown as formula 6 and the attendant definitions, wherein $A^-$ is $Cl^-$; $R_3$, $R_5$, $R_7$, $R'_3$, and $R'_4$ are OH; and $R_4$, $R_6$, $R_8$, $R'_2$, $R'_5$, and $R'_6$ are H. In a further embodiment, the compound is a compound as shown as formula 6 and the attendant definitions, wherein $A^-$ is $Cl^-$; $R_3$, $R_5$, $R_7$, $R'_3$, $R'_4$, and $R'_5$ are OH; and $R_4$, $R_6$, $R_8$, $R'_2$, and $R'_6$ are H.

Methods for activating a sirtuin protein family member may also comprise contacting the cell with a stilbene, chalcone, or flavone compound represented by formula 7:

$$7$$

wherein, independently for each occurrence,

M is absent or O;

$R_1$, $R_2$, $R_3$, $R_4$, $R_5$, $R'_1$, $R'_2$, $R'_3$, $R'_4$, and $R'_5$ represent H, alkyl, aryl, heteroaryl, alkaryl, heteroaralkyl, halide, $NO_2$, SR, OR, $N(R)_2$, or carboxyl;

$R_a$ represents H or the two $R_a$ form a bond;

R represents H, alkyl, or aryl; and n is 0 or 1;

provided that when n is 0:

when $R_2$ and $R_4$ are OR, and $R_1$, $R_3$, $R_5$, $R'_1$, $R'_2$, $R'_4$, and $R'_5$ are H, $R'_3$ is not Cl, F, —$CH_3$, —$CH_2CH_3$, —SMe, $NO_2$, i-propyl, —OMe, or carboxyl;

when $R_3$ is OR at least one of $R'_1$, $R'_2$, $R'_3$, $R'_4$, or $R'_5$ is not H; and $R_4$ is not carboxyl.

In a further embodiment, the compound is a compound as shown as formula 7 and the attendant definitions, wherein n is 0. In a further embodiment, the compound is a compound as shown as formula 7 and the attendant definitions, wherein n is 1. In a further embodiment, the compound is a compound as shown as formula 7 and the attendant definitions, wherein M is absent. In a further embodiment, the compound is a compound as shown as formula 7 and the attendant definitions, wherein M is O. In a further embodiment, the compound is a compound as shown as formula 7 and the attendant definitions, wherein $R_a$ is H. In a further embodiment, the compound is a compound as shown as formula 7 and the attendant definitions, wherein M is O and the two $R_a$ form a bond.

In a further embodiment, the compound is a compound as shown as formula 7 and the attendant definitions, wherein $R_5$ is H. In a further embodiment, the compound is a compound as shown as formula 7 and the attendant definitions, wherein $R_5$ is OH. In a further embodiment, the compound is a compound as shown as formula 7 and the attendant definitions, wherein $R_1$, $R_3$, and $R'_3$ are OH. In a further embodiment, the compound is a compound as shown as formula 7 and the attendant definitions, wherein $R_2$, $R_4$, $R'_2$, and $R'_3$ are OH. In a further embodiment, the compound is a compound as shown as formula 7 and the attendant definitions, wherein $R_2$, $R'_2$, and $R'_3$ are OH. In a further embodiment, the compound is a compound as shown as formula 7 and the attendant definitions, wherein $R_2$ and $R_4$ are OH.

In a further embodiment, the compound is a compound as shown as formula 7 and the attendant definitions, wherein n is 0; M is absent; $R_a$ is H; $R_5$ is H; $R_1$, $R_3$, and $R'_3$ are OH; and $R_2$, $R_4$, $R'_1$, $R'_2$, $R'_4$, and $R'_5$ are H. In a further embodiment, the activating compound is a compound as shown as formula 7 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, the activating compound is a compound as shown as formula 7 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

Other sirtuin-activating compounds include compounds having a formula selected from the group consisting of formulas 8-10 set forth below.

$$8$$

R=H, alkyl, aryl, heterocyclyl, or heteroaryl
R'=H, halogen, NO$_2$, SR, OR, NR$_2$, alkyl, aryl, or carboxy

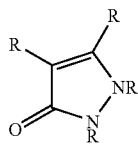

9

R=H, alkyl, aryl, heterocyclyl, or heteroaryl

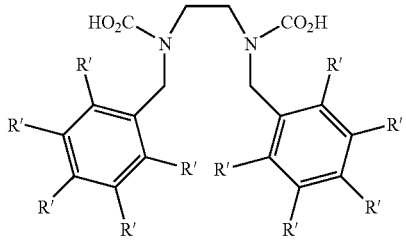

10 wherein, independently for each occurrence,
R'=H, halogen, NO$_2$, SR, OR, NR$_2$, alkyl, aryl, or carboxy
R=H, alkyl, aryl, heterocyclyl, or heteroaryl In another embodiment, exemplary sirtuin-activating compounds are isonicotinamide analogs, such as, for example, the isonicotinamide analogs described in U.S. Pat. Nos. 5,985,848; 6,066,722; 6,228,847; 6,492,347; 6,803,455; and U.S. Patent Publication Nos. 2001/0019823; 2002/0061898; 2002/0132783; 2003/0149261; 2003/0229033; 2003/0096830; 2004/0053944; 2004/0110772; and 2004/0181063, the disclosures of which are hereby incorporated by reference in their entirety. In an exemplary embodiment, sirtuin-activating compounds may be an isonicotinamide analog having any of formulas 11-14 below. In one embodiment, a sirtuin-activating compound is an isonicotinamide analog compound of formula 11:

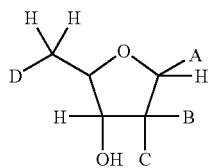

11

Wherein A is a nitrogen-, oxygen-, or sulfur-linked aryl, alkyl, cyclic, or heterocyclic group. The A moieties thus described, optionally have leaving group characteristics. In embodiments encompassed herein, A is further substituted with an electron contributing moiety. B and C are both hydrogen, or one of B or C is a halogen, amino, or thiol group and the other of B or C is hydrogen; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

In one example, A is a substituted N-linked aryl or heterocyclic group, an O-linked aryl or heterocyclic group having the formula —O—Y, or an S-linked aryl or heterocyclic group having the formula —O—Y; both B and C are hydrogen, or one of B or C is a halogen, amino, or thiol group and the other of B or C is hydrogen; and D is a primary alcohol or hydrogen. Nonlimiting preferred examples of A are set forth below, where each R is H or an electron-contributing moiety and Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl.

Examples of A include i-xiv below:

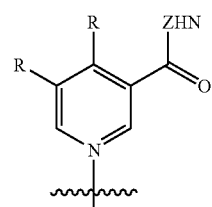

i

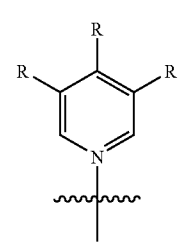

ii

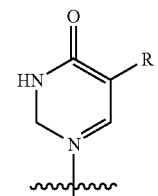

iii

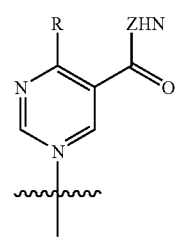

iv

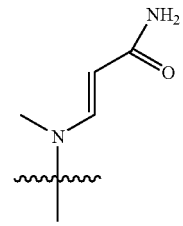

v

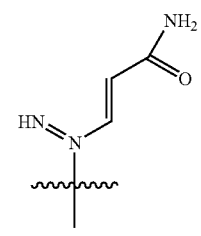

vi

-continued
vii 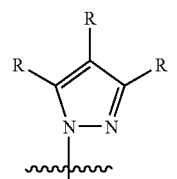
viii 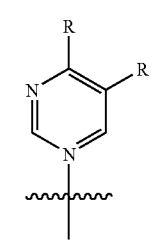
ix 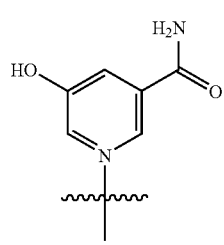
x 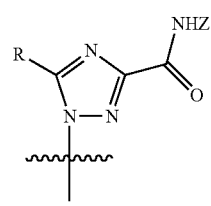
xi 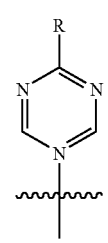
xii 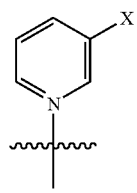
xiii 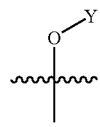
xiv 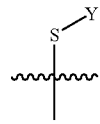
where Y=a group consistent with leaving group function.
Examples of Y include, but are not limited to, xv-xxvii below:
xv 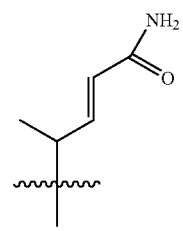
xvi 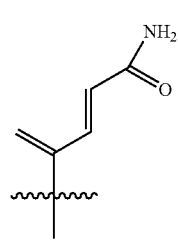
xvii 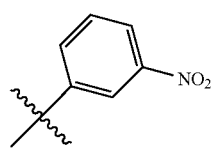
xviii 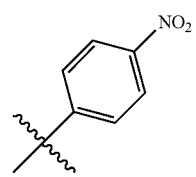
xix 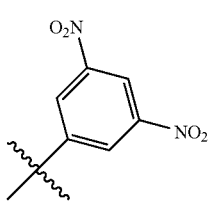
xx 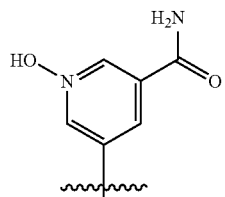
xxi 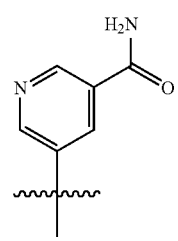

xxii
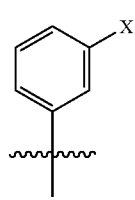

xxiii
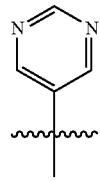

xxiv
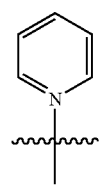

xxv
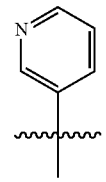

xxvi
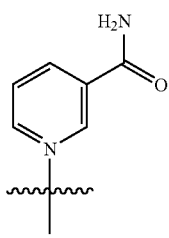

xxvii
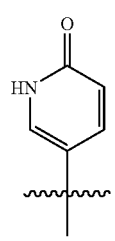

Wherein, for i-xxvii, X is halogen, thiol, or substituted thiol, amino or substituted amino, oxygen or substituted oxygen, or aryl or alkyl groups or heterocycles.

In certain embodiments, A is a substituted nicotinamide group (i above, where Z is H), a substituted pyrazolo group (vii above), or a substituted 3-carboxamid-imidazolo group (x above, where Z is H). Additionally, both B and C may be hydrogen, or one of B or C is a halogen, amino, or thiol group and the other of B or C is hydrogen; and D is a primary alcohol or hydrogen.

In other embodiments, one of B or C may be halogen, amino, or thiol group when the other of B or C is a hydrogen. Furthermore, D may be a hydrogen or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge. Analogues of adenosine monophosphate or adenosine diphosphate also can replace the adenosine monophosphate or adenosine diphosphate groups.

In some embodiments, A has two or more electron contributing moieties.

In other embodiments, a sirtuin-activating compound is an isonicotinamide analog compound of formulas 12, 13, or 14 below.

12
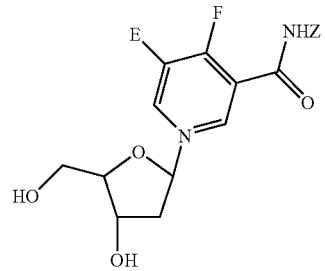

wherein Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl; E and F are independently H, $CH_3$, $OCH_3$, $CH_2CH_3$, $NH_2$, OH, NHCOH, $NHCOCH_3$, $N(CH_3)_2$, $C(CH_3)_2$, an aryl or a C3-C10 alkyl, preferably provided that, when one of E or F is H, the other of E or F is not H;

13
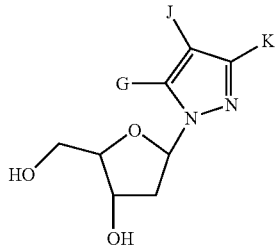

wherein G, J or K is CONHZ, Z is an alkyl, aryl, hydroxyl, OZ' where Z' is an alkyl or aryl, amino, NHZ' where Z' is an alkyl or aryl, or NHZ'Z" where Z' and Z" are independently an alkyl or aryl, and the other two of G, J and K is independently $CH_3$, $OCH_3$, $CH_2CH_3$, $NH_2$, OH, NHCOH, $NHCOCH_3$;

14
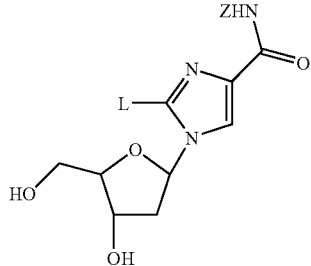

wherein Z is an alkyl, aryl, hydroxyl, OZ' where Z' is an alkyl or aryl, amino, NHZ' where Z' is an alkyl or aryl, or NHZ'Z"

where Z' and Z" are independently an alkyl or aryl; and L is CH₃, OCH₃, CH₂CH₃, NH₂, OH, NHCOH, NHCOCH₃.

In an exemplary embodiment, the compound is formula 12 above, wherein E and F are independently H, CH₃, OCH₃, or OH, preferably provided that, when one of E or F is H, the other of E or F is not H.

In another exemplary embodiment, the compound is β-1'-5-methyl-nicotinamide-2'-deoxyribose, β-D-1'-5-methyl-nico-tinamide-2'-deoxyribofuranoside, β-1'-4,5-dimethyl-nicotinamide-2'-de-oxyribose or β-D-1'-4,5-dimethyl-nicotinamide-2'-deoxyribofuranoside.

In yet another embodiment, the compound is β-1'-5-methyl-nicotinamide-2'-deoxyribose.

Without being bound to any particular mechanism, it is believed that the electron-contributing moiety on A stabilizes the compounds of the invention such that they are less susceptible to hydrolysis from the rest of the compound. This improved chemical stability improves the value of the compound, since it is available for action for longer periods of time in biological systems due to resistance to hydrolytic breakdown. The skilled artisan could envision many electron-contributing moieties that would be expected to serve this stabilizing function. Nonlimiting examples of suitable electron contributing moieties are methyl, ethyl, O-methyl, amino, NMe2, hydroxyl, CMe3, aryl and alkyl groups. Preferably, the electron-contributing moiety is a methyl, ethyl, O-methyl, amino group. In the most preferred embodiments, the electron-contributing moiety is a methyl group.

The compounds of formulas 11-14 are useful both in free form and in the form of salts. The term "pharmaceutically acceptable salts" is intended to apply to non-toxic salts derived from inorganic or organic acids and includes, for example, salts derived from the following acids: hydrochloric, sulfuric, phosphoric, acetic, lactic, fumaric, succinic, tartaric, gluconic, citric, methanesulfonic, and p-toluenesulfonic acids.

Also provided are compounds of formulas 11-14 that are the tautomers, pharmaceutically-acceptable salts, esters, and pro-drugs of the inhibitor compounds disclosed herein.

The biological availability of the compounds of formulas 11-14 can be enhanced by conversion into a pro-drug form. Such a pro-drug can have improved lipophilicity relative to the unconverted compound, and this can result in enhanced membrane permeability. One particularly useful form of pro-drug is an ester derivative. Its utility relies upon the action of one or more of the ubiquitous intracellular lipases to catalyse the hydrolysis of ester groups, to release the active compound at or near its site of action. In one form of pro-drug, one or more hydroxy groups in the compound can be O-acylated, to make an acylate derivative.

Pro-drug forms of a 5-phosphate ester derivative of compounds of formulas 11-14 can also be made. These may be particularly useful, since the anionic nature of the 5-phosphate may limit its ability to cross cellular membranes. Conveniently, such a 5-phosphate derivative can be converted to an uncharged bis(acyloxymethyl)ester derivative. The utility of such a pro-drug relies upon the action of one or more of the ubiquitous intracellular lipases to catalyse the hydrolysis of ester groups, releasing a molecule of formaldehyde and a compound of the present invention at or near its site of action. Specific examples of the utility of, and general methods for making, such acyloxymethyl ester pro-drug forms of phosphorylated carbohydrate derivatives have been described (Kang et al., 1998; Jiang et al., 1998; Li et al., 1997; Kruppa et al., 1997).

In another embodiment, exemplary sirtuin-activating compounds are O-acetyl-ADP-ribose analogs, including 2'-O-acetyl-ADP-ribose and 3'-O-acetyl-ADP-ribose, and analogs thereof. Exemplary O-acetyl-ADP-ribose analogs are described, for example, in U.S. Patent Publication Nos. 2004/0053944; 2002/0061898; and 2003/0149261, the disclosures of which are hereby incorporated by reference in their entirety. In an exemplary embodiment, sirtuin-activating compounds may be an O-acetyl-ADP-ribose analog having any of formulas 15-18 below. In one embodiment, a sirtuin-activating compound is an O-acetyl-ADP-ribose analog compound of formula 15:

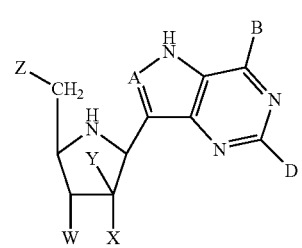

15 wherein:

A is selected from N, CH and CR, where R is selected from halogen, optionally substituted alkyl, aralkyl and aryl, OH, NH₂, NHR1, NR1R2 and SR3, where R1, R2 and R3 are each optionally substituted alkyl, aralkyl or aryl groups;

B is selected from OH, NH₂, NHR4, H and halogen, where R4 is an optionally substituted alkyl, aralkyl or aryl group;

D is selected from OH, NH₂, NHR5, H, halogen and SCH₃, where R5 is an optionally substituted alkyl, aralkyl or aryl group;

X and Y are independently selected from H, OH and halogen, with the proviso that when one of X and Y is hydroxy or halogen, the other is hydrogen;

Z is OH, or, when X is hydroxy, Z is selected from hydrogen, halogen, hydroxy, SQ and OQ, where Q is an optionally substituted alkyl, aralkyl or aryl group; and W is OH or H, with the proviso that when W is OH, then A is CR where R is as defined above;

or a tautomer thereof; or a pharmaceutically acceptable salt thereof; or an ester thereof; or a prodrug thereof.

In certain embodiments, when B is NHR4 and/or D is NHR5, then R4 and/or R5 are C1-C4 alkyl.

In other embodiments, when one or more halogens are present they are chosen from chlorine and fluorine.

In another embodiment, when Z is SQ or OQ, Q is C1-C5 alkyl or phenyl.

In an exemplary embodiment, D is H, or when D is other than H, B is OH.

In another embodiment, B is OH, D is H, OH or NH₂, X is OH or H, Y is H, most preferably with Z as OH, H, or methylthio, especially OH.

In certain embodiments W is OH, Y is H, X is OH, and A is CR where R is methyl or halogen, preferably fluorine.

In other embodiments, W is H, Y is H, X is OH and A is CH.

In other embodiments, a sirtuin-activating compound is an O-acetyl-ADP-ribose analog compound of formula 16:

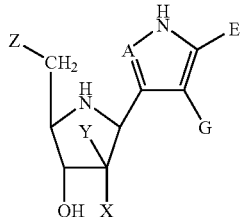

wherein A, X, Y, Z and R are defined for compounds of formula (15) where first shown above; E is chosen from CO2H or a corresponding salt form, CO$_2$R, CN, CONH$_2$, CONHR or CONR$_2$; and G is chosen from NH$_2$, NHCOR, NHCONHR or NHCSNHR; or a tautomer thereof, or a pharmaceutically acceptable salt thereof, or an ester thereof, or a prodrug thereof.

In certain embodiments, E is CONH$_2$ and G is NH$_2$.

In other embodiments, E is CONH$_2$, G is NH$_2$, X is OH or H, is H, most preferable with Z as OH, H or methylthio, especially OH.

Exemplary sirtuin-activating compounds include the following:
(1S)-1,4-dideoxy-1-C-(4-hydroxypyrrolo[3,2-d]pyrimidin-7-yl)-1,4-imino-D-ribitol
(1S)-1-C-(2-amino-4-hydroxypyrrolo[3,2-d]pyrimidin-7-yl)-1,4-dideoxy-1,4-imino-D-ribitol
(1R)-1-C-(4-hydroxypyrrolo[3,2-d]pyrimidin-7-yl)-1,4-imino-1,2,4-trideoxy-D-erythro-pentitol
(1S)-1-C-(4-hydroxypyrrolo[3,2-d]pyrimidin-7-yl)-1,4-imino-1,4,5-trideoxy-D-ribitol
(1S)-1,4-dideoxy-1-C-(4-hydroxypyrrolo[3,2-d]pyrimidin-7-yl)-1,4-imino-5-methylthio-D-ribitol
(1S)-1,4-dideoxy-1-C-(2,4-dihydroxypyrrolo[3,2-d]pyrimidin-7-yl)-1,4-imino-D-ribitol
(1R)-1-C-(2,4-dihydroxypyrrolo[3,2-d]pyrimidin-7-yl)-1,4-imino-1,2,4-trideoxy-D-erthro-pentitol
(1S)-1-C-(2,4-dihydroxypyrrolo[3,2-d]pyrimidin-7-yl)-1,4-imino-1,4,5-trideoxy-D-ribitol
(1S)-1,4-dideoxy-1-C-(2,4-dihydroxypyrrolo[3,2-d]pyrimidin-7-yl)-1,4-imino-5-ethylthio-D-ribitol
(1R)-1-C-(2-amino-4-hydroxypyrrolo[3,2-d]pyrimidin-7-yl)-1,4-imino-1,2,4-trideoxy-D-erythro-pentitol
(1S)-1-C-(2-amino-4-hydroxypyrrolo[3,2-d]pyrimidin-7-yl)-1,4-imino-1,4,5-trideoxy-D-ribitol
(1S)-1-C-(2-amino-4-hydroxypyrrolo[3,2-d]pyrimidin-7-yl)-1,4-dideoxy-1,4-imino-5-methylthio-D-ribitol
(1S)-1,4-dideoxy-1-C-(7-hydroxypyrazolo[4,3-d]pyrimidin-3-yl)-1,4-imino-D-ribitol
(1R)-1-C-(7-hydroxypyrazolo[4,3-d]pyrimidin-3-yl)-1,4-imino-1,2,4-trideoxy-D-erythro-pentitol
(1S)-1-C-(7-hydroxypyrazolo[4,3-d]pyrimidin-3-yl)-1,4-imino-1,4,5-trideoxy-D-ribitol
(1S)-1,4-dideoxy-1-C-(7-hydroxypyrazolo[4,3-d]pyrimidin-3-yl)-1,4-imino-5-ethylthio-D-ribitol
(1S)-1,4-dideoxy-1-C-(5,7-dihydroxypyrazolo[4,3-d]pyrimidin-3-yl)-1,4-imino-D-ribitol
(1R)-1-C-(5,7-dihydroxypyrazolo[4,3-d]pyrimidin-3-yl)-1,4-imino-1,2,4-trideoxy-D-erythro-pentitol
(1S)-1-C-(5,7-dihydroxypyrazolo[4,3-d]pyrimidin-3-yl)-1,4-imino-1,4,5-trideoxy-D-ribitol
(1S)-1,4-dideoxy-1-C-(5,7-dihydroxypyrazolo[4,3-d]pyrimidin-3-yl)-1,4-imino-5-methylthio-D-ribitol
(1S)-1-C-(5-amino-7-hydroxypyrazolo[4,3-d]pyrimidin-3-yl)-1,4-dideoxy-1,4-imino-D-ribitol
(1R)-1-C-(S-amino-7-hydroxypyrazolo[4,3-d]pyrimidin-3-yl)-1,4-imino-1,2,4-trideoxy-D-erythro-pentitol
(1S)-1-C-(5-amino-7-hydroxypyrazolo[4,3-d]pyrimidin-3-yl)-1,4-imino-1,4,5-trideoxy-D-ribitol
(1S)-1-C-(5-amino-7-hydroxypyrazolo[4,3-d]pyrimidin-3-yl)-1,4-dideoxy-1,4-imino-5-methylthio-D-ribitol
(1S)-1-C-(3-amino-2-carboxamido-4-pyrroly)-1,4-dideoxy-1,4-imino-D-ribitol.
(1S)-1,4-dideoxy-1-C-(4-hydroxypyrrolo[3,2-d]pyrimidin-7-yl)-1,4-imino-D-ribitol 5-phosphate
(1S)-1-C-(2-amino-4-hydroxypyrrolo[3,2-d]pyrimidin-7-yl)-1,4-imino-D-ribitol 5-phosphate
(1S)-1-C-(3-amino-2-carboxamido-4-pyrrolyl)-1,4-dideoxy-1,4-imino-D-ribitol In yet other embodiments, sirtuin-activating compounds are O-acetyl-ADP-ribose analog compounds of formula 17 and 18, their tautomers and pharmaceutically acceptable salts.

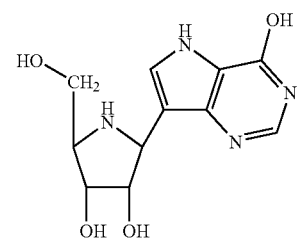

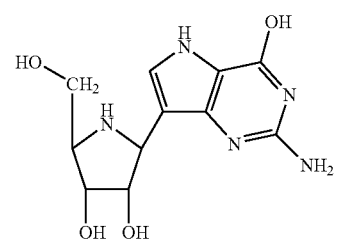

The biological availability of a compound of formula (15) or formula (16) can be enhanced by conversion into a prodrug form. Such a pro-drug can have improved lipophilicity relative to the compound of formula (15) or formula (16), and this can result in enhanced membrane permeability. One particularly useful form of a pro-drug is an ester derivative. Its utility relies upon the action of one or more of the ubiquitous intracellular lipases to catalyse the hydrolysis of these ester group(s), to release the compound of formula (15) and formula (16) at or near its site of action.

In one form of a prodrug, one or more of the hydroxy groups in a compound of formula (15) or formula (16) can be O-acylated, to make, for example a 5-O-butyrate or a 2,3-di-O-butyrate derivative.

Prodrug forms of 5-phosphate ester derivative of a compounds of formula (15) or formula (16) can also be made and may be particularly useful, since the anionic nature of the 5-phosphate may limit its ability to cross cellular membranes. Conveniently, such a 5-phosphate derivative can be converted to an uncharged bis(acyloxymethyl) ester derivative. The utility of such a pro-drug relies upon the action of one or more of the ubiquitous intracellular lipases to catalyse the hydrolysis of these ester group(s), releasing a molecule of formaldehyde and the compound of formula (15) or formula (16) at or near its site of action.

In an exemplary embodiment, analogs of 2'-AADPR or 3'-AADPR that are designed to have increased stability from esterase action through the use of well-known substitutes for ester oxygen atoms that are subject to esterase attack. The esterase-labile oxygen atoms in 2'-AADPR and 3'-AADPR would be understood to be the ester oxygen linking the acetate group with the ribose, and the ester oxygen between the two phosphorus atoms. As is known in the art, substitution of either or both of these ester oxygen atoms with a CF2, a NH, or a S would be expected to provide a 2'-AADPR or 3'-AADPR analog that is substantially more stable due to increased resistance to esterase action.

Thus, in some embodiments, the invention is directed to analogs 2'-O-acetyl-ADP-ribose or 3'-O-acetyl-ADP-ribose exhibiting increased stability in cells. The preferred analogs comprise a CF2, a NH, or a S instead of the acetyl ester oxygen or the oxygen between two phosphorus atoms. The most preferred substitute is CF2. Replacement of the acetyl ester oxygen is particularly preferred. In other preferred embodiments, both the ester oxygen and the oxygen between the two phosphorus atoms are independently substituted with a CF2, a NH, or a S.

Also included are pharmaceutically acceptable addition salts and complexes of the sirtuin-activating compounds of formulas 1-10. described herein. In cases wherein the compounds may have one or more chiral centers, unless specified, the compounds contemplated herein may be a single stereoisomer or racemic mixtures of stereoisomers.

In cases in which the sirtuin-activating compounds have unsaturated carbon-carbon double bonds, both the cis (Z) and trans (E) isomers are contemplated herein. In cases wherein the compounds may exist in tautomeric forms, such as keto-enol tautomers, such as

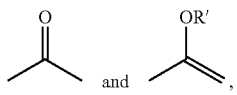

each tautomeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Also included in the methods presented herein are prodrugs of the sirtuin-activating compounds of formulas 1-10. described herein. Prodrugs are considered to be any covalently bonded carriers that release the active parent drug in vivo.

Analogs and derivatives of the above sirtuin-activating compounds described herein can also be used for activating a member of the sirtuin protein family. For example, derivatives or analogs may make the compounds more stable or improve their ability to traverse cell membranes or being phagocytosed or pinocytosed. Exemplary derivatives include glycosylated derivatives, as described, e.g., in U.S. Pat. No. 6,361,815 for resveratrol. Other derivatives of resveratrol include cis- and trans-resveratrol and conjugates thereof with a saccharide, such as to form a glucoside (see, e.g., U.S. Pat. No. 6,414,037). Glucoside polydatin, referred to as piceid or resveratrol 3-O-beta-D-glucopyranoside, can also be used. Saccharides to which compounds may be conjugated include glucose, galactose, maltose, lactose and sucrose. Glycosylated stilbenes are further described in Regev-Shoshani et al. Biochemical J. (published on Apr. 16, 2003 as BJ20030141). Other derivatives of compounds described herein are esters, amides and prodrugs. Esters of resveratrol are described, e.g., in U.S. Pat. No. 6,572,882. Resveratrol and derivatives thereof can be prepared as described in the art, e.g., in U.S. Pat. Nos. 6,414,037; 6,361,815; 6,270,780; 6,572,882; and Brandolini et al. (2002) J. Agric. Food. Chem. 50:7407. Derivatives of hydroxyflavones are described, e.g., in U.S. Pat. No. 4,591,600. Resveratrol and other activating compounds can also be obtained commercially, e.g., from Sigma.

In certain embodiments, if a sirtuin-activating compound occurs naturally, it may be at least partially isolated from its natural environment prior to use. For example, a plant polyphenol may be isolated from a plant and partially or significantly purified prior to use in the methods described herein. An activating compound may also be prepared synthetically, in which case it would be free of other compounds with which it is naturally associated. In an illustrative embodiment, an activating composition comprises, or an activating compound is associated with, less than about 50%, 10%, 1%, 0.1%, 10-2% or 10-3% of a compound with which it is naturally associated.

In certain embodiments, a certain biological function, e.g., reducing body weight, is modulated by any one of a sirtuin-activating compound of a genus of compounds (e.g., having formula I), with the proviso that the genus does not include one or more specific compounds. For example, in certain embodiments, a sirtuin activator-activating compound may be any compound that is capable of increasing the level of expression and/or activity of a sirtuin protein with the proviso that the compound is not resveratrol, a flavone, or any other compound specifically cited herein or any other compound that has been shown to have an activating effect on a sirtuin protein prior to the priority date of this application. In an exemplary embodiment, a sirtuin-activating compound may be a compound of any one of formulas 1-18 with the proviso that the compound is not resveratrol, a flavone or, or any of the other compounds specifically cited herein, or any other compound which has been shown to have an activating effect on a sirtuin protein prior to the priority date of this application. In an exemplary embodiment, a sirtuin-activating compound does not include any of the compounds cited in U.S. Pat. No. 6,410,596 or 6,552,085, the disclosures of which are hereby incorporated by reference in their entirety. For example, in one embodiment, a sirtuin-activating compound does not include a compound having formula 22 as set forth below:

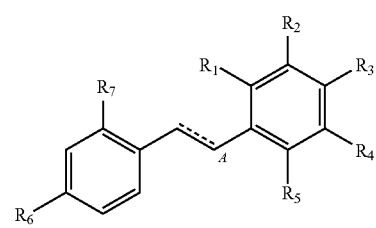

wherein,

A is selected from the group consisting of a single bond and a double bond in trans conformation;

R1 is selected from the group consisting of H, OH, C1-6 alkoxy, COOH, and COOC1-6 alkyl;

R2 is selected from the group consisting of H, OH, and C1-10 alkoxy;

R3 is selected from the group consisting of H, C1-10 alkyl, C2-10 alkenyl, C2-10 alkynyl, and C1-8 cycloalkyl;

R4 is selected from the group consisting of H, OH, and C1-10 alkoxy;

R5 are selected from the group consisting of H, C1-10 alkyl, C2-10 alkenyl, C2-10 alkynyl, and C1-8 cycloalkyl;

R6 is selected from the group consisting of H, OH, C1-6 alkoxy, COOH, and COOC1-6 alkyl;

R7 is selected from the group consisting of H, OH, C1-6 alkoxy, COOH, and COOC1-6 alkyl; and wherein at least one of R3 and R5 is selected from the group consisting of C1-10 alkyl, C2-10 alkenyl, C2-10 alkynyl; and C1-8 cycloalkyl;

In certain embodiments, the subject sirtuin activators, such as SIRT1 activators, do not have any substantial ability to inhibit PI3-kinase, inhibit aldoreductase and/or inhibit tyrosine protein kinases at concentrations (e.g., in vivo) effective for activating the deacetylase activity of the sirtuin, e.g., SIRT1. For instance, in preferred embodiments the sirtuin activator is chosen to have an EC50 for activating sirtuin deacetylase activity that is at least 5 fold less than the EC50 for inhibition of one or more of aldoreductase and/or tyrosine protein kinases, and even more preferably at least 10 fold, 100 fold or even 1000 fold less. Methods for assaying PI3-Kinase activity, aldose reductase activity, and tyrosine kinase activity are well known in the art and kits to perform such assays may be purchased commercially. See e.g., U.S. Patent Publication No. 2003/0158212 for PI3-kinase assays; U.S. Patent Publication No. 2002/20143017 for aldose reductase assays; tyrosine kinase assay k its may b e purchased commercially, for example, from Promega (Madison, Wis.; world wide web at promega.com), Invitrogen (Carlsbad, Calif.; world wide web at invitrogen.com) or Molecular Devices (Sunnyvale, Calif.; world wide web at moleculardevices.com).

In certain embodiments, the subject sirtuin activators do not have any substantial ability to transactivate EGFR tyrosine kinase activity at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for transactivating EGFR tyrosine kinase activity, and even more preferably at least 10 fold, 100 fold or even 1000 fold less. Methods for assaying transactivation of EGFR tyrosine kinase activity are well known in the art, see e.g., Pai et al. Nat. Med. 8: 289-93 (2002) and Vacca et al. Cancer Research 60: 5310-5317 (2000).

In certain embodiments, the subject sirtuin activators do not have any substantial ability to cause coronary dilation at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for coronary dilation, and even more preferably at least 10 fold, 100 fold or even 1000 fold less. Methods for assaying vasodilation are well known in the art, see e.g., U.S. Patent Publication No. 2004/0236153.

In certain embodiments, the subject sirtuin activators do not have any substantial spasmolytic activity at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for spasmolytic effects (such as on gastrointestinal muscle), and even more preferably at least 10 fold, 100 fold or even 1000 fold less. Methods for assaying spasmolytic activity are well known in the art, see e.g., U.S. Patent Publication No. 2004/0248987.

In certain embodiments, the subject sirtuin activators do not have any substantial ability to inhibit hepatic cytochrome P450 1B1 (CYP) at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for inhibition of P450 1B1, and even more preferably at least 10 fold, 100 fold or even 1000 fold less. Methods for assaying cytochrome P450 activity are well known in the art and kits to perform such assays may be purchased commercially. See e.g., U.S. Pat. Nos. 6,420,131 and 6,335,428 and Promega (Madison, Wis.; world wide web at promega.com).

In certain embodiments, the subject sirtuin activators do not have any substantial ability to inhibit nuclear factor-kappaB (NF-κB) at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for inhibition of NF-κB, and even more preferably at least 10 fold, 100 fold or even 1000 fold less. Methods for assaying NF-κB activity are well known in the art and kits to perform such assays may be purchased commercially (e.g., from Oxford Biomedical Research (Ann Arbor, Mich.; world wide web at oxfordbiomed.com)).

In certain embodiments, the subject sirtuin activators do not have any substantial ability to inhibit a histone deacetylase (HDACs) class I, a HDAC class II, or HDACs I and II, at concentrations (e.g., in vivo) effective for activating the deacetylase activity of the sirtuin. For instance, in preferred embodiments the sirtuin activator is chosen to have an EC50 for activating sirtuin deacetylase activity that is at least 5 fold less than the EC50 for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, the subject SIRT1 activators do not have any substantial ability to activate SIRT1 orthologs in lower eukaryotes, particularly yeast or human pathogens, at concentrations (e.g., in vivo) effective for activating the deacetylase activity of human SIRT1. For instance, in preferred embodiments the SIRT1 activator is chosen to have an EC50 for activating human SIRT1 deacetylase activity that is at least 5 fold less than the EC50 for activating yeast Sir2 (such as Candida, S. cerevisiae, etc.), and even more preferably at least 10 fold, 100 fold or even 1000 fold less.

In certain embodiments, the sirtuin activating compounds may have the ability to activate one or more sirtuin protein homologs, such as, for example, one or more of human SIRT1, SIRT2, SIRT3, SIRT4, SIRT5, SIRT6, or SIRT7. In other embodiments, a SIRT1 activator does not have any substantial ability to activate other sirtuin protein homologs, such as, for example, one or more of human SIRT2, SIRT3, SIRT4, SIRT5, SIRT6, or SIRT7, at concentrations (e.g., in vivo) effective for activating the deacetylase activity of human SIRT1. For instance, the SIRT1 activator may be chosen to have an EC50 for activating human SIRT1 deacetylase activity that is at least 5 fold less than the EC50 for activating one or more of human SIRT2, SIRT3, SIRT4, SIRT5, SIRT6, or SIRT7, and even more preferably at least 10 fold, 100 fold or even 1000 fold less.

In certain embodiments, SIRT3 and SIRT4 modulators may be used to modulate fat mobilization. For example, SIRT3 and/or SIRT4 activators may be used to induce fat mobilization and may be used to treat, e.g., obesity and insulin resistance disorders.

In other embodiments, the subject sirtuin activators do not have any substantial ability to inhibit protein kinases; to phosphorylate mitogen activated protein (MAP) kinases; to inhibit the catalytic or transcriptional activity of cyclo-oxygenases, such as COX-2; to inhibit nitric oxide synthase (iNOS); or to inhibit platelet adhesion to type I collagen at concentrations (e.g., in vivo) effective for activating the deacetylase activity of the sirtuin. For instance, in preferred embodiments, the sirtuin activator is chosen to have an EC50 for activating sirtuin deacetylase activity that is at least 5 fold less than the EC50 for performing any of these activities, and even more preferably at least 10 fold, 100 fold or even 1000 fold less. Methods for assaying protein kinase activity, cyclo-oxygenase activity, nitric oxide synthase activity, and platelet adhesion activity are well known in the art and kits to perform such assays may be purchased commercially. See e.g., Promega (Madison, Wis.; world wide web at promega.com), Invitrogen (Carlsbad, Calif.; world wide web at invitrogen.com); Molecular Devices (Sunnyvale, Calif.; world wide web at moleculardevices.com) or Assay Designs (Ann Arbor, Mich.; world wide web at assaydesigns.com) for protein kinase assay kits; Amersham Biosciences (Piscataway, N.J.; world wide web at amershambiosciences.com) for cyclo-oxygenase assay kits; Amersham Biosciences (Piscataway, N.J.; world wide web at amershambiosciences.com) and R&D Systems (Minneapolis, Minn.; world wide web at rndsystems.com) for nitric oxide synthase assay kits; and U.S. Pat. Nos. 5,321,010; 6,849,290; and 6,774,107 for platelet adhesion assays.

The sirtuin-activating compounds described herein may be taken alone or in combination with other compounds. The other compounds may be other sirtuin and/or AMPK activators. For example, Longevinex™, which is a red wine extract, and contains, in addition to resveratrol, other sirtuin activators, such as quercetin, is a particularly potent agent for mobilizing fat. Longevinex™ can be obtained on the world wide web at www.longevinex.com.

A combination drug regimen may also include drugs or compounds for the treatment or prevention of obesity and/or diabetes.

In an exemplary embodiment, sirtuin-activating compounds may be administered as a combination therapy. For example, for reducing weight, preventing weight gain, or treatment or prevention of obesity, one or more sirtuin-activating compounds of formulas 1-10 may be used in combination with the following "anti-obesity agents": phenylpropanolamine, ephedrine, pseudoephedrine, phentermine, a cholecystokinin-A agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (leptin), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Alternatively, one or more sirtuin-activating compounds of formulas 1-10 may be used in combination with the following "anti-diabetic agents": an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a peroxisome proliferator-activated receptor-γ (PPAR-γ) ligand such as troglitazone, rosaglitazone, pioglitazone or GW-1929, a sulfonylurea, glipazide, glyburide, or chlorpropamide wherein the amounts of the first and second compounds result in a therapeutic effect. Other anti-diabetic agents include a glucosidase inhibitor, a glucagon-like peptide-1 (GLP-1), insulin, a PPAR α/γ dual agonist, a megliti-mide and an αP2 inhibitor. In an exemplary embodiment, an anti-diabetic agent may be a dipeptidyl peptidase W (DP-IV or DPP-IV) inhibitor, such as, for example LAF237 from Novartis (NVP DPP728; 1-[[[2-[(5-cyanopyridin-2-yl)amino]ethyl]amino]acetyl]-2-cyano-(S)-pyrrolidine) or MK-04301 from Merck (see e.g., Hughes et al., Biochemistry 38: 11597-603 (1999)).

In certain embodiments, one or more sirtuin-activating compounds may be directed specifically to a certain tissue (e.g., liver) rather than the whole body. Tissue specific treatments may be used to treat, e.g., obesity and insulin resistance disorder.

In certain embodiments the methods are useful for preventing fat accumulation in cells with lipogenic capacity, e.g. liver, pancreas and muscle cells.

Methods for reducing or preventing fat accumulation in a cell may also comprise increasing the protein level of a sirtuin, such as SIRT1 in a human cell, Sir2 in a yeast cell, Sir2.1 in C. elegans or a homologue of any of these sirtuins in other organisms. Increasing protein levels can be achieved by introducing into a cell one or more copies of a nucleic acid that encodes a sirtuin. For example, the level of SIRT1 can be increased in a mammalian cell by introducing into the mammalian cell a nucleic acid encoding SIRT1, e.g., having the amino acid sequence set forth in SEQ ID NO: 2. The nucleic acid may be under the control of a promoter that regulates the expression of the SIRT1 nucleic acid. Alternatively, the nucleic acid may be introduced into the cell at a location in the genome that is downstream of a promoter. Methods for increasing the level of a protein using these methods are well known in the art. Exemplary methods are described in the Examples.

A nucleic acid that is introduced into a cell to increase the protein level of a sirtuin may encode a protein that is at least about 80%, 85%, 90%, 95%, 98%, or 99% identical to the sequence of a sirtuin, e.g., SEQ ID NO: 2. For example, the nucleic acid encoding the protein may be at least about 80%, 85%, 90%, 95%, 98%, or 99% identical to SEQ ID NO: 1. The nucleic acid may also be a nucleic acid that hybridizes, preferably under stringent hybridization conditions, to a nucleic acid encoding a wild-type sirtuin, e.g., SEQ ID NO: 1. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having SEQ ID NO: 2, preferably contains the core structure thereof. The core structure sometimes refers to amino acids 62-293 of SEQ ID NO: 2, which are encoded by nucleotides 237 to 932 of SEQ ID NO: 1, which encompasses the NAD binding as well as the substrate binding domains. The core domain of SIRT1 may also refer to about amino acids 261 to 447 of SEQ ID NO: 2, which are encoded by nucleotides 834 to 1394 of SEQ ID NO: 1; to about amino acids 242 to 493 of SEQ ID NO: 2, which are encoded by nucleotides 777 to 1532 of SEQ ID NO: 1; or to about amino acids 254 to 495 of SEQ ID NO: 2, which are encoded by nucleotides 813 to 1538 of SEQ ID NO: 1. Whether a protein retains a biological function, e.g., deacetylation capabilities, can be determined according to methods known in the art.

Methods for increasing sirtuin protein levels also include methods for stimulating the transcription of genes encoding sirtuins, methods for stabilizing the corresponding mRNAs, methods, and other methods known in the art.

Exemplary Sirtuin Inhibitory Compounds and Methods of Use

The Examples show that sirtuin inhibitory agents, such as nicotinamide, increase fat accumulation in C. elegans (See example 2).

Sirtuin inhibitory compounds include compounds that inhibit the activity of a class III histone deacetylase, such as a sirtuin, and include for example, nicotinamide (NAM), suranim; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin (hydroxy on sites 3,5,7,3',4',5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; and gossypetin (3,5,7,8,3',4'-hexahydroxyflavone), all of which are further described in Howitz et al. (2003) Nature 425:191. Other inhibitors, such as sirtinol and splitomicin, are described in Grozinger et al. (2001) *J. Biol. Chem.* 276:38837, Dedalov et al. (2001) *PNAS* 98:15113 and Hirao et al. (2003) *J. Biol. Chem* 278:52773. Analogs and derivatives of these compounds can also be used.

Yet other sirtuin inhibitory compounds may have any one of the following formulas:

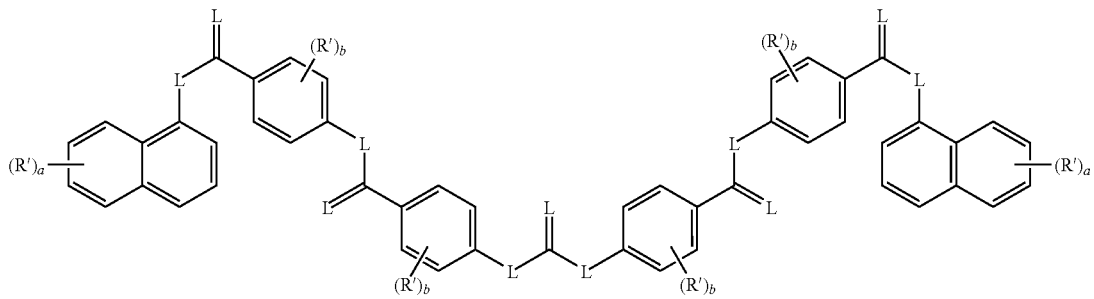

19 wherein, independently for each occurrence,
L represents O, NR, or S;
R represents H, alkyl, aryl, aralkyl, or heteroaralkyl;
R' represents H, halogen, NO2, SR, SO3, OR, NR2, alkyl, aryl, or carboxy;
a represents an integer from 1 to 7 inclusively; and
b represents an integer from 1 to 4 inclusively.

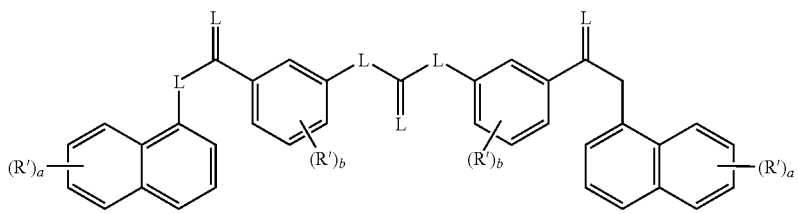

20 wherein, independently for each occurrence,
L represents O, NR, or S;
R represents H, alkyl, aryl, aralkyl, or heteroaralkyl;
R' represents H, halogen, NO2, SR, SO3, OR, NR2, alkyl, aryl, or carboxy;
a represents an integer from 1 to 7 inclusively; and
b represents an integer from 1 to 4 inclusively.

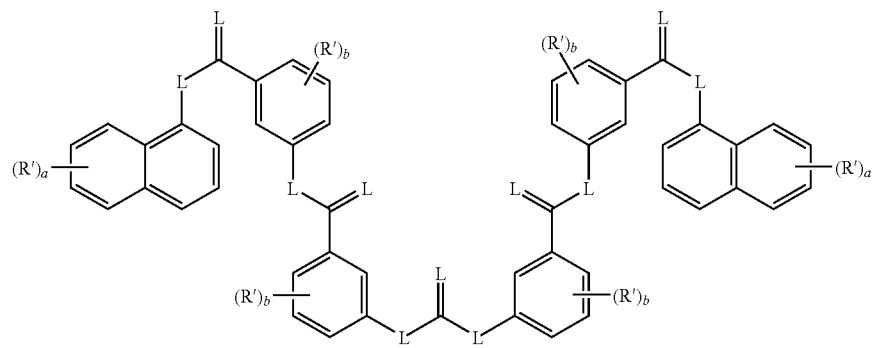

21 wherein, independently for each occurrence,

L represents O, NR, or S;

R represents H, alkyl, aryl, aralkyl, or heteroaralkyl;

R' represents H, halogen, NO₂, SR, SO3, OR, NR₂, alkyl, aryl, or carboxy;

a represents an integer from 1 to 7 inclusively; and b represents an integer from 1 to 4 inclusively.

Also included are pharmaceutically acceptable addition salts and complexes of the sirtuin inhibitory compounds of formulas 19-21 described herein. In cases wherein the compounds may have one or more chiral centers, unless specified, the compounds contemplated herein may be a single stereoisomer or racemic mixtures of stereoisomers.

In cases in which the sirtuin inhibitory compounds have unsaturated carbon-carbon double bonds, both the cis (Z) and trans (E) isomers are contemplated herein. In cases wherein the compounds may exist in tautomeric forms, such as keto-enol tautomers, such as

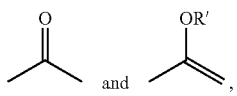

each tautomeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Also included in the methods presented herein are prodrugs of the sirtuin inhibitory compounds of formulas 19-21. Prodrugs are considered to be any covalently bonded carriers that release the active parent drug in vivo.

Whether in vitro or in vivo, a sirtuin inhibitory compound may also be contacted with a cell or administered either alone or in combination with other therapeutic agents. In one embodiment, more than one sirtuin inhibitory compound may be contacted with a cell or administered. For example, at least 2, 3, 5, or 10 different sirtuin inhibitory compounds may be contacted with a cell or administered. In another embodiment, a sirtuin inhibitory compound may be administered as part of a combination therapy with another therapeutic agent. Such combination therapies may be administered simultaneously (e.g., more than one therapeutic agent administered at the same time) or sequentially with e.g., different compounds or therapeutic agents administered at different times during a treatment regimen.

To promote weight gain, one or more sirtuin inhibitory compounds of formulas 19-21 may be used in combination with the following "weight gain promoting agents": beta blockers (such as propranolo), alpha blockers (such as clonidine, prazosin and terazosin); insulin, sulfonylureas (such as glipizide and glyburide), thiazolidinediones (such as pioglitazone and rosiglitazone), meglitinides, nateglinide, repaglinide, lithium carbonate, valproic acid, carbamazepine, antidepressants, including, for example, tricyclics (such as amitriptyline and imipramine), monoamine-oxidase inhibitors, selective serotonin reuptake inhibitors (SSRIs), bupropion, paroxetine and mirtazapine, chlorpromazine, thiothixene, steroids (such as prednisone), oral contraceptives (birth control pills) or other contraceptives containing estrogen and/or progesterone (Depo-Provera, Norplant, Ortho), testosterone or Megestrol.

In another embodiment, one or more sirtuin inhibitory compounds may be directed specifically to a certain tissue (e.g., liver) rather than the whole body. Tissue specific treatments may be used to treat, e.g., hyperglycemia.

Methods for stimulating fat accumulation in a cell may also comprise decreasing the protein level of a sirtuin in the cell. Decreasing a protein level can be achieved according to methods known in the art. For example, an siRNA, an antisense or ribozyme targeted to the sirtuin can be expressed in the cell. A dominant negative sirtuin mutant, e.g., a mutant that is not capable of deacetylating, may be used. For example, mutant H363Y of SIRT1, described, e.g., in Luo et al. (2001) Cell 107:137 can be used. Alternatively, agents that inhibit transcription can be used.

In other embodiments, a compound described herein, e.g., a sirtuin activator or inhibitor, does not have significant or detectable anti-oxidant activities, as determined by any of the standard assays known in the art. For example, a compound does not significantly scavenge free-radicals, such as O2 radicals. A compound may have less than about 2, 3, 5, 10, 30 or 100 fold anti-oxidant activity relative to another compound, e.g., resveratrol.

A compound may also have a binding affinity for a sirtuin of about $10^{-9}$M, $10^{-10}$M, $10^{-11}$M, $10^{-12}$M or less. A compound may reduce the Km of a sirtuin for its substrate or NAD+ by a factor of at least about 2, 3, 4, 5, 10, 20, 30, 50 or 100. A compound may increase the Vmax of a sirtuin by a factor of at least about 2, 3, 4, 5, 10, 20, 30, 50 or 100. Exemplary compounds that may increase the Vmax of a sirtuin include, for example, analogs of isonicotinamide, such as, for example, compounds of formulas 11-14, and/or analogs of O-acetyl-ADP-ribose, such as, for example, compounds of formulas 15-18. A compound may have an EC50 for activating the deacetylase activity of a sirtuin of less than about 1 nM, less than about 10 nM, less than about 100 nM, less than about 1 µM, less than about 10 µM, less than about 100 µM, or from about 1-10 nM, from about 10-100 nM, from about 0.1-1 µM, from about 1-10 µM or from about 10-100 µM. A compound may activate the deacetylase activity of a sirtuin by a factor of at least about 5, 10, 20, 30, 50, or 100, as measured in an acellular assay or in a cell based assay as described in the Examples. A compound may cause at least a 10%, 30%, 50%, 80%, 2 fold, 5 fold, 10 fold, 50 fold or 100 fold greater induction of the deacetylase activity of SIRT1 relative to the same concentration of resveratrol or other compound described herein. A compound may also have an EC50 for activating SIRT5 that is at least about 10 fold, 20 fold, 30 fold, 50 fold greater than that for activating SIRT1.

In an exemplary embodiment, the methods and compositions described herein may include a combination therapy comprising (i) at least one sirtuin-activating compound that reduce the Km of a sirtuin for its substrate or NAD+ by a factor of at least about 2, 3, 4, 5, 10, 20, 30, 50 or 100, and (ii) at least one sirtuin-activating compound that increases the Vmax of a sirtuin by a factor of at least about 2, 3, 4, 5, 10, 20, 30, 50 or 100. In one embodiment, a combination therapy may comprise (i) at least one sirtuin-activating compound of formula 1-10, and (ii) at least one sirtuin-activating compound of formula 11-18.

A compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to TNF-induced apoptosis.

The effect of a compound on the activity of a sirtuin, such as SIRT1, may be determined as described, e.g., in Howitz et al., supra or as follows. For instance, sirtuin proteins may be contacted with a compound in vitro, e.g., in a solution or in a cell. In one embodiment, a sirtuin protein is contacted with a compound in a solution and an activity of the sirtuin, e.g., its ability to deacetylate a protein, such as a histone or, p53, or portions thereof, is determined. Generally, a sirtuin is activated or inhibited by a compound when at least one of its biological activities, e.g., deacetylation activity, is higher or lower, respectively, in the presence of the compound than in its absence. Activation or inhibition may be by a factor of at least about 10%, 30%, 50%, 100% (i.e., a factor of two), 3, 10, 30, or 100.

Whether a sirtuin is activated or inhibited can be determined, e.g., by contacting the sirtuin or a cell or cell extract containing the sirtuin with a deacetylation target, such as a histone or, p53 protein, or portions thereof, and determining the level of acetylation of the deacetylation target. A higher level of acetylation of the target incubated with the sirtuin that is being tested relative to the level of acetylation of a control sirtuin indicates that the sirtuin that is being tested is activated. Conversely, a lower level of acetylation of the target incubated with the sirtuin that is being tested relative to the level of acetylation of a control sirtuin indicates that the sirtuin that is being tested is inhibited. The control sirtuin may be a recombinantly produced sirtuin that has not been contacted with a sirtuin-activating or -inhibiting compound.

Additional Exemplary Methods

Described herein are methods for treating or preventing obesity or generally weight gain, in a subject, such as to reduce the weight of the subject or reduce weight gain. A method may comprise administering to a subject, such as a subject in need thereof, a pharmaceutically effective amount of an agent that increases the activity or protein level of a sirtuin, such as SIRT1 or Sir2. A subject in need of such a treatment may be a subject who is obese, or likely to become obese, or who has, or is, likely to gain excess weight, as predicted, e.g., from family history. Exemplary agents are those described herein. A combination of agents may also be administered. A method may further comprise monitoring the weight of the subject and/or the level of activation of sirtuins, for example, in adipose tissue.

Also described herein are methods for treating or preventing a metabolic disorder, such as insulin-resistance or other precursor symptom of type II diabetes, type II diabetes or complications thereof. Methods may increase insulin sensitivity or decrease insulin levels in a subject. A method may comprise administering to a subject, such as a subject in need thereof, a pharmaceutically effective amount of an agent that increases the activity or protein level of a sirtuin, such as SIRT1 or Sir2. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy. Exemplary agents are those described herein.

A combination of agents may also be administered. A method may further comprise monitoring in the subject the state of any of these conditions and/or the level of activation of sirtuins, for example, in adipose tissue.

Other methods include administering to a subject of a combination of an agent that increases the activity or protein level of a sirtuin and an agent that increases the activity or protein level of an AMPK, e.g., other than an agent that activates a sirtuin. Activators of AMPK include AICAR or Metformin. Alternatively, the protein level of AMPK may be increased by introducing into the cell a nucleic acid encoding AMPK. The nucleotide sequence of the catalytic domain ($\alpha$1) of human AMPK has the nucleotide sequence set forth in GenBank Accession No. NM_206907 and encodes a protein having the amino acid sequence set forth in GenBank Accession No. NP_996790. The nucleotide sequence of the non-catalytic domain ($\beta$1) of human AMPK has the nucleotide sequence set forth in GenBank Accession No. NM_006253 and encodes a protein having the amino acid sequence set forth in GenBank Accession No. NP_006244. The nucleotide sequence of the non-catalytic domain ($\gamma$1) of human AMPK has the nucleotide sequence set forth in GenBank Accession No. NM_212461 and encodes a protein having the amino acid sequence sets forth in GenBank Accession No. NP_997626. To increase the protein level of human AMPK in a cell, it may be necessary to introduce nucleic acids encoding each of the subunits of the protein. Nucleic acid sequences encoding the different subunits may be contained on the same or separate nucleic acid molecules.

Other diseases that may be treated by administering an agent that increases the activity or protein level of a sirtuin and/or AMPK include certain renal diseases including glomerulonephritis, glomerulosclerosis, nephrotic syndrome, hypertensive nephrosclerosis. These compounds may also be useful for improving cognitive functions in dementia, treating diabetic complications, psoriasis, polycystic ovarian syndrome (PCOS) and prevention and treatment of bone loss, e.g. osteoporosis.

Additional diseases and conditions that will benefit from weight loss and can be treated as described herein include: high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Stunkard A J, Wadden T A. (Editors) Obesity: theory and therapy, Second Edition. New York: Raven Press, 1993. Finally, patients with AIDS can develop lipodystrophy or insulin resistance in response to combination therapies for AIDS. Accordingly, any of these conditions can be treated or prevented by the methods described herein for reducing or preventing weight gain.

Also provided herein are methods for stimulating weight gain. A method may comprise administering to a subject, such as a subject in need thereof, a pharmaceutically effective amount of an agent that decreases the activity or protein level of a sirtuin, such as SIRT1 or Sir2. A subject in need of such a treatment may be a subject who has cachexia or likely to develop cachexia. Exemplary agents are those described herein. A combination of agents may also be administered. A method may further comprise monitoring in the subject the state of the disease or of activation of sirtuins, for example, in adipose tissue.

Methods for stimulating fat accumulation in cells may be used in vitro, to establish cell models of weight gain, which may be used, e.g., for identifying other drugs that prevent weight gain.

A method for stimulating weight gain or fat accumulation in a cell or subject may further comprise decreasing the activity or protein level of an AMPK. This can be achieved, e.g., by inhibiting the expression, transcription, translation or post-translational modification of at least one of the three subunits of AMPK, such as the catalytic subunit. Techniques known in the art, such as RNAi, antisense and ribozyme can be used. In addition, dominant negative mutants may be expressed in the cell. Dominant negative mutants, such as having a mutated AMPK alpha subunit are described, e.g., in Minokoshi et al. (2004) Nature 428:569; Xing et al. (2003) J. Biol. Chem. 278:28372 and Woods et al. (2000) Mol. Cell Biol. 20:6704. Compounds that inhibit AMPK expression or activity may also be used. An exemplary compound is described in Thou et al. (2001) J. Clin. Invest. 108:1167.

Also provided herein are methods for modulating adipogenesis or fat cell differentiation, whether in vitro or in vivo. In particular, high circulating levels of insulin and/or insulin like growth factor (IGF) 1 will be prevented from recruiting preadipocytes to differentiate into adipocytes. Such methods may be used to modulate obesity. A method for inhibiting adipogenesis may comprise contacting a cell with an agent that increases the activity or protein level of a sirtuin, such as a sirtuin activating compound, e.g., a compound described herein. A method for stimulating adipogenesis may comprise contacting a cell with an agent that decreases the activity or protein level of a sirtuin, such as a sirtuin inhibiting compound, e.g., a compound described herein.

Based at least on the fact that resveratrol has been shown herein to activate AMPK, resveratrol and other sirtuin activating compounds may be used for treating or preventing conditions that can benefit from AMPK modulation, e.g., which are associated with and/or regulated by AMPK, in addition to those described above. Exemplary conditions include clinical symptoms associated with hypoxia or ischemia (myocardial infarction, stroke), and disorders of nutrition (see U.S. Pat. No. 6,124,125).

Similarly, any compound that activates AMPK may be used for the same purposes as sirtuin activating compounds may be used, e.g., to extend lifespan, to make cells more resistant to stress and to protect cells against apoptosis.

Other methods provided herein are methods for reducing appetite, or increasing satiety, thereby causing weight loss or avoidance of weight gain. Methods may include administrating to a subject, e.g., a subject in need thereof, an amount of a sirtuin activator or an agent that increases the protein level of a sirtuin in the subject. A subject in need of such a treatment may be a subject who is overweight, obese or a subject likely to become overweight or obese. The method may comprise administering daily, every other day, or once a week, a dose, e.g., in the form of a pill, to a subject. The dose may be an "appetite reducing dose." Such a dose may be, e.g., one pill of Longevinex™ daily.

Assays for determining the likelihood that a subject has or will develop weight gain, obesity, insulin resistance, diabetes or precursor symptoms or conditions resulting therefrom, are also provided. Such assays may comprise determining the level activity or expression (e.g., mRNA, pre-mRNA or protein) of a sirtuin, such as SIRT1, or AMPK in a subject. A low level of sirtuin activity or expression in a subject is likely to indicate that the subject has or is likely to develop weight gain, obesity, insulin resistance, diabetes, precursor symptoms thereof or secondary conditions thereof. Alternatively, a higher level of sirtuin activity or expression in a subject is likely to indicate that the subject has or is likely to develop weight loss and be protected from developing high weight associated diseases, such as insulin resistance and diabetes. Other assays include determining the activity or level of expression of a sirtuin and AMPK.

Also provided herein are methods for identifying compounds that modulate weight gain and/or treat or prevent insulin resistance (or sensitivity) or diabetes. A method may comprise identifying an agent that modulates the activity or protein level of a sirtuin and testing whether the test agent modulates weight gain and/or can be used for treating or preventing insulin resistance or diabetes. The first step of the method may comprise contacting a sirtuin with a test agent and determining the effect of the test agent on the activity of the sirtuin, e.g., SIRT1, as described, e.g., in Howitz et al., supra. The first step of the method may also comprise contacting a cell comprising a sirtuin with a test agent and determining the effect of the test agent on the activity of or expression level of the sirtuin. Expression levels of a sirtuin may be determined by measuring the mRNA, pre-mRNA or protein level of the sirtuin. The second step of the method may comprise testing the agent in an animal model for obesity, insulin resistance and/or diabetes. Such animal models are well known in the art. Screening methods may further comprise a step to determine the toxicity or adverse effects of the agents.

Other screening assays comprise identifying agents that modulate AMPK activity or protein levels. There is a need for compounds that activate AMPK but do not have the toxicities or adverse effects of known AMPK activators, such as metformin/phenformin.

Pharmaceutical Formulations and Administration Modes

Pharmaceutical compositions for use in accordance with the present methods may be formulated in conventional manner using one or more physiologically acceptable carriers or excipients. Thus, sirtuin-activating or -inhibiting compounds and their physiologically acceptable salts and solvates may be formulated for administration by, for example, injection, inhalation or insufflation (either through the mouth or the nose) or oral, buccal, parenteral or rectal administration. In one embodiment, the compound is administered locally, at the site where the target cells, e.g., fat cells, are present, i.e., in the adipose tissue.

Compounds can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

Polyphenols such as resveratrol can oxidize and lose sirtuin-stimulatory activity, especially in a liquid or semi-solid form. To prevent oxidation and preserve the sirtuin-stimulatory activity of polyphenol-containing compounds, the compounds may be stored in a nitrogen atmosphere or sealed in a type of capsule and/or foil package that excludes oxygen (e.g. Capsugel™).

For administration by inhalation, the compounds may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Controlled release formula also include patches.

Pharmaceutical compositions (including cosmetic preparations) may comprise from about 0.00001 to 100% such as from 0.001 to 10% or from 0.1% to 5% by weight of one or more compounds described herein.

In one embodiment, a compound described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, cited in the preceding section, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGS) of varying molecular weight; again, reference may be had to Remington's, supra, for further information.

Compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark AquaphorR™ from Beiersdorf, Inc. (Norwalk, Conn.).

Compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Compounds may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{10}$ MSO) and tetradecylmethyl sulfboxide; pyrrolidones such as 2-pyrrolidone, N-methyl-2-pyrrolidone and N-(hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark AzoneR™ from Whitby Research Incorporated, Richmond, Va.).

Examples of solubilizers include, but are not limited to, the following: hydrophilic ethers such as diethylene glycol monoethyl ether (ethoxydiglycol, available commercially as TranscutolR™) and diethylene glycol monoethyl ether oleate (available commercially as SoftcutolR™); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as LabrasolR™); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition as herein defined.

In an alternative embodiment, a pharmaceutical formulation is provided for oral or parenteral administration, in which case the formulation may comprise an activating compound-containing microemulsion as described above, and may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Administration of a sirtuin activator or inhibitor may be followed by measuring a factor in the subject, such as measuring the activity of the sirtuin. In an illustrative embodiment, a cell is obtained from a subject following administration of an activating or inhibiting compound to the subject, such as by obtaining a biopsy, and the activity of the sirtuin or sirtuin expression level is determined in the biopsy. Alternatively, biomarkers, such as plasma biomarkers may be followed. Biomarkers may be adipose cell derived secretory proteins, such as leptin, adiponectin, and resistin. The cell may be any cell of the subject, but in cases in which an activating compound is administered locally, the cell is preferably a cell that is located in the vicinity of the site of administration. The cell may be an adipocyte.

Other factors that may be monitored include weight, body mass, blood glucose sugar levels, blood lipid levels and any other factor that may be measured for monitoring diseases or conditions described herein.

Introduction and expression of a nucleic acid encoding a sirtuin, an AMPK or molecules that will reduced the protein level of a sirtuin or AMPK in a cell, e.g., an siRNA, may be accomplished using an expression vector. Exemplary expression vectors include adenoviral vectors or adenoviral-associated viruses (AAV). These vectors, as well as others and methods for infecting target cells are well known in the art. Alternatively, nucleic acids may also be introduced into cells using liposomes or similar technologies.

Kits

Also provided herein are kits, e.g., kits for therapeutic purposes, including kits for modulating fat accumulation. A kit may comprise one or more agent that modulates sirtuin or AMPK protein activity or level, e.g., sirtuin activating or inhibitory compounds, such as those described herein, and optionally devices for contacting cells with the agents. Devices include syringes, stents and other devices for introducing a compound into a subject or applying it to the skin of a subject.

Further, a kit may also contain components for measuring a factor, e.g., described above, such as the activity of sirtuin proteins, e.g., in tissue samples.

Other kits include kits for diagnosing the likelihood of having or developing weight gain, obesity, insulin-resistance, diabetes, precursors thereof or secondary conditions thereof. A kit may comprise an agent for measuring the activity and or expression level of a sirtuin or AMPK.

Kits for screening assays are also provided. Exemplary kits comprise one or more agents for conducting a screening assay, such as a sirtuin, an AMPK or a biologically active portion thereof, or a cell or cell extract comprising such. Any of the kits may also comprise instructions for use.

The present description is further illustrated by the following examples, which should not be construed as limiting in any way. The contents of all cited references (including literature references, issued patents, published patent applications and GenBank Accession numbers as cited throughout this application) are hereby expressly incorporated by reference.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide. Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory. Press, Cold Spring Harbor, N.Y., 1986).

EXAMPLES

Example 1

Resveratrol Promotes Fat Mobilization

This example shows that a compound that activates sirtuins, resveratrol, stimulates fat metabolism by reducing fat accumulation in *C. elegans*.

Wild-type N2 *C. elegans* worms were grown on OP50 bacteria and exposed overnight to vehicle (0.1% ethanol) alone or with 10, 50 or 100 µM of resveratrol (in ethanol). Fat accumulation was visualized with Nile Red staining, as described further below and in Ashrafi K, et al. Nature 421: 268-27 (2003).

The results, which are shown in FIG. 1, indicate that resveratrol treatment with 100 µM resulted in a 90% reduction of fat accumulation. Similarly, incubation of the worms in the presence of 10 µM or 50 µM of resveratrol showed a marked decrease in fat accumulation. The decrease in fat accumulation is as or more striking than treatments with AICAR, a know activator of AMPK and fatty acid oxidation.

Figure 2:
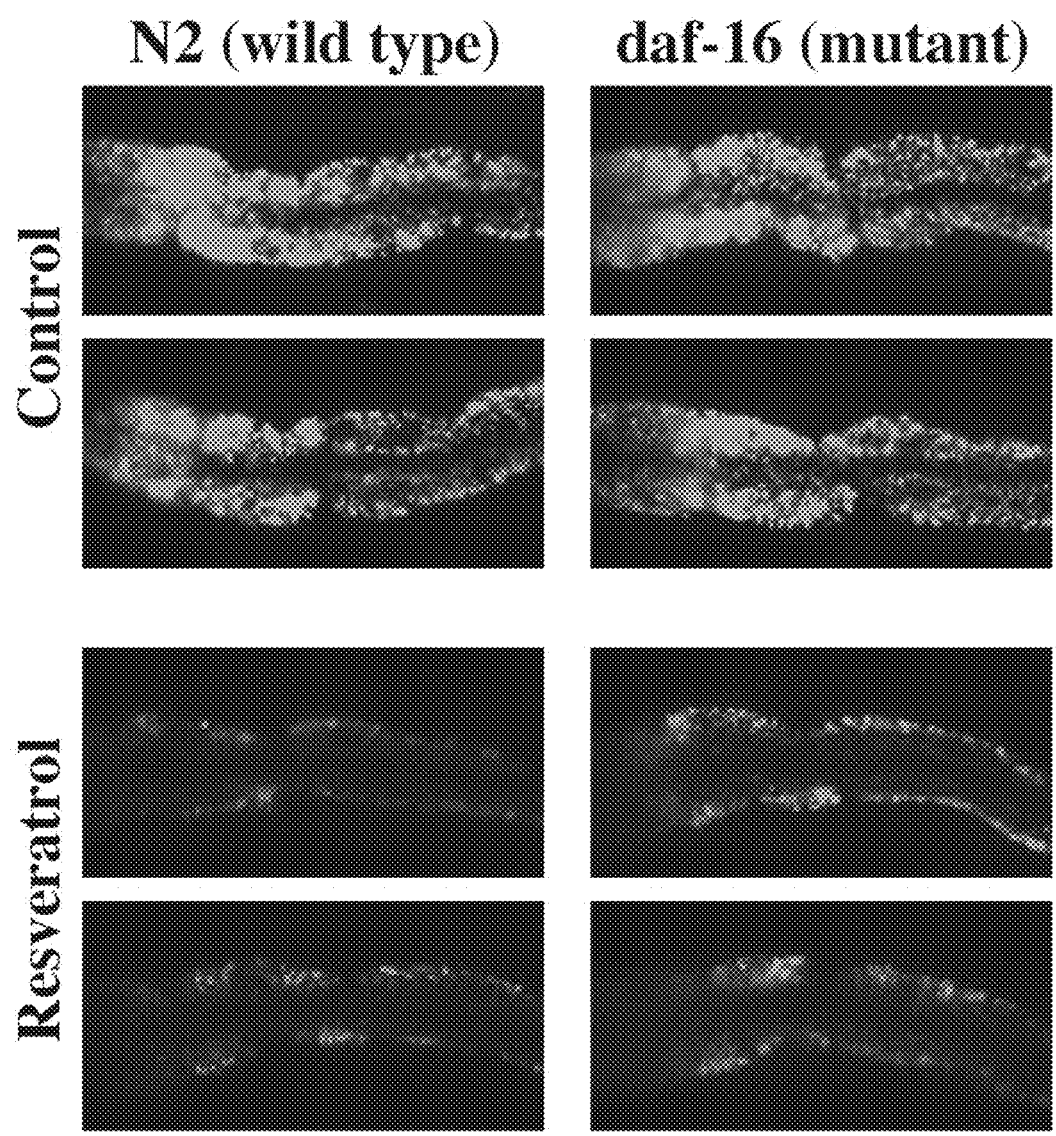
FIG. 2 is a series of photomicrographs that depict the effect of resveratrol to induce fat mobilization in a mutant worm with disrupted insulin signaling.

Sir2.1, which is activated by resveratrol, acts via the transcription factor DAF-16 to prolong lifespan in yeast (Tissenbaum and Guarente (2001) Nature 410:227). Similarly to the wild-type *C. elegans*, in DAF-16 mutant worms (mgDf47), which are defective in insulin-signaling (Wolkow, et al. Science 290:147, 2000), resveratrol stimulates fat mobilization and a decrease in fat accumulation (FIG. 2). This indicates that resveratrol signaling to fat metabolism in adult worms occurs via a pathway that is independent of DAF-16.

Accordingly, compounds in the resveratrol class that stimulate sirtuin proteins can promote fat mobilization in both wild-type and mutant *C. elegans*.

Example 2

Nicotinamide Promotes Fat Accumulation

If stimulators of sirtuin proteins decrease fat accumulation, inhibitors of sirtuin proteins, such as nicotinamide, should increase fat accumulation.

Figure 3:
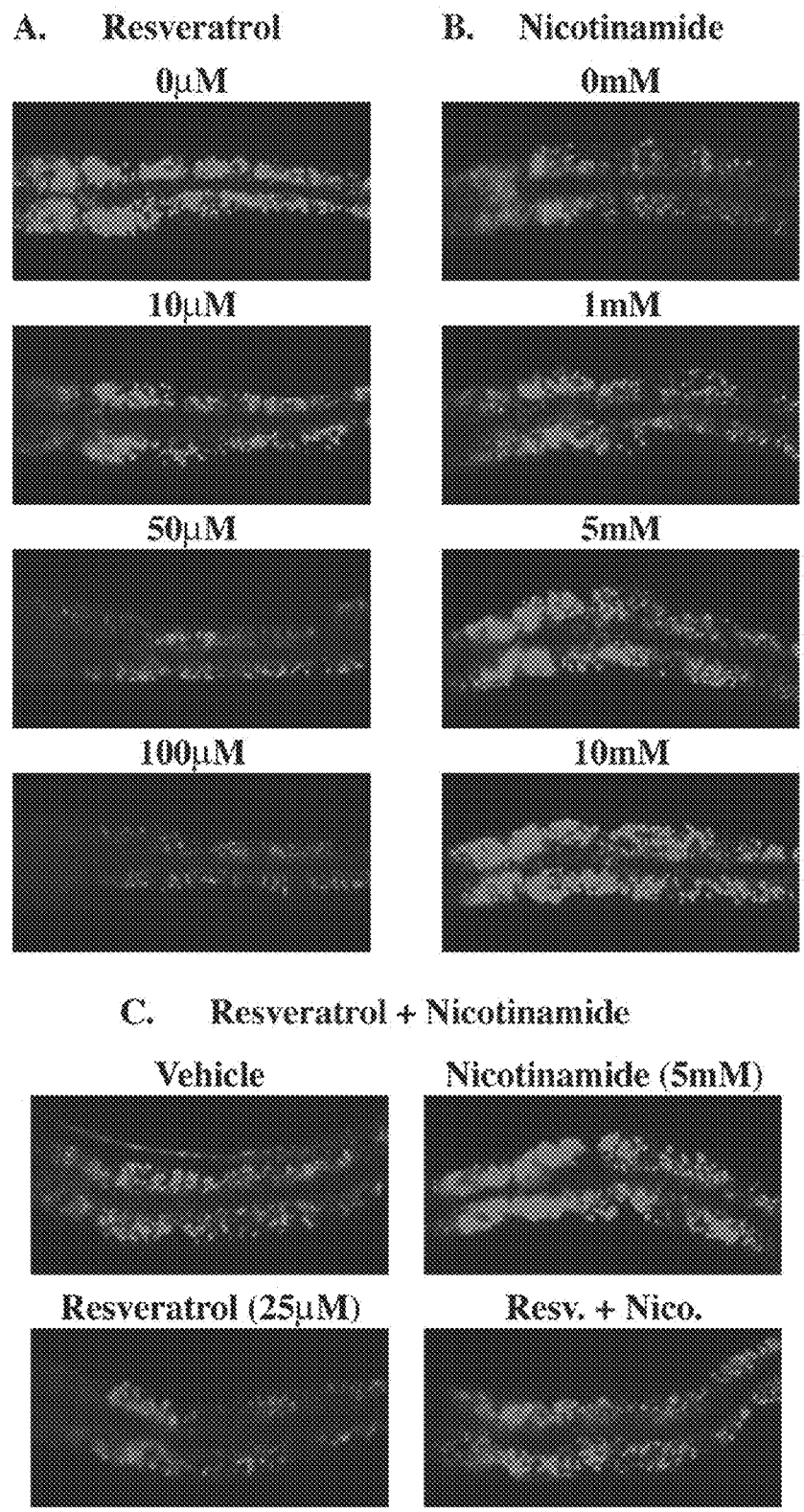
FIG. 3 is a series of photomicrographs that depict the effect of the sirtuin-inhibiting compound nicotinamide on fat accumulation. A. Resveratrol stimulates fat mobilization in wild type animals. Worms grown in the presence of vehicle alone, or 10 μM, 59 μM, and 100 μM resveratrol in vehicle were stained with Nile Red. B. Nicotinamide promotes fat accumulation in wild type animals. Nile Red staining in the presence of PBS alone, 1 mM, 5 mM and 10 mM nicotinamide is shown. C. Lower panel, Resveratrol and Nicotinamide have opposing effects on fat content. Effect of vehicle alone, resveratrol (25 μM), Nicotinamide (5 mM) or resveratrol 25 μM and Nicotinamide 5 mM in combination, on fat accumulation as assessed by Nile Red staining.

*C. elegans* worms were incubated overnight in the presence of 0, 1 or 10 mM nicotinamide, and stained with Nile-Red as described above. The results, which are shown in FIG. 3, indicate that the worms displayed a nicotinamide-concentration dependent increase in fat accumulation.

Example 3

Sir2 is Necessary for Resveratrol Mediated Fat Mobilization

Figure 4:
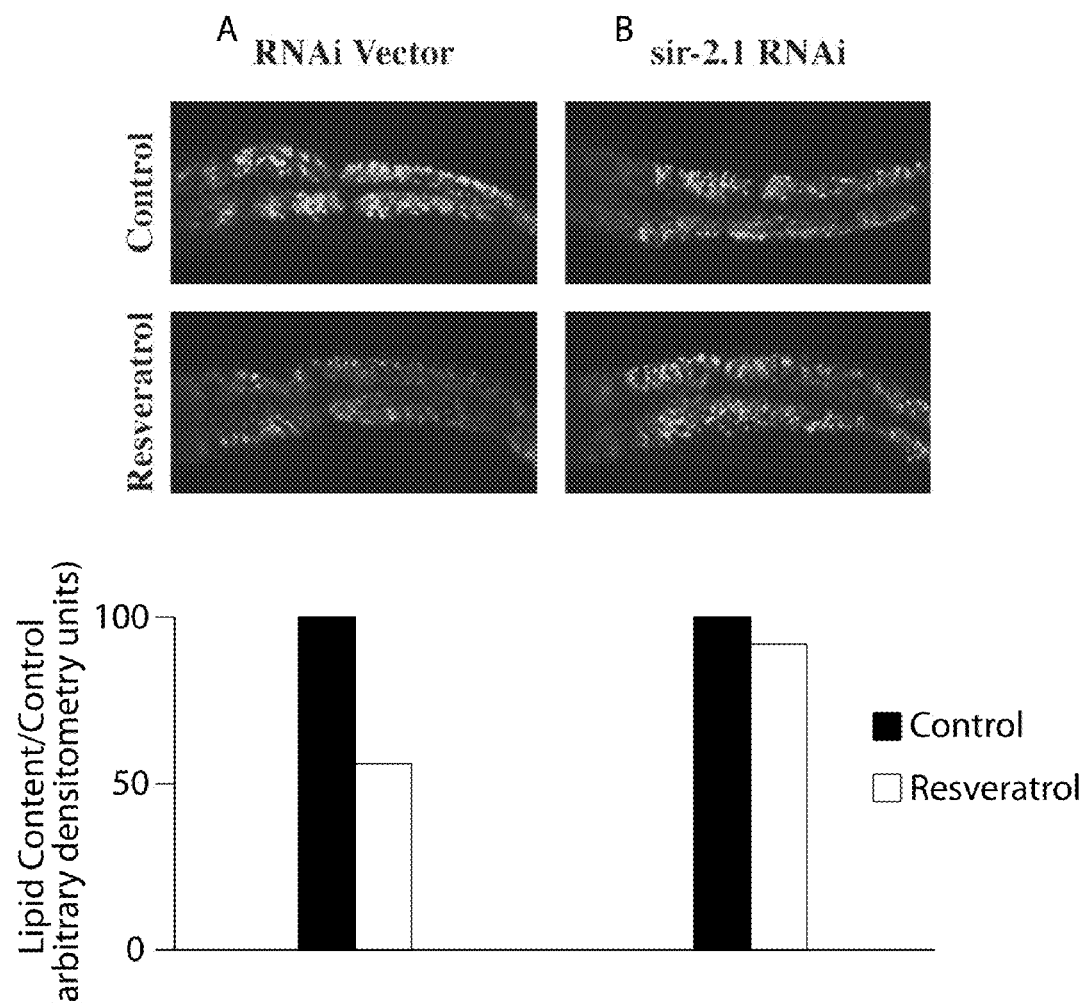
FIG. 4a-b is a series of photomicrographs that demonstrate fat content of C. elegans wild-type treated or not with Sir2.1 RNAi and incubated in the presence or absence of resveratrol.

The role of Sir2.1 in fat metabolism was shown in *C. elegans* worms in which Sir2.1 was RNA inactivated. Young adult worms were grown to adulthood in the presence of bacteria that carry RNAi vector alone or vector encoding Sir2.1 RNAi (R11A8.4), as described below. These worms were grown in the presence or absence of resveratrol, and stained with Nile-Red as described below. The results, which are shown in FIG. 4, indicate that the worms cultured in the presence of bacteria that carry Sir2.1 RNAi did not show resveratrol induced fat mobilization. These results further confirm that Sir2 is necessary for mediating the fat mobilization effect of resveratrol.

Example 4

AMPK is Necessary for Resveratrol Mediated Fat Mobilization

It was shown above that Sir2 is necessary for mediating the effect of resveratrol on fat mobilization. It is shown in this Example that AMPK is also necessary for mediating this effect. AMPK regulates diverse aspects of cell metabolism, glucose uptake and fatty acid oxidation. Many therapeutic a gents and hormones that improve insulin sensitivity, e.g., 5-aminoimidazole-4-carboxamide-1-beta-D-ribofuranoside (AICAR) and Metformin, (decrease circulating insulin levels) are known to activate AMPK signaling to glucose uptake and fatty acid oxidation. In mammals, AMPK regulates fat metabolism by stimulating fatty acid oxidation via a series of complex steps that involve phosphorylation/inactivation of acetyl coA carboxylase, release of carnitine-palmitoyl transferase-1 (CPT-1) and carnitine octanoyl transferase (COT) from end product inhibition by malonyl coA, and transport of fatty acids into the mitochondria to be oxidized.

We have examined the *C. elegans* database and found two gene products that are highly related to mammalian AMPK, TOC1.8 and Par2.3; five genes encoding homologs of CPT-1 and one gene encoding a homolog of COT. *C. elegans* worms were incubated with bacteria carrying RNAi vector alone, or interfering RNA against TOC1.8 or F41E7.3, a *C. elegans* homologue of COT in the presence or absence of AICAR. Fat accumulation was visualized with Nile-Red, as described below. The results indicate that RNA inactivation of TOC1.8 or COT inhibits AICAR-stimulated fat mobilization. Thus, AICAR/AMPK signaling to fatty acid oxidation is conserved in worms and mammalian cells.

The effect of TOC1.8 and COT inactivation was then investigated in *C. elegans* incubated with resveratrol. *C. elegans* worms were incubated with bacteria carrying RNAi vector alone, or a vector encoding TOC1.8 or COT interfering RNA in the presence or absence of resveratrol. Fat accumulation was visualized with Nile-Red, as described below.

Figure 5A:
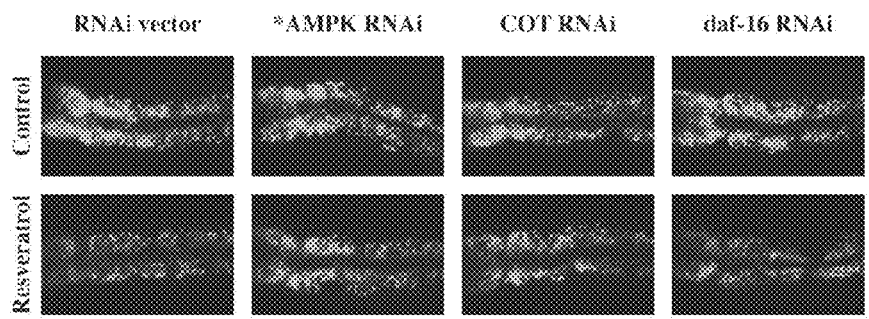
FIG. 5A a-d represents a series of photomicrographs of C. elegans incubated with empty RNAi vector (panel a); AMPK RNAi (panel b); COT RNAi (panel c) and DAF-16 RNAi (panel d) in the presence or absence of resveratrol.
Figure 5B:
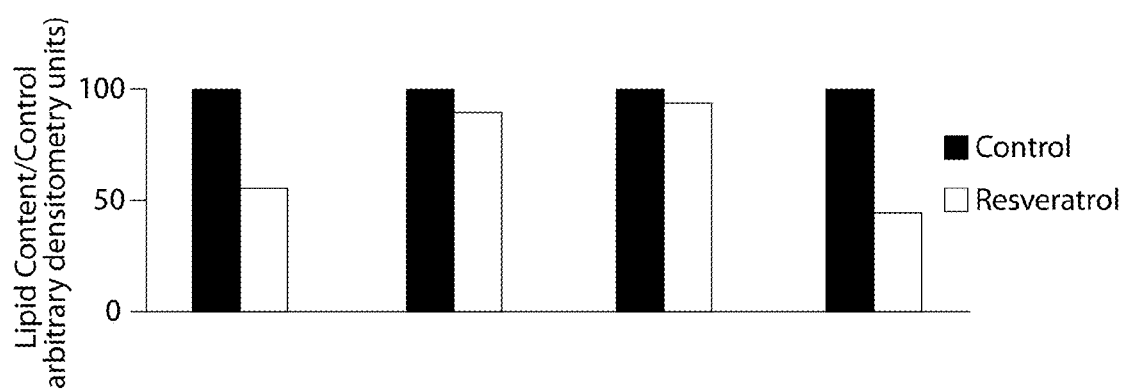
FIG. 5B represents the amount of Nile-Red staining in C. elegans shown in FIG. 5A.

The results are shown in FIG. 5. In the presence of the RNAi vector alone, resveratrol reduces fat content in normal worms by 75% (FIG. 5, panel a). However, RNA inactivation of TOC1.8, a homolog of mammalian AMPK or F41E7.3, a homolog of mammalian COT, blocks resveratrol-stimulated fat mobilization (see panels b and c of FIG. 5). Thus, AMPK is necessary for resveratrol-induced fat mobilization. Thus, we conclude that resveratrol, analogous to the direct AMPK activator AICAR, stimulates the AMPK signaling cascade to fat metabolism in worms. In contrast, RNA inactivation of DAF-16, the transcription factor downstream of insulin signaling to longevity, or inactivation of DAF-16 by mutation, had no effect on resveratrol-stimulated fat mobilization (see panel d of FIG. 5).

Thus, inhibition of the resveratrol effect by RNA inactivation of AMPK and COT suggests that mobilization of fat requires activation of the AMPK signaling cascade to fatty acid oxidation.

Example 5

AICAR and Resveratrol Stimulate AMPK and ACC Phosphorylation

RNA inactivation of AMPK and COT suggested that the effect of resveratrol and AICAR to mobilize fat in worms is dependent on activation of the AMPK signaling cascade to fatty acid oxidation. To obtain direct evidence of AMPK activation, we examined whether resveratrol-stimulated cells show increased phosphorylation of threonine residue 172 in AMPK or increased phosphorylation of acetyl coA carboxylase (ACC) at serine 79, modifications that correlate with activation of AMPK and inactivation of ACC, respectively.

CHO-HIR mammalian cells were washed in PBS and incubated overnight in serum-free DMEM before treatment with 500 μM AICAR (positive control) or 12.5 μM, 25 μM or 50 μM resveratrol. Cells were harvested after 30 minutes and lysates were immediately boiled in SDS and subjected to Western analysis with site-specific antibodies. Phosphorylation of AMPK at Thr172 indicates activation of the kinase. Active AMPK phosphorylates and inactivates ACC at serine 79.

Figure 6:
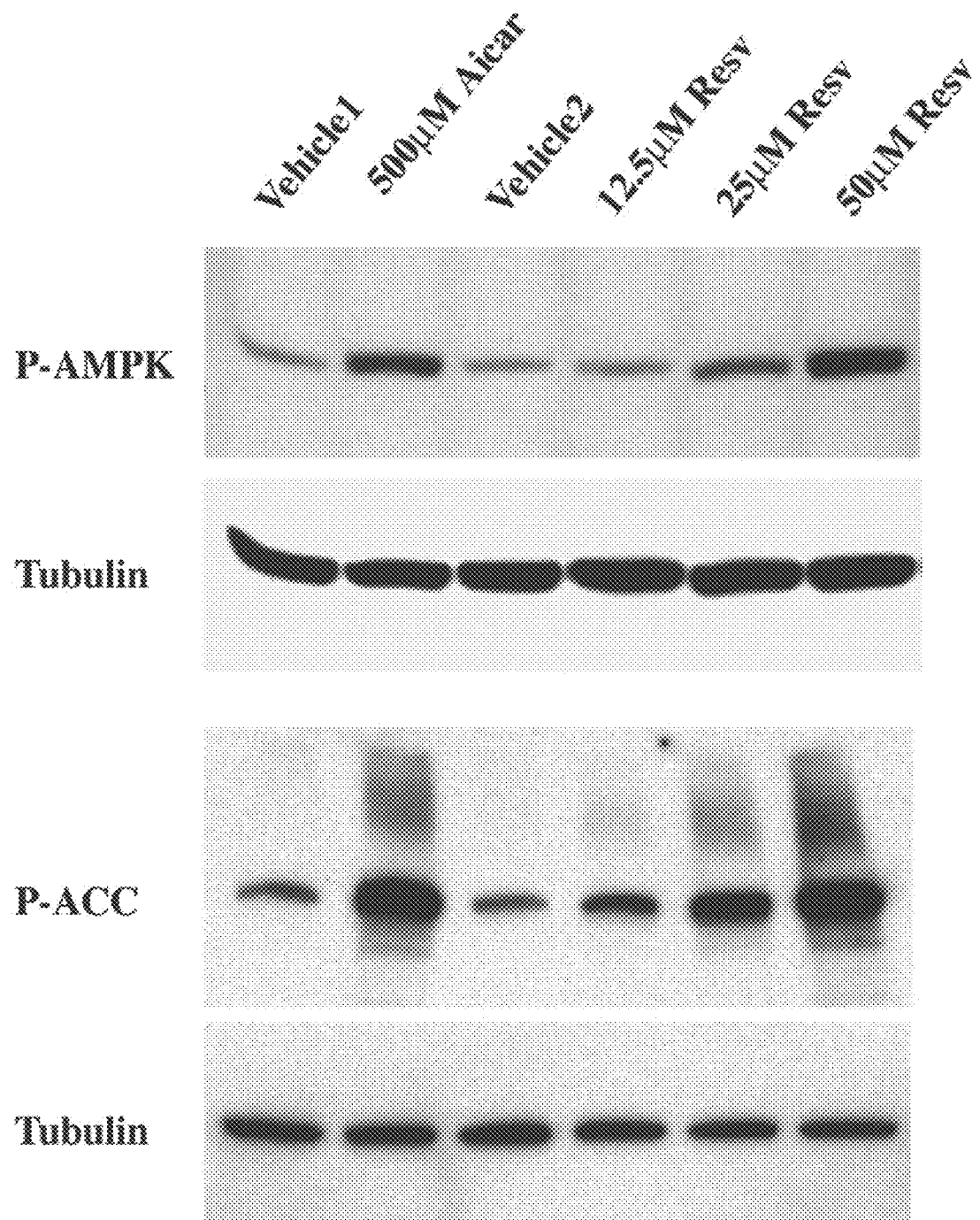
FIG. 6 shows a Western Blot of proteins from C. elegans incubated in the presence or absence (control) of 500 μM AICAR, vehicle 2 (DMSO), 12.5 μM, 25 μM or 50 μM resveratrol and stained for the presence of AMPK, ACC, or tubulin.

The results, which are shown in FIG. 6, indicate phosphorylation of AMPK on threonine 172 and phosphorylation of ACC on serine 79. Thus, like AICAR, resveratrol stimulates phosphorylation of AMPK and ACC. Accordingly, the ability of resveratrol to mobilize fat from lipogenic tissues is due, at least in part, to activation of AMPK signaling to fatty acid oxidation.

Figure 7:
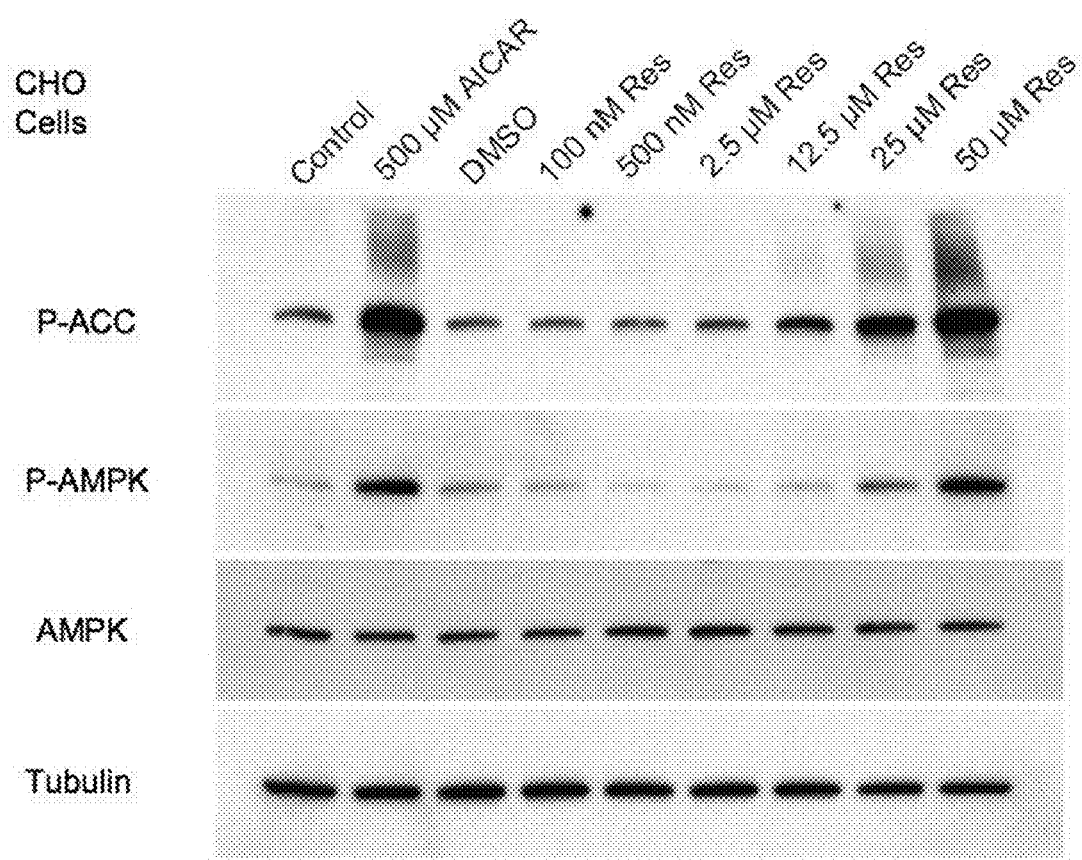
FIG. 7 shows a Western Blot of proteins incubated in the presence or absence (control) of 500 μM AICAR, DMSO, 100 nM, 500 nM, 2.5 μM, 12.5 μM, 25 μM or 50 μM resveratrol and stained for the presence of P-ACC, P-AMPK, AMPK, or tubulin.

CHO cells were also treated with 500 μM AICAR (positive control), DMSO, 100 nM, 500 nM, 2.5 μM, 12.5 μM, 25 μM, or 50 μM resveratrol and subject to Western Blot analysis as described above. Western blots were stripped and re-probed for phosphorylated (active) AMPK, total AMPK, phosphorylated acetyl CoA carboxylase (ACC), which is the downstream target of AMPK, and tubulin, which served as a loading control. FIG. 7 shows activation of AMPK in CHO cells with increasing concentrations of resveratrol.

Figure 8:
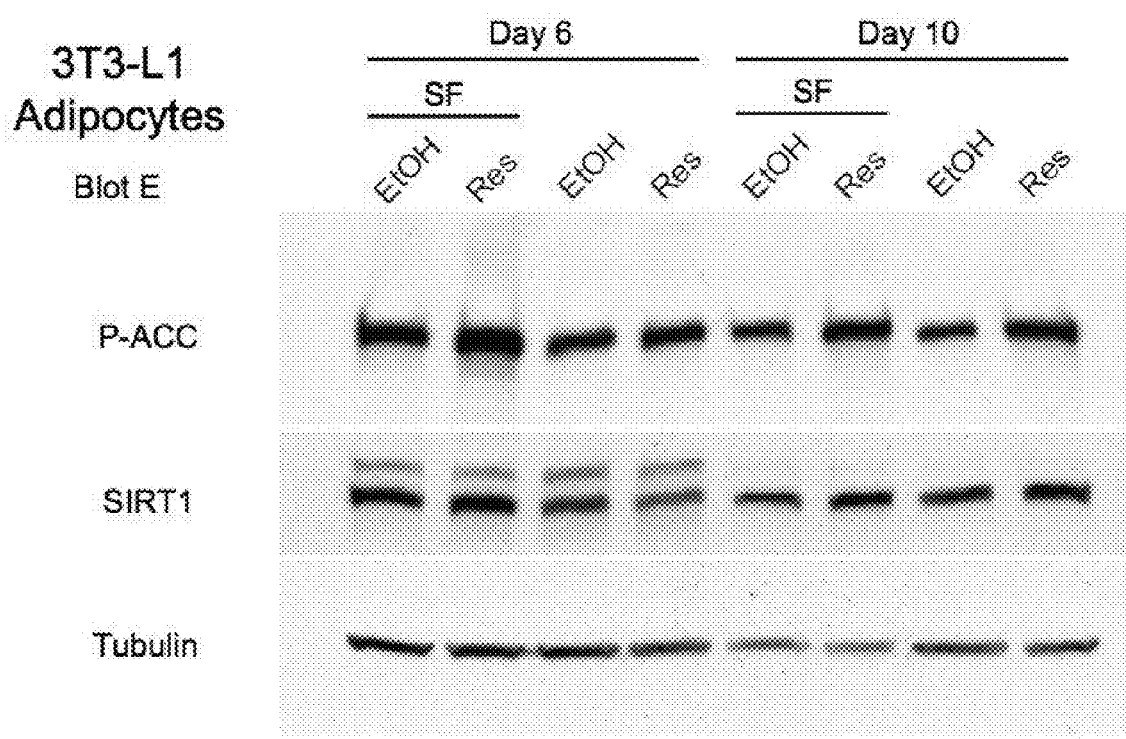
FIG. 8 is a Western Blot showing the phosphorylation of ACC in 3T3-L1 adipocytes treated either with ethanol or resveratrol and stained for the presence of P-ACC, SIRT1, or tubulin. In the lanes marked "SF", cells were left in serum free media overnight before harvesting.

Phosphorylation of ACC, which reflects AMPK activity, was also observed in 3T3-L1 adipocytes treated with either ethanol or resveratrol. 3T3-L1 cells were incubated with either ethanol or resveratrol and then harvested either 6 or 10 days after they were induced to differentiate into adipocytes from the parent 3T3 fibroblast cell line. FIG. 8 shows that resveratrol stimulated the phosphorylation of ACC at both day 6 and day 10. ACC was also phosphorylated when the cells were incubated in serum free media overnight before harvesting (lanes marked "SF"). The reason for the extra band in the SIRT1 blot at day 6 is unknown, but we hypothesize that it may be a modified form of SIRT1. Tubulin served as a loading control.

Figure 9:
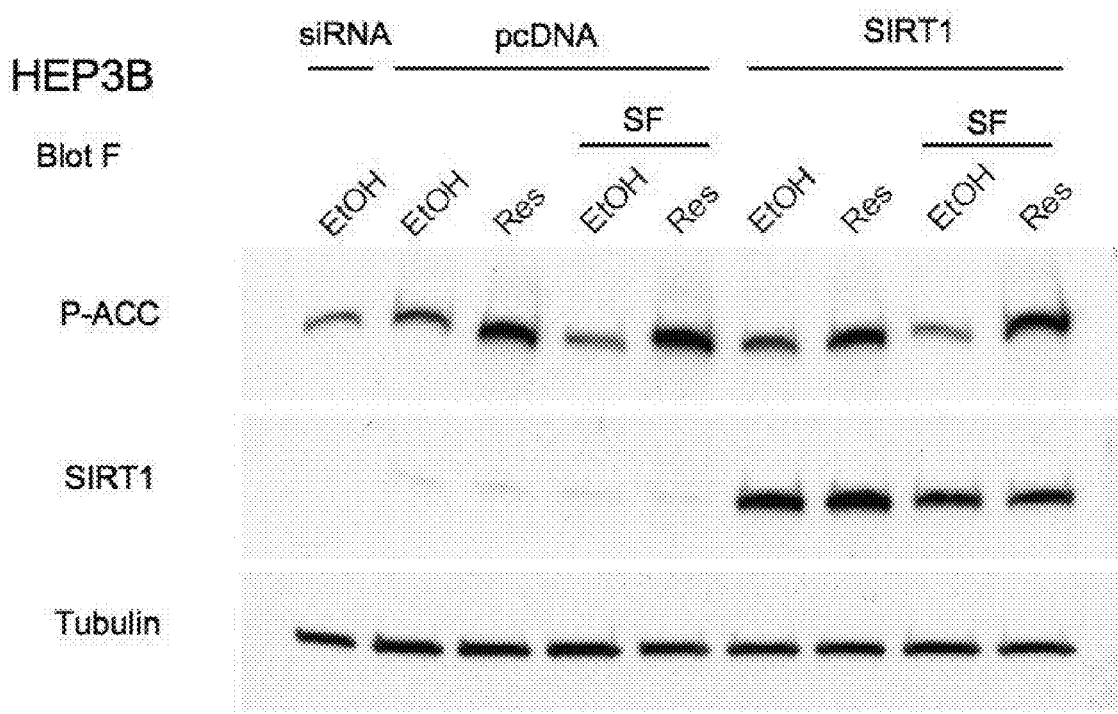
FIG. 9 is a Western Blot showing the phosphorylation of ACC in HEP3B human heptoma cells treated with either ethanol or resveratrol and stained for the presence of P-ACC, SIRT1, or tubulin. In the left lane, SIRT1 was knocked down. In the right four lanes, SIRT1 has been overexpressed.

Similar results were also observed for HEP3B human hepatoma cells. In this case phosphorylation of ACC was measured in cells were SIRT1 was overexpressed (see FIG. 9, 4 right lanes) and in cells were SIRT1 was knocked down (FIG. 9, left lane). Phosphorylation of ACC was not affected indicating that resveratrol may not be working through SIRT1 in this case. Tubulin served as a loading control.

Figure 10:
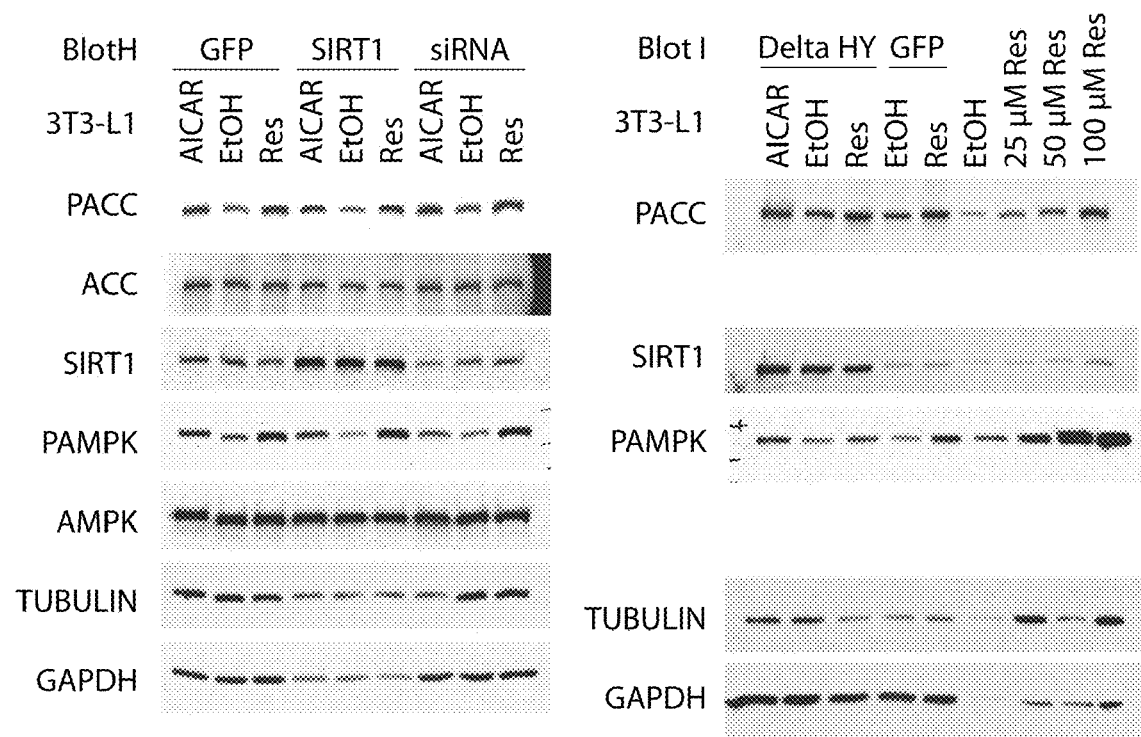
FIG. 10 is a Western Blot of proteins from 3T3-L1 adipocytes infected with either a control (GFP) retrovirus, SIRT1, SIRT1 siRNA, or SIRT1 dominant negative (delta HY). Cells were incubated in the presence of AICAR, ethanol, or resveratrol and stained for the presence of P-ACC, ACC, SIRT1, P-AMPK, AMPK, tubulin, or GAPDH. A dose response curve is shown on the far right of the blot.

To further investigate whether resveratrol is working through SIRT1, 3T3-L1 adipocytes were infected with a control (GFP) retrovirus, SIRT1, SIRT1 siRNA, or SIRT1 dominant negative (delta HY). Cells were treated with AICAR; ethanol, or resveratrol. As described above, cells were harvested and lysates were prepared for Western blot analysis with site-specific antibodies. FIG. 10 shows phosphorylation of ACC and AMPK, which reflects A MPK activity. Total protein for each is also shown. It is also noted that the loading controls, GAPDH and tubulin, are expressed but at extremely low levels in these cells and may only reflect the presence of undifferentiated 3T3 cells. FIG. 10 also shows a separate dose-response curve on the far right.

Figure 11:
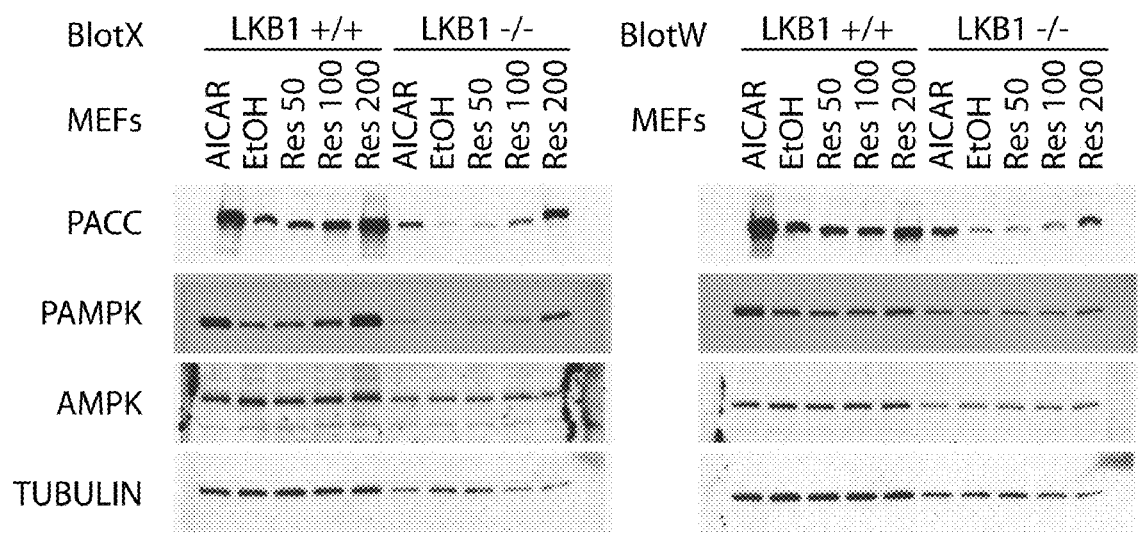
FIG. 11 is a Western Blot showing the effects of resveratrol in the presence or absence of AMPK kinase, LKB1. Mouse embryonic fibroblasts were incubated in the presence of AICAR, ethanol, 50, 100, 200 μM of resveratrol. Blots were stained for the presence of P-ACC, P-AMPK, AMPK, or tubulin as indicated on the left.

Similar results were also observed in mouse embryonic fibroblast (MEFs). FIG. 11 shows that resveratrol still has effects in the absence of the known AMPK kinase, LKB1. Cells in the left panel were incubated overnight without serum before harvesting; the cells on the right were not incubated under serum free conditions. While loading is lower for the LKB1−/− cells, resveratrol still causes an upregulation of both AMPK and ACC phosphorylation. Tubulin served as a loading control.

Example 6

Figure 12:
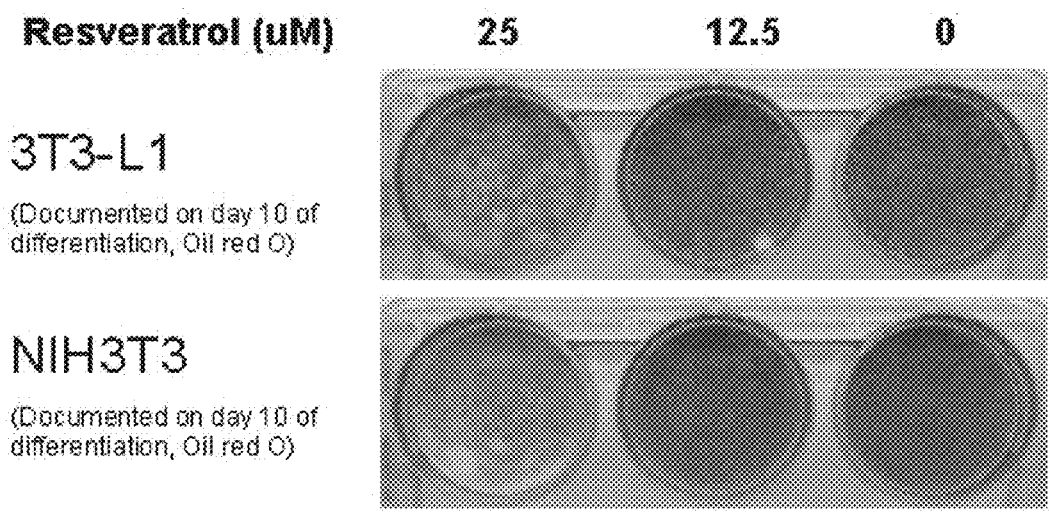
FIG. 12 shows that resveratrol inhibits lipid accumulation during mammalian adipogenesis. A. 3T3-L1 and NIH3T3 cells were differentiated into adipocytes in the presence of 25 μM, 12.5 μM or 0 μM resveratrol in vehicle (ethanol). After 10 days of differentiation, cells were fixed and stained with Oil red O. Oil red O was extracted from stained cells and quantified by measuring absorbance at 520 nm. B. Oil red O quantitation is shown as fold change relative to the 3T3-L1 sample treated with 0 μm resveratrol.
Figure 12:
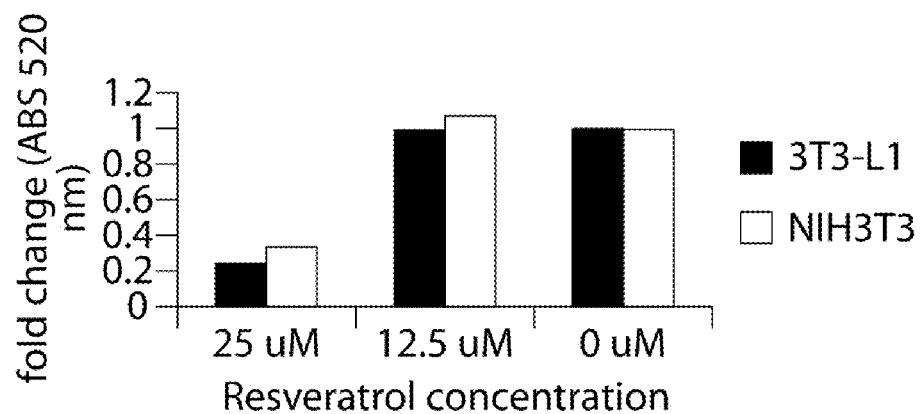

Resveratrol Stimulates Fat Mobilization and Inhibits Adipogenesis in Mammalian Cells To obtain evidence that resveratrol affects fat metabolism in a physiologically relevant cell, we examined the effect of increasing concentrations of resveratrol on 3T3-L1 and NIH3T3 cell differentiation and fat content. 3T3-L1 or NIH3T3 cells were grown to confluence and allowed to pack in for 2 days at which point differentiation was initiated by addition of isobutylmethylxanthine, dexamethasone and insulin in the presence of vehicle (ethanol alone) or resveratrol at concentrations of 0, 12.5 and 25 µM. After 10 days of differentiation, fat content was assessed by Oil Red O staining, as described below. The results, which are shown in FIG. 12, indicate that concentrations of 25 µM or higher resveratrol decreased the quantity of cellular fat in 3T3-L1 and NIH3T3 cells. The results in NIH3T3 cells confirm the results obtained in C. elegans. The results indicate that resveratrol inhibits adipogenesis (or adipocyte differentiation).

AICAR stimulates AMPK signaling and inhibits adipogenesis in 3T3 cells. To distinguish whether the effect of resveratrol was to inhibit differentiation or mobilize fat from 3T3 cells, we examined whether resveratrol inhibited the expression of adipogenic transcription regulators such as PPAR-γ. We found that cells exposed to resveratrol did not show an increase in PPAR-γ RNA, which typically accompany differentiation of the cells into adipocytes. This suggests that resveratrol inhibits differentiation of cells into adipocytes. This may also suggest that resveratrol inhibits PPAR-γ activity or expression.

Figure 13:
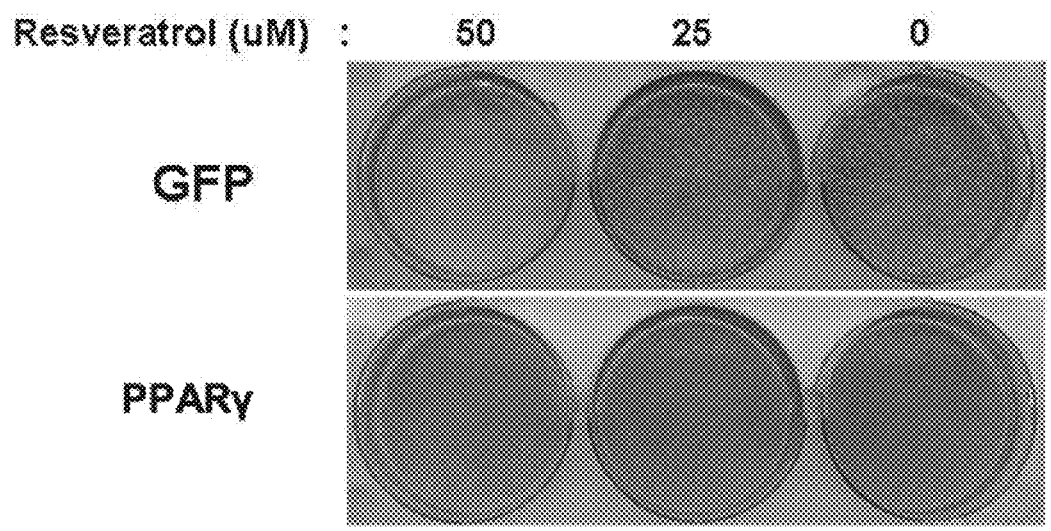
FIG. 13 shows that resveratrol inhibits adipogenesis, and that this is rescued by PPARγ. A marked decrease in PPARγ expression was detected in resveratrol-treated 3T3-L1 cells. In a separate experiment, 3T3-L1 cells were grown in the presence of virus encoding gfp or PPAR-gamma and 25 μM, 12.5 μM or 0 μM resveratrol in vehicle (ethanol). After 8 days of differentiation, cells were fixed and stained with Oil red O.

We then infected 3T3 preadipoctyes/adipocytes with pMX alone or pMX encoding PPAR-γ and examined the effect of resveratrol on 3T3 cell differentiation. 3T3-L1 and NIH3T3 cells were infected with a plasmid expressing GFP or PPAR-γ and grown to confluence. Cells were differentiated into adipocytes as described below in the presence of 0 µM, 25 µM or 50 µM resveratrol in vehicle (ethanol). After eight days of differentiation, cells were fixed and stained with Oil red O. As expected, overexpression of PPAR-γ partially negated inhibition of 3T3 preadipocyte differentiation by resveratrol (FIG. 13). This observation suggests that resveratrol inhibits PPAR-γ activated fat cell differentiation.

Figure 14:
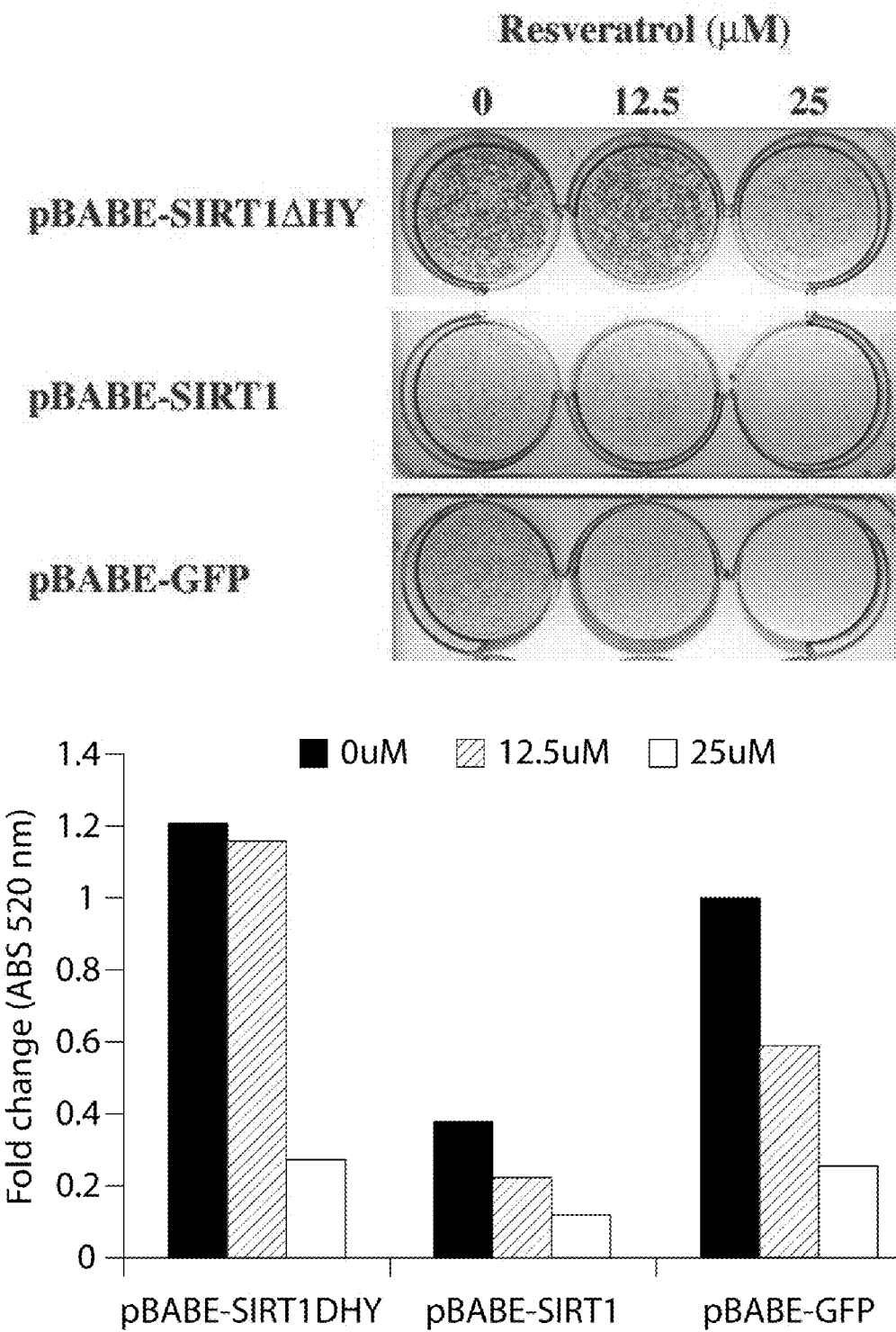
FIG. 14 shows that resveratrol inhibits lipid accumulation and the partial rescue by deacetylase deficient SIRT1. NIH3T3 cells were grown in the presence of virus encoding gfp, SIRT1 or deaceytlase deficient SIRT1. Cells were differentiated into adipocytes in the presence of 25 μM, 12.5 μM or 0 μM resveratrol in vehicle (ethanol). After 8 days of differentiation, cells were fixed and stained with Oil red O. Oil red O was extracted from stained cells and quantified.

To further examine whether resveratrol activation of sir2 could promote fat mobilization or inhibition of differentiation in mammalian cells, we infected growing cells with wild-type SIRT1 or a deacetylase deficient form of SIRT1. NIH3T3 cells were grown in the presence of virus encoding GFP, SIRT1 or the deacetylase deficient form of SIRT1 (SIRT1ΔHY) (described in Vaziri et al. (2001) Cell 107:149). C ells were differentiated into adipocytes in the presence of 0 µM, 12.5 µM or 25 µM resveratrol in vehicle (ethanol). After eight days of differentiation, cells were fixed and stained with Oil red O. The results, which are shown in FIG. 14, indicate that 3T3 cells that overexpress wild-type SIRT 1 show decreased fat content as compared to cells infected with virus encoding GFP (a negative control), while 3T3 cells that overexpress the deacetylase deficient form of SIRT1 show an increase in fat content. These results confirm the effect seen in worms, i.e., that SIRT activation by resveratrol appears to decrease fat content and SIRT1 inactivation by nicotinamide appears to increase fat content. Thus we conclude that sirtuins play a direct role in regulating fat cell differentiation and content.

The decrease in Oil Red O staining seen with SIRT1 overexpression approaches the level seen when cells are stimulated with resveratrol. This observation raised the question whether the SIRT1 deacetylase deficient mutant would reverse the effect of resveratrol. We found that in the SIRT1 deacetylase deficient mutant, the decrease in fat content normally induced by resveratrol was indeed partially reduced.

Thus, these results indicate that, in addition to reducing fat accumulation, resveratrol inhibits adipogenesis, and that this inhibition is also mediated at least in part by Sir2.

Example 7

Materials and Methods for Examples 3-6

Strains

C. elegans strains were maintained as described at 25° C., except when noted (Brenner (1974) Genetics 77:71). The wild type reference strain was N2 Bristol; the mutant strains were: sir-2.1(ok434), TO1C8.1(ok524), and daf-16 (mgDf47). Daf-16 (mgDf47) was obtained from the Ruvkun laboratory, MGH; all other strains were obtained from the Caenorhabditis Genetics Center (from C. Elegans Gene Knockout Consortium).

Growth Conditions and Resveratrol Exposure

Synchronized starved L1 worms were grown in the presence of Nile Red. Strains were grown on NGM plates at 25° C. for approximately 48 hours until the young adult stage was reached. 20-30 young adult worms were then washed 2× with M9 buffer and transferred to new NGM/Nile red experimental plates that contained either OP50 or HTT5 E. coli carrying the L4440 RNAi control vector. For experiments comparing the effect of nicotinamide and resveratrol on fat mobilization, OP50 plates were coated with vehicle alone or Nicotinamide (in PBS), or vehicle alone and Resveratrol (in Ethanol or DMSO).

RNAi plates were seeded with HTT5 E. coli carrying either the L4440 RNAi vector control or the specific RNAi clones TO1C8.1, AMPK; R11A8.4, sir-2.1; or F41E7.6 COT in the presence or absence of 100 µM resveratrol. Young adults were transferred to plates containing the appropriate vector, Nile Red stain and drug then maintained at 25° C. Nile Red staining was assessed 24 hours after resveratrol treatment by UV microscopy.

Resveratrol/Nicotinamide Dilutions

Resveratrol (Indofine #024964) was dissolved in Ethanol or DMSO to a 10 mM stock solution. Resveratrol was added to 60 mm NGM agar dishes containing either OP50 or RNAi expressing bacteria (HT115) to a final concentration of 10 μm, 50 μm, and 100 μM. Nile Red was also added to plates to a final concentration of 0.05 μg/ml. Nicotinamide (Supelco #47865-U) was diluted in PBS including Nile Red and added to 60 mM dishes containing OP50 to a final concentration of 1 mM, 10 mM, or 100 mM.

Fat Staining

Nile Red: Nile Red Powder (Sigma #N-3013) was dissolved in acetone at 500 μg/ml, diluted in 1× Phosphate Buffered Saline (PBS) including appropriate drug and applied to surface of Nematode Growth Media (NGM) plates previously seeded with OP50 or RNAi bacteria, at a final concentration of 0.05 μg/ml. Fat content was monitored and recorded by fluorescence microscopy.

Fluorescence Microscopy and Image Acquisition

Nile Red Staining was visualized by using a Nikon TE2000S microscope equipped with a CY3 filter (emission 535-685 nm). Images were captured using a SPOT RT monochrome digital camera attached to the Nikon Microscope with SPOT RT software v3.5. All Nile red images were acquired using identical settings and exposure times and then changed to red palette.

Feeding RNAi

HT115 $E.$ $Coli$ carrying the RNAi vector, L4440, were used for maintenance feeding. Bacteria containing experimental RNAi clones were cultured in 10 ml Luria Broth media containing 50 μg/ml ampicillin for 18 hours. 350 μl of each culture was spotted to a 60 mm dish containing NGM agar, 6 mM IPTG and 25 μg/ml carbenicillin. After overnight incubation (at room temp), Nile Red was added on top of each dish to a final concentration of 0.05 μg/ml along with the experimental compounds indicated in the figure legends. Nile Red staining was assessed after 24 hrs by UV microscopy. For each batch of RNAi clones tested, L4440 (vector alone) was included. A phenotype was assigned only if a majority of the animals displayed the phenotype. All phenotypes were confirmed by at least three additional rounds of testing.

Cell Culture and Oil Red O Staining

3T3-L1 and NIH3T3 cells were maintained in DMEM plus 10% calf serum. Adipocyte differentiation of 3T3-L1 cells was performed as described previously (MacDougald, O. A. and Lane, M. D. (1995). Transcriptional regulation of gene expression during adipocyte differentiation. Annu. Rev. Biochem. 64, 345-373). NIH3T3 cells were induced to form adipocytes under the same conditions as 3T3-L1 cells, but with 6 days of treatment with insulin, dexamethasone, and isobutylmethylxanthine in 10% fetal calf serum after cells reach confluence. The staining of adipocytes with Oil Red-O and quantitation was performed as described previously (Ramirez-Zacarias J L, Castro-Munozledo F, Kuri-Harcuch W Histochemistry. 1992 Jul.; 97(6):493-7).

Retrovirus Production and Infection

The mammalian retrovirus expression vector pMX (described in Tontonoz et al. (1994) Genes Dev. 8:1224, and provided by Gary Nolan) was used to construct and express full-length murine PPARγ2 (Tontonoz et al., supra), human SIRT1, human SIRT1ΔHY (Vaziri et al., supra) and eGFP. Recombinant retroviruses were generated by calcium phosphate transfection of the retroviral constructs into Phoenix ecotropic packaging cells (described in Tontonoz et al., supra, and provided by Gary Nolan), which were maintained in DMEM plus 10% fetal calf serum. Media was changed the next day and viral supernatant was harvested twice at 48 and 72 hr post-transfection of packaging cells. Viral supernatant was passed through a 0.2 μM syringe filter and applied to pre-confluent 3T3-L1 and NIH3T3 cells after addition of polybrene to a final concentration of 6 μg/ml. Media was changed the next day and cells were allowed to grow to confluence before differentiation to adipocytes.

Example 8

Figure 15:
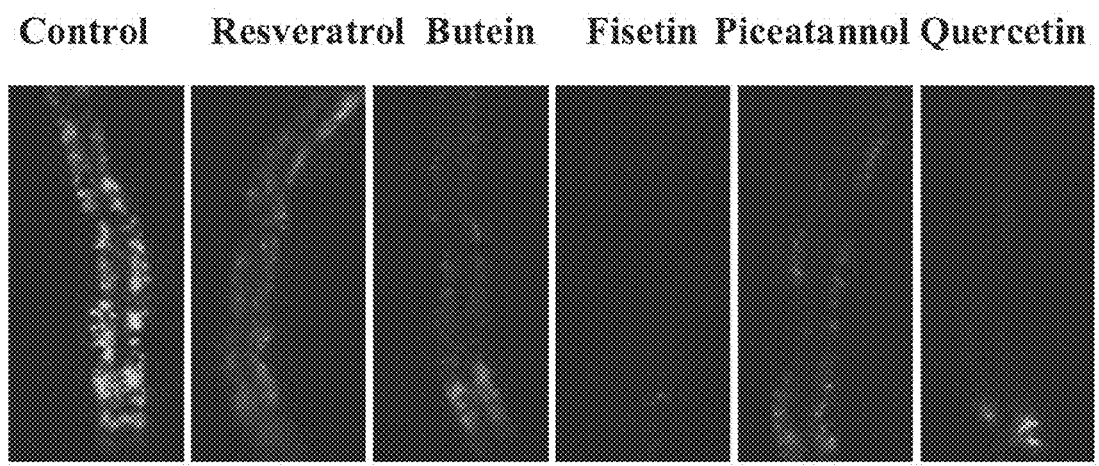
FIG. 15 shows the effect of polyphenols on C. elegans fat stores. C. elegans in L1 were exposed to Nile Red stain and vehicle (A, 20% v/v DMSO in PBS buffer) or 100 μM resveratrol, butein, fisetin, piceatannol, or quercetin for 48 hours. In each image, the head is positioned towards the bottom.
Figure 16:
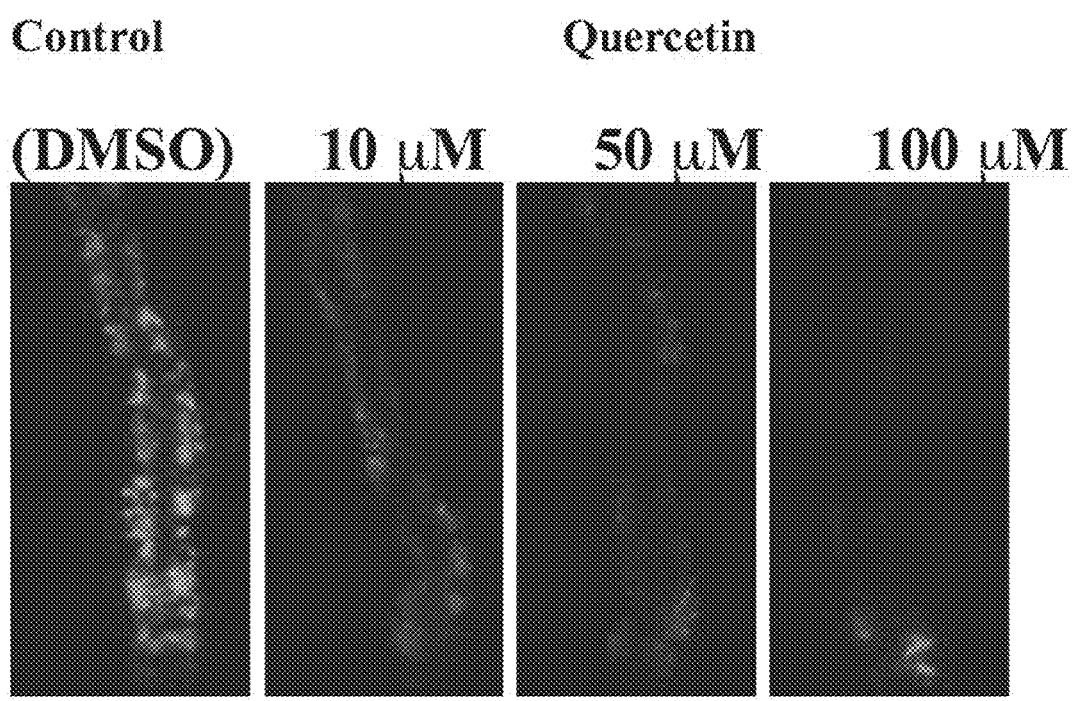
FIG. 16 shows the effect of quercetin on C. elegans fat stores. C. elegans in L1 were exposed to Nile Red and vehicle (20% v/v DMSO) or quercetin at 10 μM, 50 μM and 100 μM for 48 hours. In each image, the head is positioned towards the bottom.
Figure 17:
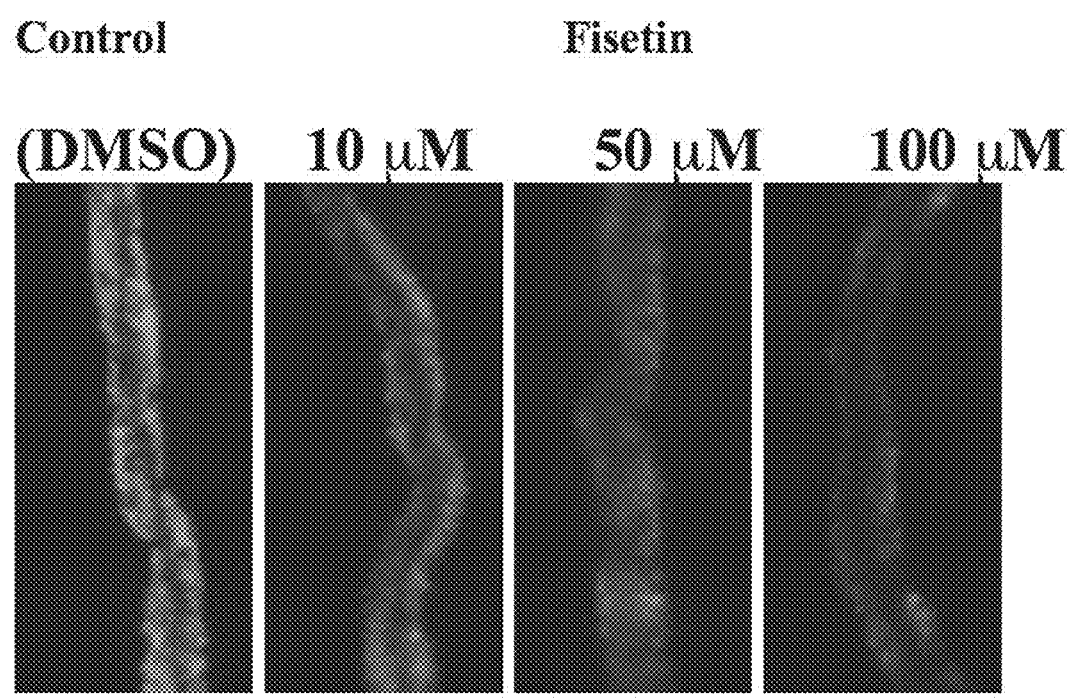
FIG. 17 shows the effect of fisetin on C. elegans fat stores. C. elegans in L1 stage were exposed to Nile Red and vehicle (A, 20% v/v DMSO) or fisetin at 10 μM, 50 μM and 100 μM for 48 hours. In each image, the head is positioned towards the bottom.

Additional Sirtuin Activators Stimulate Fat Mobilization $C.$ $elegans$ worms were incubated in the presence or absence of 100 μM of the SIRT1 activators butein, fisetin, piceatannol and quercetin, and the fat content of the worms measured as described above. The results, which are shown in FIG. 15, indicated that these SIRT1 activators have a similar effect as resveratrol, i.e., they stimulate fat mobilization. Furthermore, as shown in FIGS. 16 and 17, quercetin and fisetin reduce fat accumulation at concentrations as low as 10 μM.

Example 9

Figure 18:
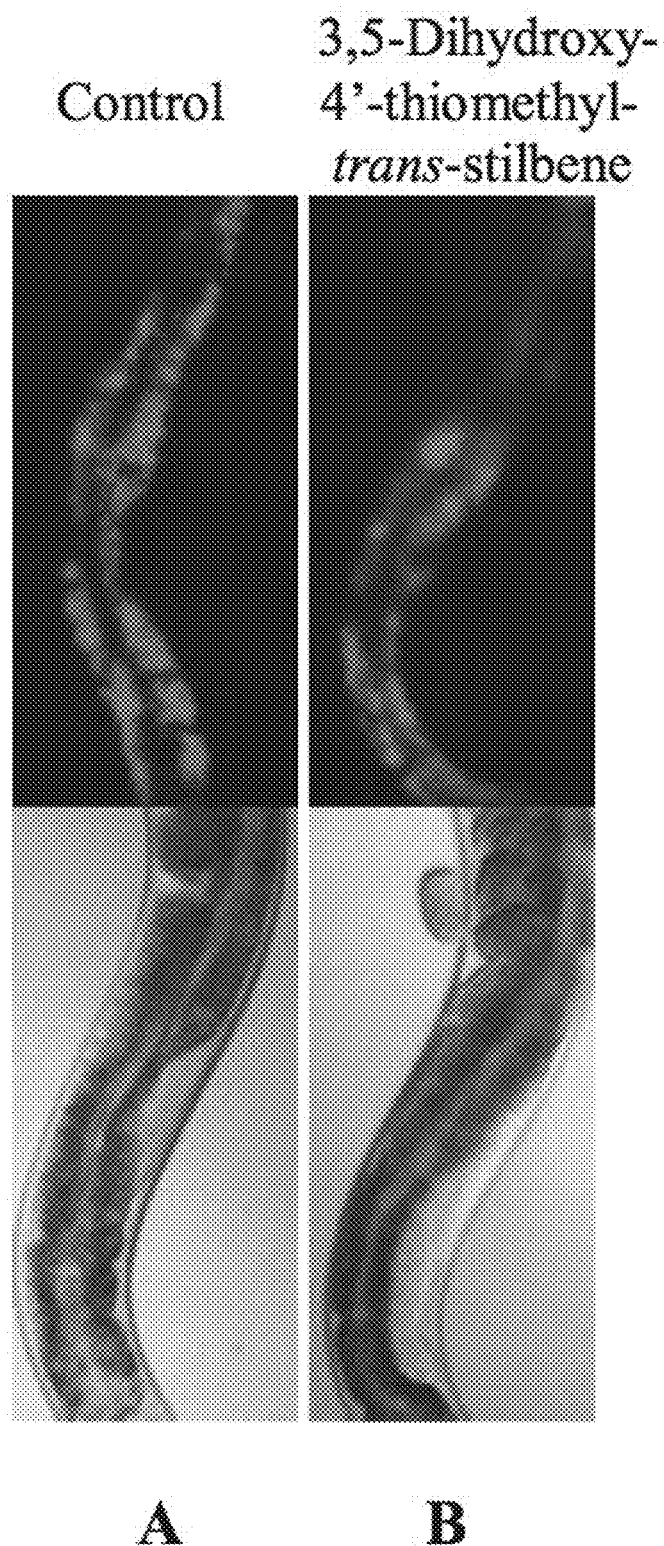
FIG. 18 shows the effect of 3,5-dihydroxy-4'-thiomethyl-trans-stilbene on C. elegans fat stores. Animals in L1 were treated with Nile Red stain and (A) 1% v/v DMSO or (B) 100 μM 3,5-dihydroxy-4'-thiomethyl-trans-stilbene for 24 hours. In each image, the head is positioned towards the bottom.
Figure 19:
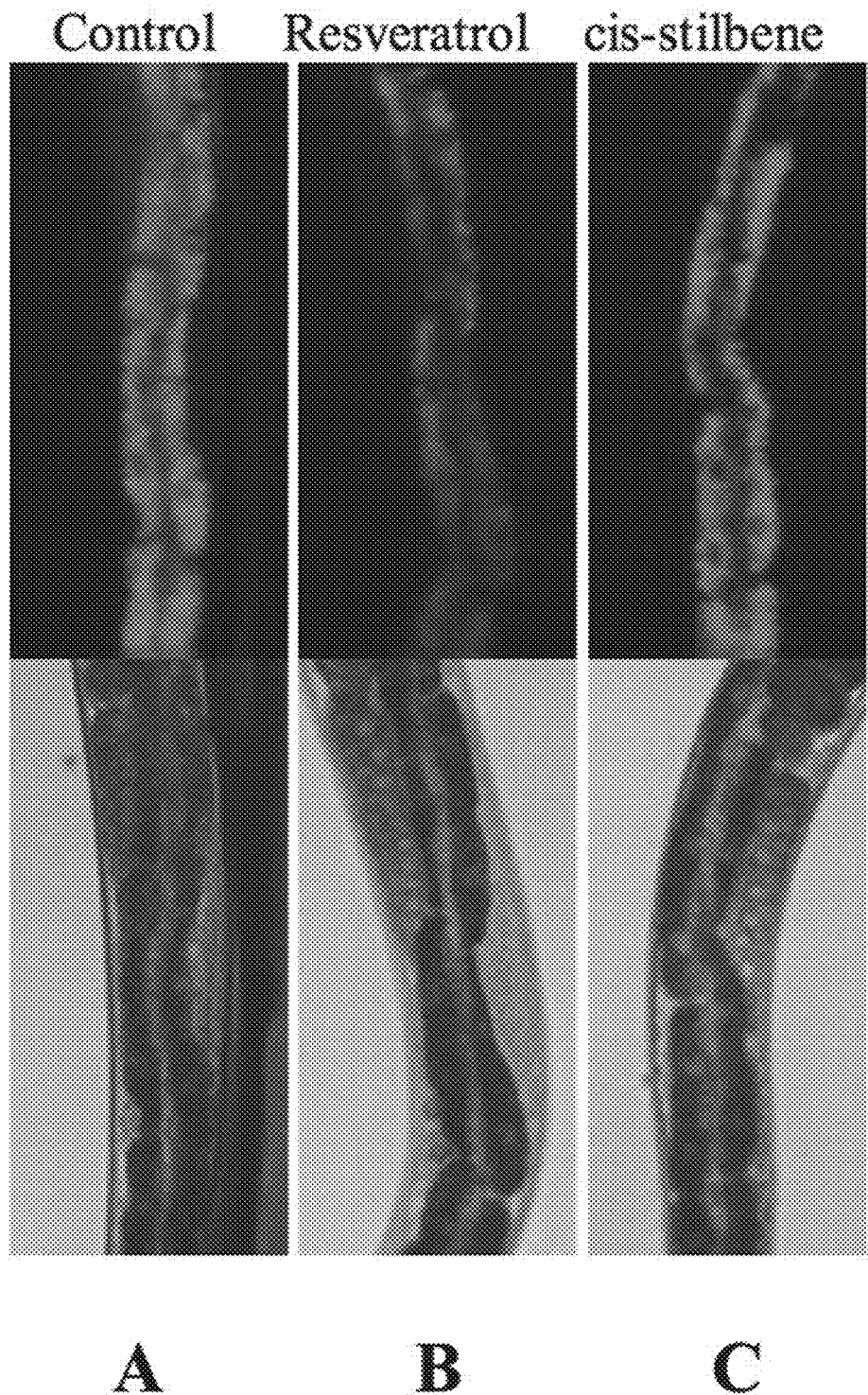
FIG. 19 compares the effect of resveratrol and cis-stilbene (a resveratrol analogue) on C. elegans fat stores. Animals in L1 were exposed to Nile Red stain and (A) 2.5% v/v DMSO, (B) 100 μM resveratrol or (C) cis-stilbene for 48 hours. In each image, the head is positioned towards the bottom.

Effects of Resveratrol Analogues on Fat Accumulation in $C.$ $elegans$ $C.$ $elegans$ worms were incubated in the absence (1% v/v DMSO) or presence of 100 μM 3,5-dihydroxy-4'-thiomethyl-trans-stilbene for 24 hours. Significant reduction of fat staining by 3,5-dihydroxy-4'-thiomethyl-trans-stilbene was observed (FIG. 18). Animals in L1 were also incubated in the absence (2.5% v/v DMSO) or presence of 100 μM resveratrol or 100 μM cis-stilbene for 48 hours. Significant reduction of fat staining by resveratrol is observed. No significant effect on worm fat staining is observed with cis-stilbene compared to the control (FIG. 19). Fat accumulation was visualized with Nile Red, a lipophilic stain, as described in Ashrafi et al., Nature 421:268-27 (2003).

Example 10

Figure 20:
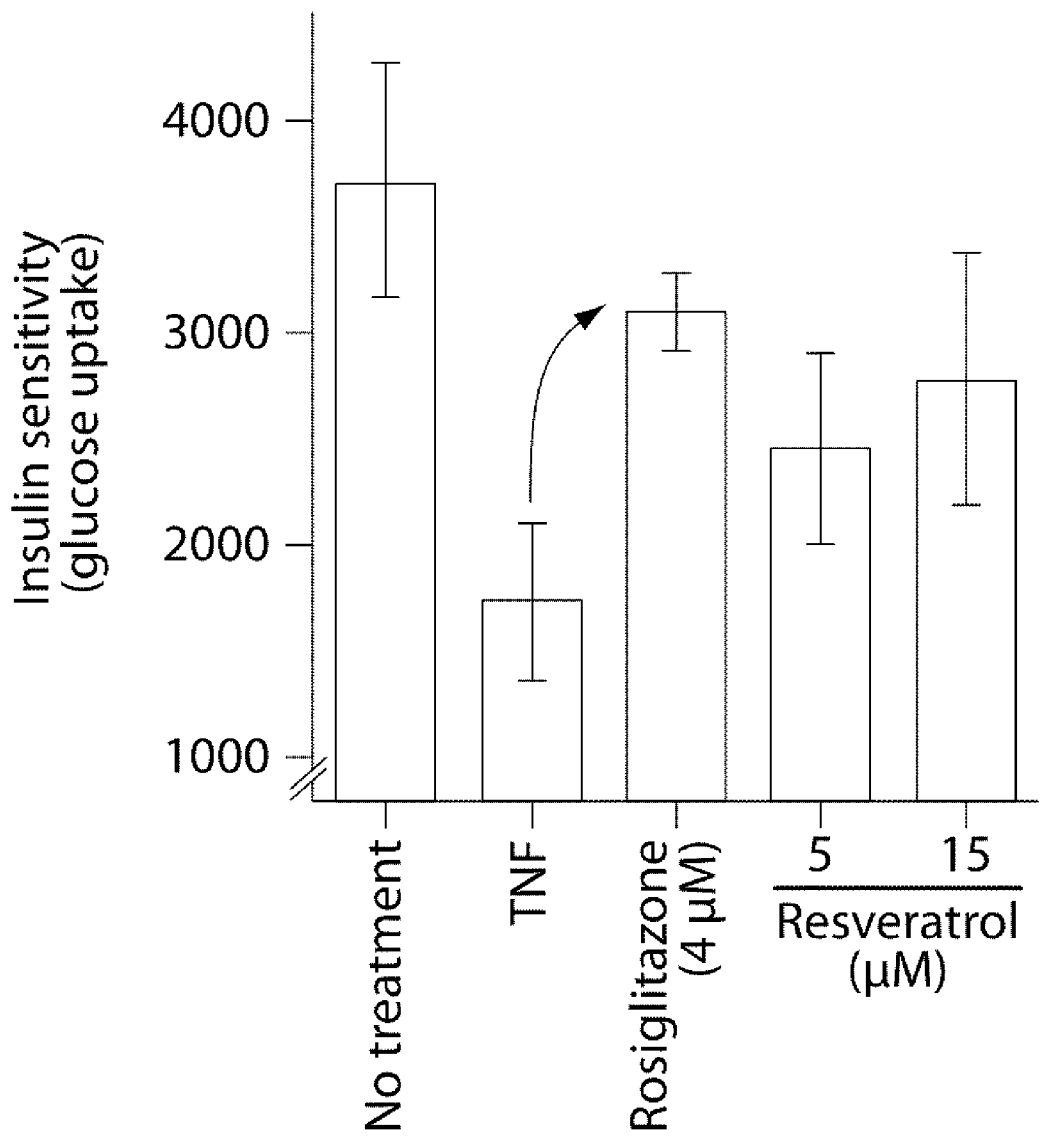
FIG. 20 shows the effect of resveratrol on TNF-alpha treated adipocytes that are insulin resistant. Lane 1, no treatment; lane 2, TNF-alpha treated; lane 3, TNF-alpha plus 4 μM roziglitazone (positive control); lane 4, TNF-alpha plus 5 μM resveratrol; and Lane 5, TNF-alpha plus 15 μM resveratrol.

Effects of Resveratrol on TNF-Alpha Treated Adipocytes that are Insulin Resistant This example shows that resveratrol boosts insulin sensitivity of adipocytes. Adipocytes were treated with TNF-alpha to induce insulin resistance as described in Kabayama et al., Glycobiology 15:21-29 (2005) and Wu et al., Mol. Cell 3:151-8 (1999). Treatment with roziglitazone, a positive control, increases the uptake of radioactive glucose indicating increased insulin sensitivity of the TNF-alpha treated adipocytes. As shown in FIG. 20, treatment with 5 μM or 15 μM resveratrol partially rescued the TNF-alpha treated adipocytes restoring insulin sensitivity in the treated cells. The arrow in FIG. 20, shows the desired effect of increased radioactive-glucose uptake.

Example 11

Resveratrol, Like Other AMPK Activators, can Stimulate Fatty Acid Oxidation in Lipogenic Cells Insulin is the major hormone charged with promoting storage of excess energy as fat. In cells with lipogenic capacity, insulin signaling promotes fat deposition. When fat stores become excessive this process is referred to as dyslipogenesis. Dyslipogenesis, is associated with insulin resistance and the progressive increase in circulating insulin and triglycerides levels, propensity to hypertension, and atherosclerosis that is characteristic of metabolic syndrome [Muller-Wieland, D. and J. Kotzka, SREBP-1: gene regulatory key to syndrome X? Ann NY Acad Sci, 2002. 967: p. 19-27]. Insulin sensitizers, such as AICAR (5-aminoimidazole-4-carboxamide-1-beta-D-ribofuranoside) and metformin, activate AMP kinase and mobilize fat from non-adipose cells thereby reducing insulin resistance and serum lipid levels [Lin, H. Z., et al., Metformin reverses fatty liver disease in obese, leptin-deficient mice. Nat Med, 2000. 6(9): p. 998-1003; Bergeron, R., et al., Effect of 5-aminoimidazole-4-carboxamide-1-beta-D-ribofuranoside infusion on in vivo glucose and lipid metabolism in lean and obese Zucker rats. Diabetes, 2001. 50(5): p. 1076-82]. Ample evidence exists that polyphenolic compounds derived from wine reduce serum lipid levels and atherosclerotic plaque [Waddington, E., I. B. Puddey, and K. D. Croft, Red wine polyphenolic compounds inhibit atherosclerosis in apolipoprotein E-deficient mice independently of effects on lipid peroxidation. Am J Clin Nutr, 2004. 79(1): p. 54-61]. Our observation that resveratrol activates AMP kinase suggested that this drug, analogous to AICAR and metformin, might be effective in reducing dyslipogenesis and increasing insulin sensitivity.

A plethora of reports indicate that AICAR and metformin activate AMPK, which in turn phosphorylates and inhibits acetyl coA carboxylase (ACC) (reviews by Kemp, B. E., et al., Dealing with energy demand: the AMP-activated protein kinase. Trends Biochem Sci, 1999. 24(1): p. 22-5; Kemp, B. E., et al., AMP-activated protein kinase, super metabolic regulator. Biochem Soc Trans, 2003. 31(Pt 1): p. 162-8; Viollet, B., et al., The AMP-activated protein kinase alpha2 catalytic subunit controls whole-body insulin sensitivity. J Clin Invest, 2003. 111(1): p. 91-8; Viollet, B., et al., Physiological role of AMP-activated protein kinase (AMPK): insights from knockout mouse models. Biochem Soc Trans, 2003. 31(Pt 1): p. 216-9; Ruderman, N. B., et al., Malonyl-CoA, fuel sensing, and insulin resistance. Am J Physiol, 1999. 276(1 Pt 1): p. E1-E18; Mu, J., E. R. Barton, and M. J. Birnbaum, Selective suppression of AMP-activated protein kinase in skeletal muscle: update on 'lazy mice'. Biochem Soc Trans, 2003. 31(Pt 1): p. 236-41; and Thou, G., et al., Role of AMP-activated protein kinase in mechanism of metformin action. J Clin Invest, 2001. 108(8): p. 1167-74). Inactivating ACC has the dual effect of inhibiting de novo fat biosynthesis and releasing fatty acid transferases carnitine-palmatoyl transferase-1 (CPT-1) and carnitine octanloyl transferase (COT) from end product inhibition by malonyl coA [Morillas, M., et al., Identification of the two histidine residues responsible for the inhibition by malonyl-CoA in peroxisomal carnitine octanoyltransferase from rat liver. FEBS Lett, 2000. 466(1): p. 183-6]. The result is decreased de novo fat biosynthesis and increased fatty acid oxidation FAO with a consequent decrease in cellular fat content.

Having shown that resveratrol increases phosphorylation of AMP kinase and ACC, see FIG. 7, we confirmed that resveratrol stimulates $CO_2$ production from palmitate in two hepatoma cell lines (Table 1). The 3- to 6-fold increase in $CO_2$ production mirrors the stimulation achieved with AICAR. In sum, our data suggests that resveratrol can stimulate fat mobilization by activating AMPK signaling to the lipogenic enzyme ACC, reducing production of malonyl coA. The latter event inhibits the flow of substrate into de novo fat biosynthesis and stimulates fatty acid oxidation.

TABLE 1

Resveratrol, like other AMPK activators, can stimulate fatty acid oxidation. Oxidation of $^{14}C$-palmitate in hepatoma cells stimulated with vehicle control (1% DMSO or H2O as appropriate), resveratrol (10 μM in 1% DMSO), AICAR (500 μM in $H_2O$), or metformin (1 mM in $H_2O$) for 4 hours as described in Methods. The fold effect of resveratrol on $CO_2$ production is shown.
14C—$CO_2$ production (nmol/hr/106 cells)
(Fold Effect)

| Compound    | Vehicle | Resveratrol | AICAR | Metformin |
|-------------|---------|-------------|-------|-----------|
| H4IIEC3 cells | 1     | 2.3         | 2.3   | 2         |
| HepG2 cells | 1       | 6           | 5     | 3.5       |

Method:

Oxidation of 14C-palmitate to acid-soluble products (modified from H4IIEC3 cells [Witters, L. A. and B. E. Kemp, Insulin activation of acetyl-CoA carboxylase accompanied by inhibition of the 5'-AMP-activated protein kinase. J Biol Chem, 1992. 267(5): p. 2864-7] and HepG2 cells were maintained as described above. Cells (106 cells/T25) were seeded in a T25 flask one day prior to the experiment. On the day of the experiment cells were washed with assay buffer (114 mM NaCl, 4.7 mM KCL, 1.2 mM $KH_2PO_4$, 1.2 mM $MgSO_4$, 11 mM glucose) before labeling with 14C-palmitate (0.4 μCi/ml) in presence of vehicle, or resveratrol (10 μM), or AICAR (500 μM) for 4 hours.

At the end of incubation, the cap of each T25 flask was replaced with a stopper and a 1'×1.5" Whatman filter paper soaked with 250 μl 2N NaOH. Each flask was injected with 2 ml of 6N HCL, placed in a horizontal position for 10 minutes and left standing overnight. The next morning, 1 ml $H_2O$ and 61 μl NaOH were added to a glass scintillation vial and the filter papers from each T25 flask were transferred to their respective vial. 10 ml Aquasol was added to each vial and allowed to stand for 2 hours, after which the vials were vortexed to dissolve the $NaH^{14}CO_2$ and counted in the scintillation counter. The results were expressed as nmols/h/106 cells and shown as the fold effect. $^{14}CO_2$ production ranged from 0.3 to 1.8 nmols/h/106 cells. The experiment was repeated three times.

EQUIVALENTS

Those skilled in the art will recognize, or be able to ascertain using no more than routine experimentation, many equivalents of the specific embodiments described herein. Such equivalents are intended to be encompassed by the following claims.

The invention claimed is:

1. A method for reducing the weight of a subject, or inhibiting weight gain in a subject, comprising administering to a subject in need thereof a therapeutically effective amount of a pharmaceutical composition consisting essentially of resveratrol.

2. The method of claim 1, wherein the pharmaceutical composition comprises one or more pharmaceutically acceptable carriers.

3. The method of claim 2, wherein the one or more pharmaceutically acceptable carriers is/are one or more liquid or solid fillers, diluents, excipients, solvents or encapsulating materials selected from the group consisting of: sugars, optionally lactose, glucose and/or sucrose; starches, optionally corn starch and/or potato starch; cellulose, and its derivatives, optionally sodium carboxymethyl cellulose, ethyl cellulose and/or cellulose acetate; powdered tragacanth; malt; gelatin; talc; excipients, optionally cocoa butter and/or suppository waxes; oils, optionally peanut oil, cottonseed oil, safflower oil, sesame oil, olive oil, corn oil and/or soybean oil; glycols, optionally propylene glycol; polyols, optionally glycerin, sorbitol, mannitol and/or polyethylene glycol; esters, optionally ethyl oleate and/or ethyl laurate; agar; buffering agents, optionally magnesium hydroxide and/or aluminum hydroxide; alginic acid; pyrogen-free water; isotonic saline; Ringer's solution; and phosphate buffer solutions.

4. The method of claim 1, wherein the resveratrol is not in a form that is naturally-occurring.

* * * * *

UNITED STATES PATENT AND TRADEMARK OFFICE
CERTIFICATE OF CORRECTION

PATENT NO. : 8,242,171 B2
APPLICATION NO. : 12/683998
DATED : August 14, 2012
INVENTOR(S) : David A. Sinclair et al.

It is certified that error appears in the above-identified patent and that said Letters Patent is hereby corrected as shown below:

In the Specification

At Column 1, Lines 16-22, please change the sentence:
"This invention was made with government support under Grant numbers GM068072 and 5RO1-AG19892 awarded by the National Institutes of Health, and Grant number GM068076 awarded by the Public Health Service/National Institutes of Health. The Government has certain rights in this invention."

To:
-- This invention was made with government support under GM068072, and AG019892 awarded by the National Institutes of Health. The government has certain rights in the invention. --

Signed and Sealed this
Thirteenth Day of August, 2024

Katherine Kelly Vidal
*Director of the United States Patent and Trademark Office*